US012728245B2

(12) United States Patent
Peris et al.

(10) Patent No.: US 12,728,245 B2
(45) Date of Patent: Sep. 8, 2026

(54) SYSTEM FOR ACCESSING A COCHLEAR IMPLANT LEAD INSERTION SITE

(71) Applicant: Spiral Therapeutics, Inc., South San Francisco, CA (US)

(72) Inventors: Hugo Peris, Richmond, VA (US); Benson Jung, Oakland, CA (US); Kevin W. Sacherman, San Francisco, CA (US)

(73) Assignee: SPIRAL THERAPEUTICS, INC., South San Francisco, CA (US)

( * ) Notice: Subject to any disclaimer, the term of this patent is extended or adjusted under 35 U.S.C. 154(b) by 0 days.

(21) Appl. No.: 19/420,283

(22) Filed: Dec. 15, 2025

(65) Prior Publication Data

US 2026/0102594 A1 Apr. 16, 2026

Related U.S. Application Data

(63) Continuation of application No. 19/418,146, filed on Dec. 12, 2025, which is a continuation of application No. PCT/US2025/047958, filed on Sep. 25, 2025.

(60) Provisional application No. 63/699,266, filed on Sep. 26, 2024.

(51) Int. Cl.

| | |
|---|---|
| ***A61M 31/00*** | (2006.01) |
| ***A61B 1/227*** | (2006.01) |
| ***A61N 1/05*** | (2006.01) |

(52) U.S. Cl.

CPC ........... *A61M 31/002* (2013.01); *A61B 1/227* (2013.01); *A61M 31/00* (2013.01); *A61N 1/0541* (2013.01); *A61M 2210/0662* (2013.01); *A61M 2210/0668* (2013.01)

(58) Field of Classification Search

CPC .......... A61B 1/227; A61M 2210/0662; A61M 2210/0668; A61M 31/00; A61M 31/002; A61N 1/0541

See application file for complete search history.

(56) References Cited

U.S. PATENT DOCUMENTS

| | | | |
|---|---|---|---|
| 5,421,818 | A | 6/1995 | Arenberg |
| 6,024,726 | A | 2/2000 | Hill |
| 6,045,528 | A | 4/2000 | Arenberg et al. |
| 6,120,484 | A | 9/2000 | Silverstein |
| 6,205,227 | B1 | 3/2001 | Mahoney et al. |
| 6,277,148 | B1 | 8/2001 | Dormer |
| 6,440,102 | B1 | 8/2002 | Arenberg et al. |
| 6,648,873 | B2 | 11/2003 | Arenberg et al. |
| 7,351,246 | B2 | 4/2008 | Epley |

(Continued)

FOREIGN PATENT DOCUMENTS

| | | |
|---|---|---|
| AU | 2002238300 B2 | 7/2007 |
| CN | 105517500 A | 4/2016 |

(Continued)

OTHER PUBLICATIONS

International Search Report and Written Opinion in International Appln. No. PCT/US2025/047958, mailed on Nov. 26, 2025, 18 pages.

*Primary Examiner* — Shefali D Patel

(74) *Attorney, Agent, or Firm* — Fish & Richardson P.C.

(57) ABSTRACT

Systems and methods can be employed for access to a middle ear for delivery of a formulation to a targeted site under direct visualization. The formulation, in some cases, can be delivered to a cochlear implant lead insertion site where a lead of a cochlear implant device enters a patient's cochlea.

23 Claims, 14 Drawing Sheets

(56) References Cited

U.S. PATENT DOCUMENTS 7,650,194 B2 1/2010 Fritsch et al.
7,704,259 B2 4/2010 Kaplan et al.
7,769,467 B1 8/2010 Emadi et al.
7,853,321 B2 12/2010 Jaax et al.
7,899,547 B1 3/2011 Emadi et al.
8,114,062 B2 2/2012 Muni et al.
8,197,461 B1 6/2012 Arenberg et al.
8,271,101 B2 9/2012 Overstreet et al.
8,515,560 B2 8/2013 Debruyne et al.
8,594,799 B2 11/2013 Haller et al.
8,718,795 B2 * 5/2014 Gibson .................. A61N 1/372 607/137
8,750,988 B2 6/2014 Jolly et al.
8,892,201 B2 11/2014 Parker et al.
8,905,922 B2 12/2014 Makower et al.
9,101,384 B2 8/2015 Makower et al.
9,162,009 B2 10/2015 Rapsey et al.
9,204,229 B2 12/2015 Koester et al.
9,308,361 B2 4/2016 Muni et al.
9,327,071 B2 5/2016 Hessler
9,352,084 B2 5/2016 Decker et al.
9,415,207 B2 8/2016 Thenuwara et al.
9,421,387 B2 8/2016 Hazard et al.
9,446,230 B1 9/2016 Alshehri et al.
9,616,207 B2 4/2017 Verhoeven et al.
9,844,666 B2 12/2017 Thenuwara et al.
10,130,514 B2 11/2018 Imran et al.
10,201,455 B2 2/2019 Kim et al.
10,244,935 B2 4/2019 Ha et al.
10,258,225 B2 4/2019 Bendory et al.
10,406,334 B2 9/2019 Verhoeven et al.
10,492,670 B1 12/2019 Bendory et al.
10,687,690 B2 6/2020 Kesten et al.
11,006,229 B2 5/2021 Schurzig
11,065,360 B2 7/2021 Lin et al.
11,083,493 B2 8/2021 Yamauchi et al.
11,116,963 B2 9/2021 Murphy et al.
11,147,713 B2 10/2021 Bendory et al.
11,154,624 B2 10/2021 Campbell et al.
11,191,960 B2 12/2021 Van den Heuvel
11,202,557 B2 12/2021 Bendory et al.
11,206,972 B2 12/2021 Bendory et al.
11,213,662 B2 1/2022 Verhoeven et al.
11,272,297 B2 3/2022 Waldmann et al.
11,298,267 B2 4/2022 Kim et al.
11,324,828 B2 5/2022 Sawhney et al.
11,413,191 B2 8/2022 Watanabe et al.
11,510,564 B2 11/2022 Bendory et al.
11,524,154 B2 12/2022 Dhanasingh
11,541,215 B2 1/2023 Kim et al.
11,660,390 B2 5/2023 Tandon et al.
11,806,492 B2 11/2023 Oplinger et al.
11,890,438 B1 2/2024 Dueck et al.
12,023,484 B2 7/2024 Murphy et al.
12,070,575 B2 8/2024 Heasman et al.
12,239,808 B2 3/2025 Tandon et al.
12,251,466 B2 3/2025 Bassett et al.
12,270,978 B2 4/2025 de Juan et al.
12,285,590 B2 4/2025 Smyth et al.
12,397,139 B1 8/2025 Sibary et al.
2003/0220536 A1 11/2003 Hissong
2004/0133099 A1 7/2004 Dyer, Jr. et al.
2004/0172005 A1 9/2004 Arenberg et al.
2004/0181185 A1 9/2004 Lee
2006/0184143 A1 8/2006 Jolly et al.
2011/0224629 A1 9/2011 Jolly et al.
2012/0071957 A1 3/2012 Carter
2012/0179187 A1 7/2012 Loushin et al.
2012/0203200 A1 8/2012 Kenney et al.
2013/0060131 A1 3/2013 Oghalai et al.
2013/0085476 A1 4/2013 Imran
2013/0245569 A1 9/2013 Jolly et al.
2016/0081656 A1 3/2016 Abraham
2016/0346511 A1 12/2016 Cohen et al.
2017/0119583 A1 5/2017 Chan et al.
2017/0172804 A1 6/2017 Watanabe et al.
2017/0354431 A1 12/2017 Rubin et al.
2017/0367892 A1 12/2017 Kim et al.
2018/0263763 A1 9/2018 Margulis et al.
2018/0303314 A1 10/2018 Noyes
2019/0015254 A1 1/2019 Bendory et al.
2019/0321610 A1 10/2019 Goldfarb et al.
2019/0350607 A1 11/2019 Martone et al.
2020/0078509 A1 3/2020 Bryning et al.
2020/0094030 A1 3/2020 Kim et al.
2021/0052868 A1 2/2021 Goldfarb et al.
2021/0059859 A1 3/2021 O'Shea et al.
2021/0228235 A1 7/2021 De Juan et al.
2021/0228237 A1 7/2021 De Juan et al.
2021/0228411 A1 7/2021 De Juan et al.
2021/0231935 A1 * 7/2021 de Juan .............. A61B 17/3478
2022/0032020 A1 2/2022 Smyth
2022/0126028 A1 4/2022 Sacherman et al.
2022/0221700 A1 * 7/2022 de Juan .............. A61B 17/3478
2023/0181886 A1 6/2023 Zuur et al.
2024/0176122 A1 5/2024 De Juan et al.
2024/0398220 A1 12/2024 Erickson et al.
2024/0398625 A1 12/2024 Erickson et al.
2025/0208395 A1 6/2025 de Juan et al.
2025/0281036 A1 9/2025 Peris et al.

FOREIGN PATENT DOCUMENTS

JP 2002-536114 A 10/2002
JP 2010-515529 A 5/2010
JP 2013-223751 A 10/2013
JP 2019-520920 A 7/2019
JP 2019-522539 A 8/2019
WO WO 2008/097317 A1 8/2008
WO WO 2019/152866 A1 8/2019
WO WO 2019/200259 A1 10/2019
WO WO 2019/204653 A1 10/2019
WO WO 2020/115674 A1 6/2020
WO WO 2020/176419 A1 9/2020
WO WO 2021/150888 A1 7/2021
WO WO 2023/055551 A1 4/2023
WO WO 2023/055719 A1 4/2023

* cited by examiner

L1
L2
L3
L4
L5
110
111
112
113
114
115
116
118
120
122
124
135
136
138
142
144
145
146
147
148
149
151
6

SYSTEM FOR ACCESSING A COCHLEAR IMPLANT LEAD INSERTION SITE

CROSS-REFERENCE TO RELATED APPLICATIONS

This application is a continuation of U.S. application Ser. No. 19/418,146 filed on Dec. 12, 2025, which is a continuation of International Application No. PCT/US2025/047958 having an International Filing Date of Sep. 25, 2025, which claims priority to U.S. Provisional Application Ser. No. 63/699,266 filed on Sep. 26, 2024. Each of these applications is incorporated by reference in its entirety.

TECHNICAL FIELD

This document relates to systems and methods for accessing the ear before, during, or after implantation of a cochlear implant lead. In some examples, the systems and methods include access to an insertion site of a cochlear implant lead for targeted delivery of a therapeutic formulation under direct visualization.

BACKGROUND

The human ear is subject to a variety of disorders that can cause significant hearing loss. In one example, SensoriNeural Hearing Loss (SNHL) is a hearing loss disorder that is due to the absence of, or damage to, hair cells in the cochlea, or to the acoustic nerve. Because these hair cells are important for translating mechanical sound waves to stimulate the cochlear nerve, SNHL can result in total hearing loss or near-total hearing loss. SNHL is typically associated with exposure to loud noise, head trauma, aging, infection, Meniere's Disease, tumors, ototoxicity, genetic diseases like otoferlin deficiency or Usher's disease, and the like. Conductive Hearing Loss (CHL) involves the loss of normal mechanical pathways for sound to reach the hair cells in the cochlea, for example due to malformation, accumulation of fluid in the middle ear, disruption of the tympanic membrane, presence of tumors, and/or damage to ossicles. Vestibular disorders include conditions that affect the vestibular system, which is responsible for maintaining balance and providing spatial orientation. The vestibular system is primarily located in the inner ear, meaning that damage to structures within the inner ear can lead to vestibular disorders.

Some patients with advanced forms of SNHL or other hearing conditions can receive a cochlear implant device to treat these conditions. A cochlear implant device may typically include a flexible lead that extends from an implant component for insertion into the cochlea. The flexible lead can be electrically connected to the implant component, and the flexible lead can include one or more electrodes to deliver electrical stimuli into the cochlea. The flexible lead of the cochlear implant is often inserted into the cochlea via an anatomic structure known as the round window opening of the cochlea, but can also be inserted through a cochleostomy. In some instances, the round window opening or other parts of the cochlea can be inflamed prior to implantation of the flexible lead. Moreover, during insertion of the flexible lead of the cochlear implant, the insertion site (at the round window opening, the cochleostomy or elsewhere along the cochlea) may be subject to inflammation or unintended fluid leakage from the cochlea.

SUMMARY

This document describes devices, systems, and methods for accessing the middle ear before, during, and/or after implantation of a lead of cochlear implant for delivery of a therapeutic formulation at a cochlear implant lead insertion site along the cochlea, which may achieve improved implant performance and durable benefits for the recipient. These devices, systems, and methods can optionally employ a minimally invasive surgical access path (already created for implantation of the cochlear implant device) or an existing anatomical passageway (such as the ear canal), thereby improving the safety of the cochlear implant delivery without added complexity for the clinician.

For example, some embodiments described herein include otologic devices, systems, and methods for minimally invasive delivery of a therapeutic formulation to a targeted site within the ear while also providing direct visualization (e.g., using a tip-mounted camera and illumination tool) of such delivery. This targeted site can, in some examples, be the round window membrane of the cochlea or a cochleostomy separate from the round window membrane. In particular implementations, the therapeutic formulation can be deposited at the targeted site, and an active agent of the therapeutic formulation can then transfer passively by diffusion, according to a concentration gradient, into the perilymph (within the cochlea). Other embodiments described herein include otologic devices, systems, and methods for delivery of a therapeutic formulation to the targeted site within the middle ear via an incision in the patient's skin and bone (e.g., a transmastoid incision behind the patient's ear) while also providing direct visualization of such delivery. The devices, systems, and methods described herein may be used to treat a variety of disorders of the middle ear and/or inner ear including, but not limited to, hearing loss and balance disorders, including vertigo, Meniere's Disease, vestibular neuronitis, vestibular schwannoma, tinnitus, labyrinthitis, otosclerosis, ossicular chain dislocation, cholesteatoma, middle ear infections, tympanic membrane perforations, and trauma around the implantation of a lead of a cochlear implant, to provide a few examples.

Some embodiments described herein include an improved instrumentation for delivering therapy at various points during a procedure to implant a medical device. For example, a patient can receive a cochlear implant to treat one or more hearing disorders. Cochlear implant devices can include a lead that is inserted into the patient's cochlea. This lead can be implanted using an invasive surgical procedure where a clinician makes an incision behind the patient's ear, drills one or more holes in the patient's mastoid bone behind the incision and inserts the lead into the cochlea via the one or more holes in the mastoid bone. Because this type of access to the cochlea involves drilling holes through the mastoid bone, this pathway to the cochlea can be referred to as a "transmastoid" pathway.

In some cases, the clinician inserts the cochlear implant lead into the cochlea at a cochlear implant lead insertion site. When the lead is securely implanted within the cochlea, a therapeutic fluid delivery tool can deliver a formulation to seal the cochlear implant lead insertion site. This tool can access the cochlear implant lead insertion site through the same transmastoid pathway that the clinician created for delivering the cochlear implant lead. Using an existing transmastoid pathway to access the cochlear implant lead insertion site can be advantageous because the therapeutic fluid delivery tool is sized to fit through this pathway in order to deliver a therapeutic formulation at the cochlear implant lead insertion site and the transmastoid pathway does not involve crossing the tympanic membrane.

Additionally, or alternatively, the therapeutic fluid delivery tool can access the cochlear implant lead insertion site through the patient's ear canal and through an opening in the tympanic membrane. This is because the therapeutic fluid delivery tool is sized to fit through the ear canal and the opening in the tympanic membrane so that the tool reaches the cochlear implant lead insertion site. Because this type of access to the cochlea involves the tool passing through the patient's natural ear canal, this pathway to the cochlea can be referred to as a "transcanal" pathway. Transcanal access can be advantageous for several reasons, namely because this kind of access is minimally invasive and does not involve major cuts through the patient's tissue and bones. In some examples, the therapeutic fluid delivery tool can deliver therapy using minimally invasive transcanal access before the procedure to implant the lead and after the procedure to implant the lead when a transmastoid pathway does not already exist for another reason (e.g., to implant the lead).

In the case of minimally invasive, trans-tympanic access, some embodiments described herein include an improved instrumentation configured to provide rapid access through a small opening in the tympanic membrane in a manner that provides a clinician with both accurate visualization and enhanced comfort/ease of use during delivery of the treatment. In particular examples described herein, a handheld otology instrument can include a handle from which first and second shafts extend distally in a side-by-side configuration, with the first shaft having a miniature tip-mounted camera fixed to a distal end of a first shaft and the second shaft having a fluid delivery lumen extending to a distal port of the second shaft. In these examples, the user can readily grasp a handle (e.g., using a pencil grip or other grip that enhances control and accuracy) to through a small radial opening on the tympanic membrane (a myringotomy) using a distal tip of the second (longer) shaft and then advancing both of the side-by-shafts through the small opening, thereby achieving a micro-incision on the tympanic membrane that is capable of self-healing and substantially the same size as the combined lateral width of the side-by-side shafts. In such examples, the opening formed in the tympanic membrane can be no greater than 2 mm, and preferably about 1 mm to about 1.8 mm. When the shafts are advanced through the opening in the tympanic membrane, the user can then accurately advance the distal port of the second shaft toward the round window membrane of the cochlea while the tip-mounted camera at the distal end of the first shaft provides direct visualization of the second shaft.

In the case of access through a transmastoid pathway, the improved instrumentation also provides rapid access in a manner that provides a clinician with both accurate visualization and enhanced comfort/ease of use during delivery of the treatment. The tool provides direct visualization when using a transmastoid pathway just as it does when using a transcanal pathway, enabling the clinician to determine when the tool is properly located to deliver the formulation. To create this transmastoid access, the clinician can make incisions, bores, and cuts to tissue and bone for the purpose of delivering a cochlear implant lead in some cases. In some cases, the tool can advance through this transmastoid pathway that already exists for the purpose of implanting the lead to reach the cochlea, without the clinician making any additional cuts, incisions, or bores to accommodate the tool.

While the user retains the handheld otology instrument in a selected position (e.g., with the distal portion of the second shaft proximate to the round window membrane and under direct visualization), the user engages an actuator (e.g., using a second hand) to achieve controlled delivery of a therapeutic formulation from the distal port and onto the targeted site. Additionally, in some embodiments, the distal portion of the second shaft can be sized for further insertion beyond the middle ear and into the inner while under direct visualization. For example, the distal portion of the second shaft can, in some embodiments, penetrate the round window membrane such that the distal port of the fluid delivery shaft is positioned within the cochlea to deliver a therapeutic formulation directly into the perilymph.

In one aspect, a system for delivering a therapeutic formulation at a cochlear implant lead insertion site of a patient includes a cochlear implant device having a lead configured to extend through the cochlear implant lead insertion site of the cochlea for implantation within the cochlea; and a therapeutic fluid delivery tool configured to deposit the therapeutic formulation at the cochlear implant lead insertion site of the cochlea. The therapeutic fluid delivery tool includes a handle connected to a therapeutic formulation delivery shaft and a visualization shaft that both extend distally from the handle and a fluid input port on the handle to connect with a treatment actuator device configured to deliver the therapeutic formulation to a fluid delivery lumen of the therapeutic formulation delivery shaft. A distal port of the therapeutic formulation delivery shaft is positioned distally of the visualization shaft and positionable adjacent to the lead of the cochlear implant device to deposit the therapeutic formulation at to seal the cochlear implant lead insertion site.

In another aspect, a system for delivering a therapeutic formulation at a cochlear implant lead insertion site of a patient includes a treatment actuator device and a therapeutic fluid delivery tool configured to deposit the therapeutic formulation at the cochlear implant lead insertion site of the cochlea. The therapeutic fluid delivery tool includes a handle connected to a therapeutic formulation delivery shaft and a visualization shaft that both extend distally from the handle and a fluid input port on the handle to connect with a treatment actuator device configured to deliver the therapeutic formulation to a fluid delivery lumen of the therapeutic formulation delivery shaft. A distal port of the therapeutic formulation delivery shaft is positioned distally of the visualization shaft and positionable adjacent to a lead of a cochlear implant device to deposit the therapeutic formulation to seal the cochlear implant lead insertion site.

In yet another aspect, a system for delivering a therapeutic formulation at a cochlear implant lead insertion site comprises a cochlear implant device having a lead configured to extend through a cochlear implant lead insertion site and a therapeutic fluid delivery tool configured to deposit a therapeutic formulation at the cochlear implant lead insertion site of the cochlea.

In yet another aspect, a therapeutic fluid delivery tool configured to deposit a therapeutic formulation at a cochlear implant lead insertion site of the cochlea includes a handle connected to side-by-side shafts that are fixedly mounted in a stationary position relative to one another and extend distally from the handle, wherein the side-by-side shafts comprise a visualization shaft and a therapeutic formulation delivery shaft having a distal port positioned distally of the visualization shaft and a tip-mounted image capture device fixedly mounted at a distal end of the visualization shaft and being connected with an image data cable extending through a lumen of the visualization shaft proximally toward the handle. The tip-mounted image capture device is sized to advance proximate to a round window opening of the cochlea and provide imaging of cochlear implant lead insertion site of the cochlea. The therapeutic fluid delivery tool further includes a fluid input port on the handle to connect with a treatment actuator device to provide fluid communication to a fluid delivery lumen of the therapeutic formulation delivery shaft, wherein the distal port of the therapeutic formulation delivery shaft is positioned distally of the visualization shaft and is sized to output a dosage of the therapeutic formulation to both seal the cochlear implant lead insertion site and provide sustained release of a therapeutic agent.

In yet another aspect, a therapeutic instrumentation system configured to deposit a therapeutic formulation at a cochlear implant lead insertion site of the cochlea, including a treatment syringe device including a reservoir containing a self-gelling therapeutic formulation comprising at least one otic therapeutic agent and a therapeutic formulation delivery shaft having a fluid delivery lumen sized to convey the self-gelling therapeutic formulation therethrough, wherein a distal port of the therapeutic formulation delivery shaft is configured to output a dosage of the self-gelling therapeutic formulation to both seal the cochlear implant lead insertion site and provide sustained release of the therapeutic agent at the cochlear implant lead insertion site.

In yet another aspect, a method of treating an ear includes advancing shafts of a handheld otologic instrument to a cochlear implant lead insertion site where a lead of a cochlear implant device enters a cochlea of a patient, wherein the advancing occurs while the trans-tympanic shafts are fixedly mounted in a stationary position relative to one another and extend distally from a distal end of a handle of the handheld otologic instrument; and using a tip-mounted camera at a distal end of a first shaft of the trans-tympanic shafts to provide imaging of a distal tip of a second shaft of the trans-tympanic shafts while a delivered amount of a therapeutic formation is deposited out of the distal tip of the of the second shaft and at the cochlear implant lead insertion site.

In yet another aspect, a method of treating an ear includes advancing shafts of a handheld otologic instrument to a targeted site within an ear of a patient, the shafts advancing through a transmastoid pathway including a hole in a mastoid bone of the patient, wherein the advancing occurs while the shafts are fixedly mounted in a stationary position relative to one another and extend distally from a distal end of a handle of the handheld otologic instrument; and using a tip-mounted camera at a distal end of a first shaft of the shafts to provide imaging of a distal tip of a second shaft of the shafts while a delivered amount of a therapeutic formation is deposited out of the distal tip of the of the second shaft and at the targeted site.

In yet another aspect, a method of treating an ear includes advancing shafts of a handheld otologic instrument to a targeted site within an ear of a patient, the shafts advancing through a an ear canal of the patient and across a tympanic membrane of the patient, wherein the advancing occurs while the shafts are fixedly mounted in a stationary position relative to one another and extend distally from a distal end of a handle of the handheld otologic instrument; and using a tip-mounted camera at a distal end of a first shaft of the shafts to provide imaging of a distal tip of a second shaft of the shafts while a delivered amount of a therapeutic formation is deposited out of the distal tip of the of the second shaft and at the targeted site.

Some or all of the embodiments described herein may provide one or more of the following advantages. First, the systems and methods described herein can include specialized techniques and instruments to treat a variety of hearing loss conditions or ear disorders, including treatments that precisely place a sustained-delivery therapeutic formulation on or across a lead insertion site of a cochlear implant (e.g., at the round window opening or to other parts of the cochlea). In some options, the therapeutic formulation can be deposited at the cochlear implant lead insertion site before the implantation procedure for the cochlear implant (e.g., to pretreat the cochlea and prepare for the subsequent insertion of the lead into the cochlea). In further options, the therapeutic formulation can be deposited at the cochlear implant lead insertion site during the implantation procedure for the cochlear implant so that the therapeutic formulation can deliver a therapeutic agent adjacent to the lead of the cochlear implant, can seal the insertion site of the lead extending into the cochlea, or both. And, in additional options, the therapeutic formulation can be deposited at the round window membrane and/or the cochlear implant lead insertion site after the implantation procedure for the cochlear implant so as to provide an additional dosage of the therapeutic agent even after the cochlear implant lead insertion site has fully or partially healed.

Second, the systems and methods described herein can advantageously achieve delivery of a therapeutic formulation to a cochlear implant lead insertion site through a trans-tympanic access path, through a trans-mastoid access path (via an incisions created for implanting the cochlear implant lead), or through a sequence of treatments that includes both access paths at different times. For example, in a trans-mastoid approach, a clinician can make one or more incisions and cuts in the patient's skin (e.g., an incision behind the patient's ear) to implant a cochlear implant device. In some cases, the clinicians can also bore, cut, or remove bone as part of implanting the lead of the cochlear implant device. The lead can be inserted into the cochlea at a cochlear implant lead insertion site through these incisions and bone cuts. While this access path to the cochlea is already open, the improved tool described herein can advantageously deliver the therapeutic formulation to seal the cochlear implant lead insertion site without requiring any additional incisions or cuts. Alternatively, the formulation can also be delivered through minimally invasive trans-tympanic access via the ear canal. In some cases, the formulation can be delivered through minimally invasive trans-tympanic access when the incisions and/or bone cuts are not open, such as before the lead is implanted or after the lead is implanted. This means that the systems and methods described herein can advantageously deliver the formulation to the cochlear implant lead insertion site using minimally invasive access or using access via already existing incisions and cuts that were created to insert a cochlear implant lead.

Third, the systems and methods described herein can advantageously provide direct visualization during delivery of the formulation to the targeted site in the middle or inner ear. Optionally, the direct visualization can be provided via a miniature camera-on-a-chip (e.g., a complementary metal-oxide semiconductor (CMOS)) image sensor having width of less than 1 mm, and preferably less than 0.6 mm, mounted at a distal end of an instrument shaft, thereby achieving a smaller overall instrument size (e.g., for the component(s) inserted through the tympanic membrane). The use of such direct visualization advantageously allows visual confirmation of the proper placement of the formulations with a high level of accuracy. The direct visualization also provides additional benefits such as the ability to ascertain visually whether there are any obstructions that could inhibit the proper delivery of the formulations. For example, in some cases the round window is covered by a pseudo membrane that can be altered or moved to allow improved access to the round window membrane. By using the improved instrumentation described herein, the presence of the pseudo membrane can be visually verified, and thereafter physically altered, moved, or navigated around, so that improved and direct access to the round window membrane can be established for more precise placement of the formulation. In other cases, delivery of the formulation involves sealing a cochlear implant lead insertion site at the round window or another location on the cochlea. By using the improved instrumentation described herein, whether the formulation has been sufficiently delivered to seal the cochlear implant lead insertion site can be verified under direct visualization. In addition, after the formulation has been administered, direct visualization can be used to verify that the formulation is retained in the desired position and manner.

Fourth, the systems and methods described herein allow direct access to the middle ear cavity through the tympanic membrane in a suture-less, low impact manner. In some implementations, such direct access through the tympanic membrane using a set of side-by-side shafts fixed to an instrument handle can be safer, less invasive, and achieved with no sealing or patching of the tympanic membrane. For example, due to the small size of the side-by-side shafts in some examples described herein, the tympanic membrane can heal naturally after withdrawal of the shafts.

Fifth, the systems and methods described herein can advantageously provide improved comfort and ease-of-use for a clinician both during the insertion of an instrument into the ear and during the actuation for delivery of the therapeutic formulation to the targeted site in the middle or inner ear. In particular examples, the systems and methods can include a handheld instrument including a handle configured to be gripped in a manner that provides enhanced dexterity and control for the user and that provides an improved size relative to the distal extending shaft(s) that extend from the handle. Optionally, the user can controllably retain the handheld instrument in a precise and preferred position using a first hand (e.g., with a pencil grip upon the handle) while separately acting upon an actuator (e.g., using a second hand) to achieve controlled delivery of the therapeutic formulation to the targeted site along the cochlea.

Sixth, the systems and methods described herein can include a disposable delivery tool that does not require sterilization for reuse. For example, in particular embodiments, the delivery tool can be a one-time-use instrument that is readily discarded while other components (such as the display controller or other structures connected to the delivery tool) are reused with subsequent delivery tools in subsequent surgical procedures. In such examples, the fluid delivery shaft of the delivery tool can be attached with the handle but need not evacuate all of the therapeutic formulation from the interior of the shaft into the patient's ear. Rather, the user may deposit only the amount that is sufficient within the user's ear, and an undelivered portion can remain in the interior of the fluid delivery shaft (connected to the handle) for safe and sanitary discarding of all such elements. Such a solution can be particularly effective, for example, where the therapeutic formulation is a self-gelling composition, and the undelivered amount remaining in the interior of the fluid delivery shaft (connected to the handle) may form a gel or harden. According to some embodiments detailed below, the entire delivery tool can be promptly discarded (e.g., including the handle, both shafts, the tip-mounted camera device, and the undelivered portion of the therapeutic formulation within the fluid delivery shaft), thereby advantageously eliminating the need to clean or remove such gel or hardened material from the interior of the fluid delivery shaft. Moreover, such disposable embodiments described herein can improve patient safety because a one-use tool can be thoroughly sterilized, packaged, and subsequently discarded after a single use without a need to sterilize the tool for another use. Using a disposable delivery tool can also improve ease of use by allowing the clinician to dispose of the tool.

Seventh, the systems described herein can also be used for diagnostic purposes, especially when accessing the cochlea using the improved delivery tool prior to the implantation procedure for the cochlear implant (e.g., for a pretreatment of the targeted site along the cochlea). Such uses can help in procedure planning, change site of care, and potentially improve patient outcomes.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
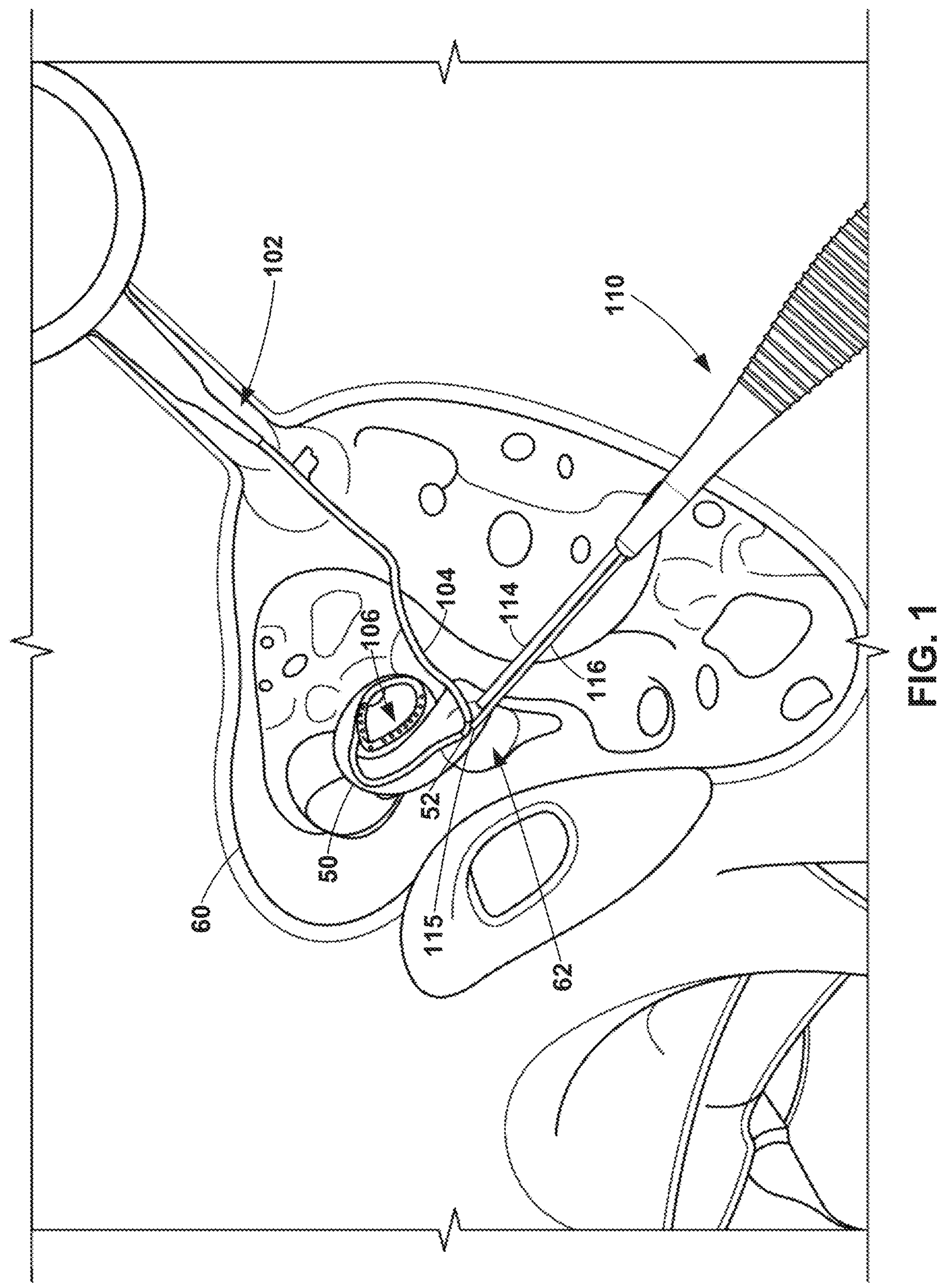
FIG. 1 is a perspective view of an ear treatment system configured to access a cochlear implant lead insertion site through a transmastoid pathway.

Referring now to FIG. 1, some embodiments of an ear treatment system 100 can be used to access a cochlea 50 of a patient 10 for purposes of delivering a therapeutic formulation at a lead insertion site along the cochlea 50. Ear treatment system 100 can include a delivery tool 110 and, optionally, a cochlear implant device 102 having a flexible lead 104 configured to extend into the cochlea 50 at the cochlear implant lead insertion site. As described in more detail below, the delivery tool 110 can be configured to deposit a therapeutic formulation, such as a self-gelling fluid that provides sustained release of a therapeutic agent, at the cochlear implant lead insertion site while also providing direct visualization of such fluid delivery. In some circumstances (detailed below), the therapeutic formulation provided by the delivery tool 110 can both provide a therapeutic treatment at the cochlear implant lead insertion site and achieve an effective seal around the lead 104 at the insertion site.

In the depicted embodiment, the cochlear implant device 102 includes the cochlear implant lead 104, which can include one or more electrodes 106 configured to extend through the cochlear implant lead insertion site (e.g., at a round window membrane 52 in this embodiment) and into the cochlea 50. It should be understood from the description herein that the cochlear implant lead 104 is not limited to entering the cochlea 50 through the round window membrane 52, and for example, the cochlear implant lead 104 may optionally extend into the cochlea 50 through a lead insertion site formed by surgical opening (e.g., a cochleostomy) in the cochlea 50 that is spaced apart from the round window membrane 52. A distal portion of the cochlear implant lead 104 can extend through the cochlea 50 in a spiral pattern, as seen in FIG. 1. The one or more electrodes 106 of the cochlear implant device 102 can deliver stimulation to the cochlea 50 in a way that stimulates a cochlear nerve of the patient.

Still referring to FIG. 1, the delivery tool 110 is configured to deliver the therapeutic formulation to the round window membrane 52 (as illustrated in FIG. 1) or another targeted site along the cochlea 50. The therapeutic formulation, in some embodiments, can seal the cochlear implant lead insertion site where the cochlear implant lead 104 enters the cochlea 50. This sealing can be part of a procedure to implant the cochlear implant lead 104. For example, a clinician can implant the cochlear implant lead 104 within cochlea 50 such that the cochlear implant lead 104 occupies the position within the cochlea 50 depicted in FIG. 1, and subsequently seal the cochlear implant lead insertion site at the round window membrane 52 using the delivery tool 110.

In some embodiments described herein, the cochlear implant 102 is implanted via a trans-mastoid approach, in which case the delivery tool 110 can advantageously and simultaneously use the same approach path to deposit the therapeutic formulation at the cochlear implant lead insertion site. For example, to deliver the cochlear implant lead 104 within the cochlea 50 via the trans-mastoid approach, a clinician can first make an incision in skin behind the patient's ear and make cuts in the mastoid bone under the incision. In some cases, the clinician can advance the cochlear implant lead 104 through the incision and across the cuts in the mastoid bone to reach the round window membrane 52. The clinician can insert the cochlear implant lead 104 through the round window membrane 52 and into the cochlea 50 so that the cochlear implant lead 104 extends internally within cochlea 50 in a spiral path as depicted in FIG. 1.

When the cochlear implant lead 104 is implanted to a sufficient depth within the cochlea 50, the delivery tool 110 can deliver the formulation to seal the cochlear implant lead insertion site at the round window membrane 52 (such that the fluid is deposited around the cochlear implant lead 104 at the insertion site where the cochlear implant lead 104 enters the cochlea 50). In some examples, the clinician can advance the delivery tool 110 to the round window membrane 52 through the same trans-mastoid access path that was made to create access to the cochlea 50 for implanting the cochlear implant lead 104. In doing so, no additional cuts or incisions are necessarily required for the delivery tool 110 to access the round window membrane 52 after the cochlear implant lead 104 is implanted.

In some cases, the therapeutic formulation delivered by the delivery tool 110 is a fluid in the form of a liquid or gel, and the targeted site is a round window membrane 52 of cochlea 50. It should be understood from the description here that, in some embodiments, the targeted site can be another location in the middle or within the inner ear. For example, delivery tool 110 can include a fluid delivery shaft that is sized to penetrate the round window membrane and deliver a therapeutic formulation directly into the cochlea, such as into the perilymph of the inner ear. Also as described in more detail below, the delivery tool 110 can be equipped with tip-mounted camera 112 fixed to a distal end of a first shaft 114, which can advantageously provide direct visualization of the delivery of the therapeutic formulation to the targeted site via a distal port 115 located at a distal end of a second shaft 116.

Still referring to FIG. 1, in use during some implementations, the clinician can readily grasp a handle of the delivery tool 110 (e.g., using a pencil grip or other grip that enhances control and accuracy) to simultaneously advance side-by-side shafts of the delivery tool 110 through a surgical opening in the mastoid bone. Under direct visualization provided by the tip-mounted camera 112 of the delivery tool, the clinician 1 can grasp the handle of the delivery tool 110 to accurately advance a distal port of the second (longer) shaft 116 toward the round window membrane of the cochlea while the tip-mounted camera 112 at a distal end of first (shorter) shaft 114 provides direct visualization of the second shaft 116. From there, while the clinician uses a first hand to retain the delivery tool 110 in its operative position (with the distal port 115 of the second shaft 116 proximate to the round window membrane and under direct visualization), the clinician 1 use a second hand to control delivery of the therapeutic formulation from the distal port 115.

Particular examples of the ear treatment system 100 described herein can be in particular methods to treat and/or prevent a variety of ear conditions, including but not limited to hearing loss (such as hidden hearing loss, noise-induced hearing loss, age-related hearing loss), drug-induced hearing loss (e.g., chemotherapy-induced hearing loss or aminoglycoside-induced hearing loss), sudden sensorineural hearing loss (SNHL), autoimmune inner ear disease, and the like, or particular disorders of the middle ear and/or inner ear (such as tinnitus, balance disorders including vertigo and Meniere's Disease, vestibular neuronitis, vestibular schwannoma, labyrinthitis, otosclerosis, ossicular chain dislocation, cholesteatoma, and middle ear infections). Additionally, as described below, the ear treatment system 100 can be used in such a manner to treat a variety of ear conditions while also providing enhanced comfort to the clinician and real-time direct visualization during delivery of the treatment in the middle or inner ear.

Figure 2A:
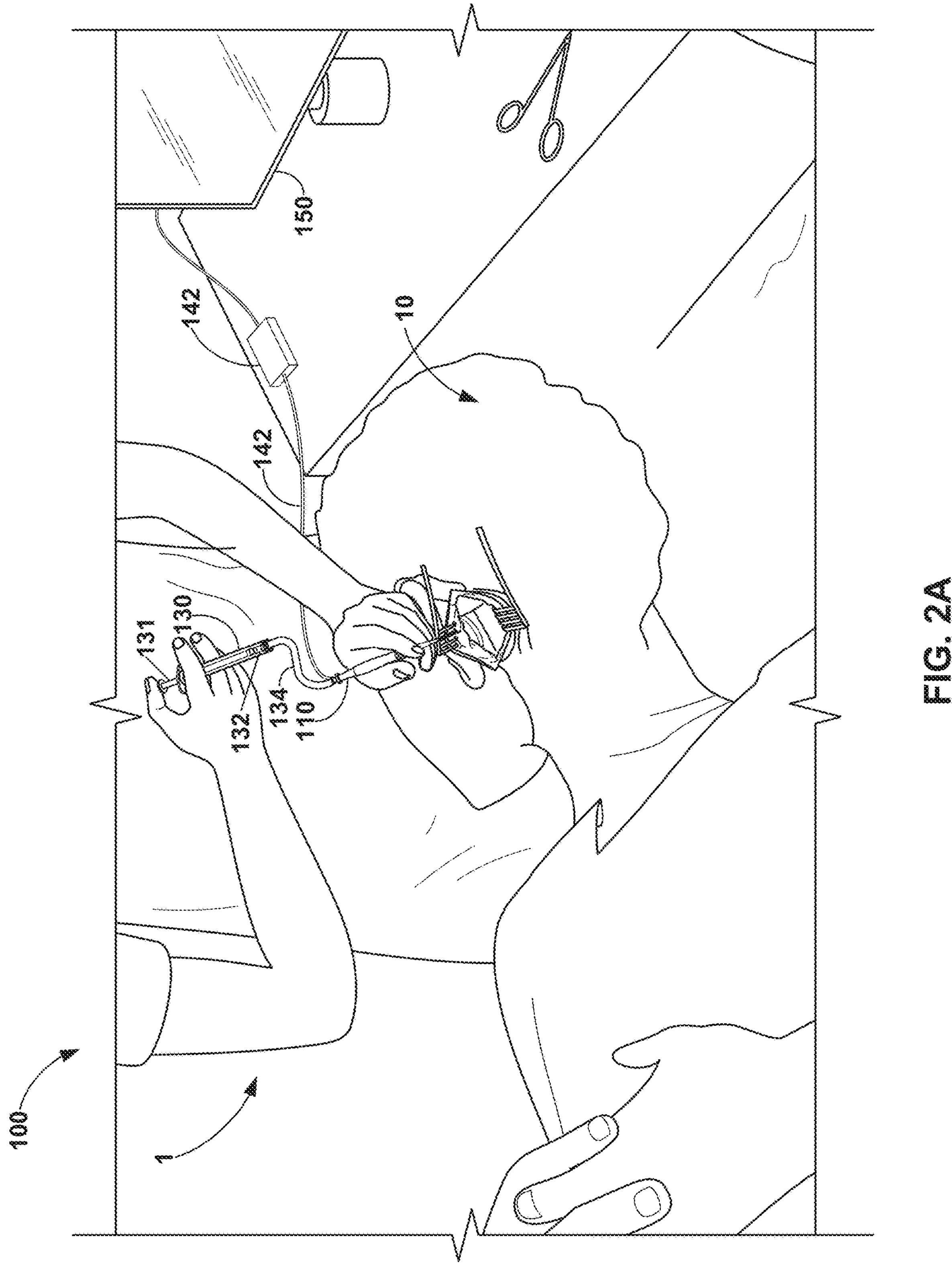
FIG. 2A is a perspective view of the ear treatment system of FIG. 1, in accordance with an example use with a patient, where access is through the transmastoid pathway.
Figure 2B:
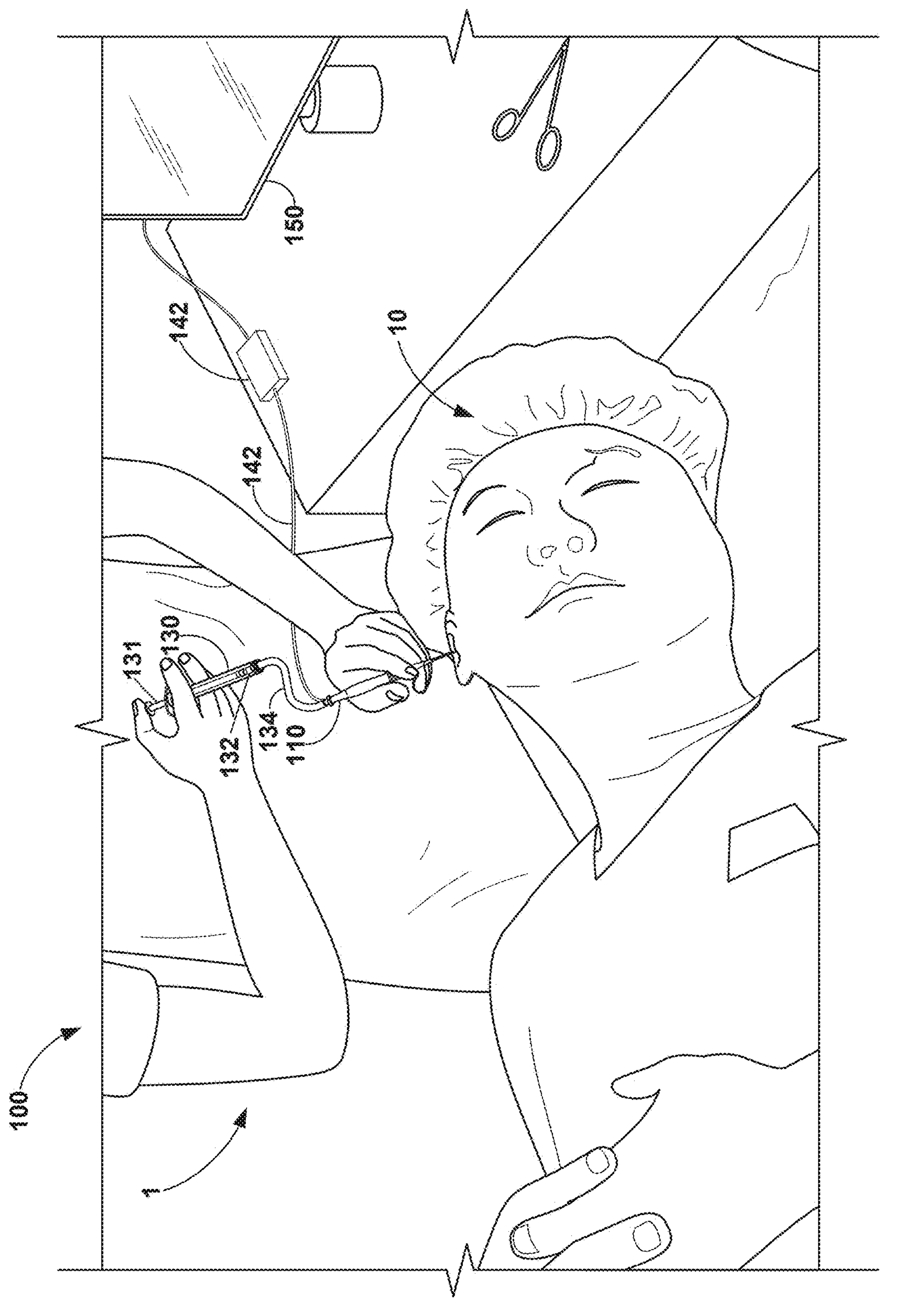
FIG. 2B is another perspective view of the ear treatment system of FIG. 1, in accordance with an example use with a patient, where access is through a transcanal pathway.
Figure 3:
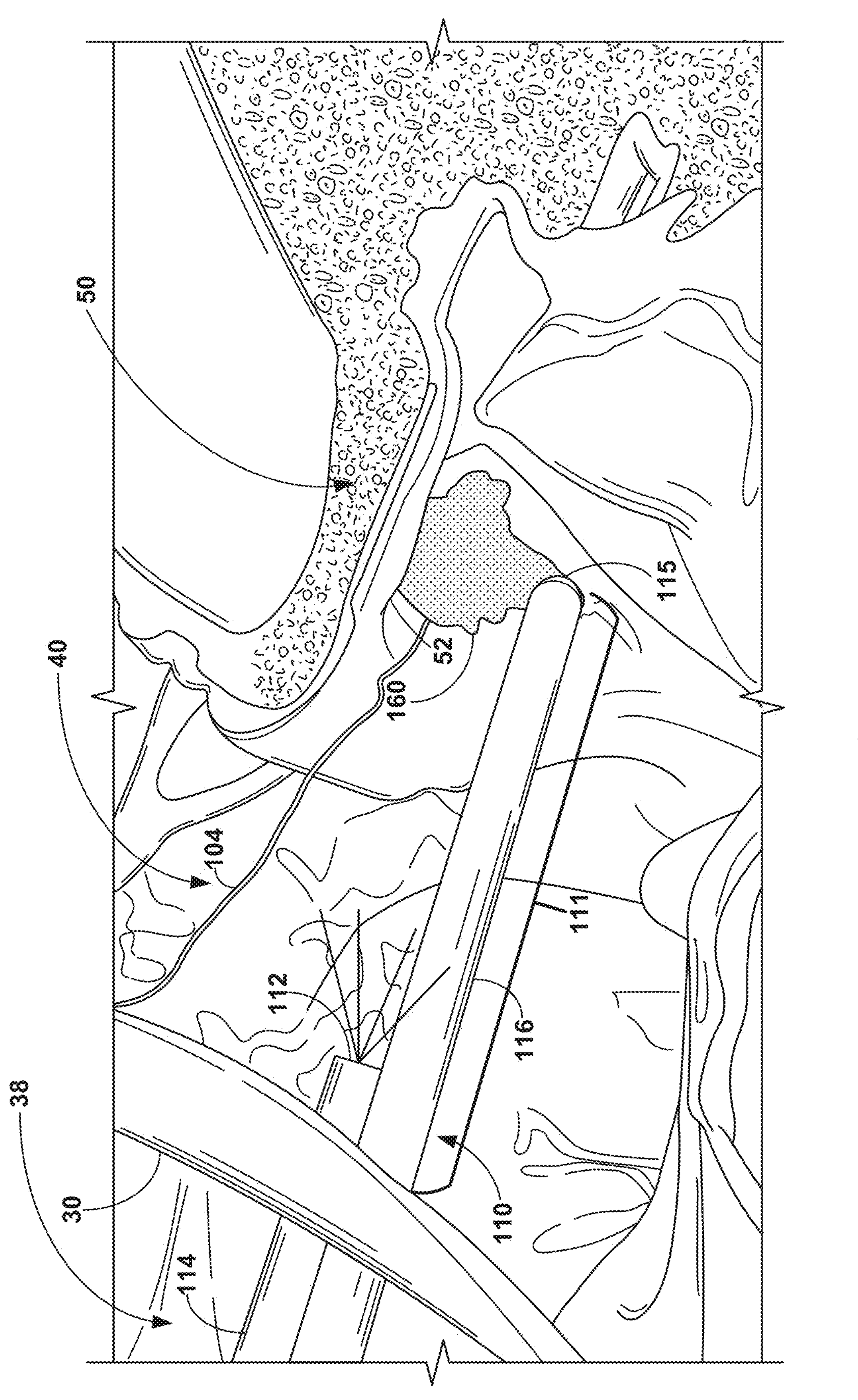
FIG. 3 is a perspective view of a distal portion of a delivery tool of the ear treatment system of FIG. 1, in accordance with some embodiments configured transcanal access toward a targeted site in the middle or inner ear.

Referring now to FIG. 1-3, the delivery tool 110 in the ear treatment system 100 can include a combination of structures that are sized in a manner that is particularly suited for the anatomy of the ear. For example, the delivery tool 110 can be sized to access the middle ear of the patient 10 through one or more transmastoid openings such as a hole 62 in the mastoid bone 60. Additionally, or alternatively, the delivery tool 110 can be sized to access the middle ear of patient 10 using a transcanal approach through ear canal 38 and across the tympanic membrane 30. This means that the delivery tool 110 can be sized to access the cochlea 50 during certain procedures that use transmastoid access (such as a procedure to insert a cochlear implant lead 104 in the cochlea 50 of the patient 10) and also can be sized to access the cochlea 50 noninvasively through the ear canal 38.

In some examples, to create a pathway to access the middle ear through the mastoid bone 60 during a procedure to deliver a cochlear implant lead 104, the patient 10 can be positioned so as to orient the ear upwardly toward the clinician 1. The patient 10 can be placed under general anesthesia. The clinician 1 can make a retroauricular incision behind an ear of the patient 10 and retract the skin and soft tissue to expose the mastoid bone 60. Next, the clinician 1 can perform a mastoidectomy, which involves drilling into the mastoid bone using a surgical drill. This drilling exposes the air cells, which are honeycomb-like structures within the mastoid bone 60. This can create one or more holes (e.g., hole 62) through the mastoid bone 60 which serve as a pathway to the middle ear of the patient 10. When creating these holes in the mastoid bone 60, the clinician 1 can avoid striking important anatomical structures such as the facial nerve and the sigmoid sinus.

When these holes are drilled in the mastoid bone 60, this can expose the middle ear of the patient 10 including the incus bone, the cochlea 50, the round window membrane 52, and the oval window. This allows the clinician 1 to insert the cochlear implant lead 104 into the cochlea 50 through round window membrane 52. When the cochlear implant lead 104 is inserted into the cochlea 50, the clinician 1 can advance delivery tool 110 into the inner ear through the hole 62 in the mastoid bone 60. For example, the delivery tool 110 can be manipulated by the clinician 1 as a handheld instrument having first and second shafts 114, 116 that are contemporaneously advanceable through the hole 62 in the mastoid bone 60 and toward the cochlea 50 of the patient 10. As depicted in FIG. 2, the patient 10 can be positioned so as to orient the mastoid bone 60 upwardly toward the clinician (and preferably so that the round window membrane 52 of the cochlea 50 can be positioned below a distal port 115 of the delivery tool 110 such that the therapeutic fluid is deposited and remains at the round window membrane 52). In some cases, the therapeutic fluid that is deposited at the round window membrane 52 seals a cochlear implant lead insertion site at the round window membrane 52 where the cochlear implant lead 104 enters the cochlea 50.

In some examples, the delivery tool 110 is advanceable to the round window membrane 52 of the cochlea 50 through the hole 62 in the mastoid bone 60 without the clinician 1 making any additional cuts or enlarging any existing cuts to accommodate delivery tool 110. That is, delivery tool 110 can use existing passageways that were created to deliver the cochlear implant lead 104 without needing any additional surgical cuts to reach the cochlea 50. For example, delivery tool 110 can be sized so that its handle and shafts 114, 116 fit through the hole 62 such that the distal port 115 is adjacent the round window membrane 52. This allows the clinician 1 to deliver the therapeutic formulation to seal the cochlear implant lead insertion site at the round window membrane 52 without making any additional cuts.

The delivery tool 110 is also particularly suited for a minimally invasive approach to access the middle ear 40 through the tympanic membrane 30. For example, as seen in FIG. 3, the delivery tool 110 can be manipulated by the clinician 1 as a handheld instrument having first and second shafts 114, 116 that are contemporaneously advanceable through an external ear canal 38, through the tympanic membrane 30, and toward the cochlea 50 of the patient 10. As depicted in FIGS. 2B and 3, the patient 10 can be positioned so as to orient the external ear canal 38 upwardly toward the clinician 1 (and preferably so that the round window membrane 52 of the cochlea 50 can be positioned below a distal port of the delivery tool 110 such that the therapeutic fluid is deposited and remains at the round window membrane 52).

The trans-tympanic access in the embodiment depicted in FIGS. 2B and 3 is minimally invasive and can avoid large, irreparable openings or tears in the tympanic membrane 30. The tympanic membrane 30, sometimes referred to as the eardrum, represents a thin membrane that separates the external ear canal 38 from middle ear 40. Tympanic membrane 30 plays a role in transmission of sound. When sound waves enter the external ear canal 38, the sound waves cause tympanic membrane 30 to vibrate, thus transmitting the vibrations to middle ear 40. The vibration frequency of tympanic membrane 30 may correspond to a frequency of the sound waves entering the external ear canal 38. Middle ear 40 is a space between tympanic membrane 30 and the inner ear. As described in more detail below, a distal portion 111 of the delivery tool 110 that is inserted through the tympanic membrane 30 (e.g., the side-by-side shafts 114, 116 depicted in FIG. 1 and FIG. 3) can have a maximum lateral width that is reduced to achieve a minimally invasive access that promotes self-healing of the tympanic membrane. For example, a needle puncture is generally less invasive than a larger surgical incision. Delivery tool 110 can be sized to perform a procedure deliver a formulation to a targeted site in an ear of the patient 10 in a way that is more like a needle puncture than a surgical incision, thus limiting an invasiveness of the procedure.

The middle ear and inner ear regions are positioned internally to the tympanic membrane 30 (opposite from the external ear canal 38). The middle ear 40 includes bones known as the ossicles such as the malleus, incus, and stapes. The ossicles amplify sound vibrations of tympanic membrane 30 and transmit these vibrations to the inner ear. The middle ear 40 is an air-filled space and is not necessarily filled with fluid. The inner ear, sometimes referred to as the labyrinth, represents a complex structure located within a temporal bone of the skull. The inner ear includes cochlea 50. Cochlea 50 contains sensory organs for detecting sound waves that cause tympanic membrane 30 to vibrate. Cochlea 50 is spiral-shaped and filled with fluid. When sound vibrations are transmitted from middle ear 40 to cochlea 50, these sound waves cause the fluid inside cochlea 50 to move. This fluid movement can stimulate hair cells of cochlea 50 that convert mechanical sound waves into electrical signals by stimulating the cochlear nerve to signal the brain of patient 10.

In some cases, the patient 10 has one or more hearing conditions that prevent the hair cells of cochlea 50 from adequately stimulating the cochlear nerve. This results in patient 10 experiencing near or total hearing loss. The patient 10 can receive a cochlear implant that is able to stimulate the cochlear nerve in response to sounds, much like a healthy ear does. This cochlear implant can include a lead 104 that extends into the cochlea 50 via the round window membrane 52, as depicted in FIG. 3. Cochlea 50 from the round window membrane 52. Round window membrane 52 may represent an opening of the cochlea 50 into middle ear 40. Round window membrane 52 may act as a pressure relief valve for cochlea 50, allowing for a displacement of fluid and the maintenance of proper pressure levels within cochlea 50. When sound waves enter cochlea 50, mechanical vibrations associated with the sound waves cause vibrations in the fluid, which stimulate the hair cells responsible for auditory perception. Round window membrane 52 helps ensure that these mechanical vibrations occur without causing excessive pressure buildup within cochlea 50, thus preserving a sensitivity of the auditory system.

Delivery tool 110 can, in some examples, be sized to access round window membrane 52 using one or both of the transmastoid approach depicted in FIGS. 1 and 2A and the transcanal approach depicted in FIGS. 2A and 3. Both of these approaches can involve the Delivery tool 110 depositing a therapeutic formulation at the round window membrane 52. Each of the approaches can be used in different scenarios. For example, the transmastoid approach can be used to deposit a therapeutic formulation at round window membrane 52 when transmastoid openings are already exposed to deliver the cochlear implant lead 104, and the transcanal approach can be used to deposit the therapeutic formulation at round window membrane 52 when transmastoid openings to the middle ear do not already exist for another reason. This is because creating a transmastoid opening such as hole 62 involves an invasive procedure where the patient 10 is placed on general anesthesia and clinician 1 makes cuts in the patient's skin and bone. It is advantageous for delivery tool 110 to use these transmastoid openings only when they exist for another reason, because delivery tool 110 is also sized for a noninvasive approach where the delivery tool 110 reaches the cochlea 50 through the ear canal 38 and the tympanic membrane 30.

Referring now to FIGS. 2A-2B, the patient 10 is depicted in an example suitable position and orientation to receive the procedure(s) to treat hearing loss and other ear disorders as described herein. In some cases, a procedure can be performed with the patient 10 fully supine as shown in FIGS. 2A-2B or reclined in a chair. The clinician 1 is configured to operate delivery tool 110 and treatment actuator device 130 to deliver the formulation to patient 10 while the patient 10 is in the example position illustrated in FIGS. 2A-2B.

For example, as shown in FIGS. 2A-2B, clinician 1 can grip delivery tool 110 with one hand and grip treatment actuator device 130 with another hand. Clinician 1 can proceed to advance delivery tool 110 into the ear of patient 10. As described above, delivery tool 110 comprises side-by-side shafts 114, 116 that advance simultaneously into the ear. The first shaft 114 can include a tip-mounted camera 112 on a distal tip that provides direct visualization of the second shaft 116 relative to anatomical features of the ear. This tip-mounted camera 112 can provide real-time image data via image data cable 142. Display controller 140 receives the image data and outputs the image data for display by a screen of display device 150. In some embodiments a latency between tip-mounted camera 112 capturing the image data and display device 150 displaying the image data is less than 10 milliseconds (ms). This means that by viewing the screen of display device 150 while operating delivery tool 110, clinician 1 can see whether delivery tool 110 is placed to deliver the formulation to the targeted site in the ear of patient 10.

With the direct visualization of second shaft 116 relative to anatomical features of the ear, clinician 1 can control treatment actuator device 130 to deliver the formulation to the targeted site when distal port 115 of second shaft 116 is located proximate to the targeted site such as round window membrane 52. The direct visualization provided by tip-mounted camera 112 can in some embodiments include a view of the formulation as it is being delivered and after it is delivered. This means that clinician 1 can view the real-time image data displayed by the screen of display device 150 to determine whether delivery tool 110 is placed to deliver the formulation and to determine whether the formulation is properly delivered at a location proximate the targeted site. When the formulation is delivered, clinician 1 can withdraw delivery tool 110 from the ear of patient 10.

During a procedure to deliver the formulation, the head of the patient 10 can be rotated to between about 30 to 45 degrees away from the clinician 1 toward the opposite ear of the patient 10. The jaw of the patient 10 can be slightly elevated, and/or the external portion of the ear of the patient 10 may be pulled superiorly and backward to adjust the canal aperture and angularity. As such, the round window membrane 52 of the patient will be oriented generally upward (e.g., away from the ground) so that, upon dispensation of the formulation from the delivery tool, the formulation is able to pool at the round window membrane 52 and not flow toward the eustachian tube or the ossicular chain.

In implementations where delivery tool 110 uses a transmastoid approach to access the middle ear 40 such as the implementation depicted in FIGS. 1 and 2A, the patient 10 is under general anesthesia during the procedure. In implementations where delivery tool 110 accesses the middle ear 40 through the hole 62 such as the implementation depicted in FIGS. 2B and 3, the patient 10 remains awake during the procedure. That is, the procedure can be performed using a local anesthetic rather than a general anesthetic. For example, in some cases agents such as phenol or lidocaine can be applied to the tympanic membrane 30 as a local anesthetic to facilitate the procedure. One reason that using local anesthetic instead of general anesthetic is possible is because in some embodiments delivery tool 110 is sized to traverse tympanic membrane 30 via a small needle puncture and does not require a larger incision to cross tympanic membrane 30. Needle punctures can be minimally invasive and do not cause a great enough level of pain such that general anesthetic is necessary. In some cases, the patient 10 can be given general anesthesia for the procedure.

Referring to FIG. 1-2B, a clinician 1 may grip delivery tool 110 with one hand and grip treatment actuator device 130 with another hand to deliver the formulation to the targeted site of patient 10. Optionally, clinician 1 may grip delivery tool 110 with a dominant hand and grip treatment actuator device 130 with a non-dominant hand, but this is not required. As shown in FIGS. 2A-2B, the handle of delivery tool 110 has an axial length and gripping region that provides enhanced comfort when the clinician grasps it using a "pencil grip" (e.g., in a space between the thumb and the index finger) that achieves precise control over the movements. Delivery tool 110 is sized and shaped to be gripped equally effectively by the right hand or the left hand. Treatment actuator device 130 is also sized and shaped to be gripped equally effectively by the right hand or the left hand.

In this embodiment, the treatment actuator device 130 is a syringe device that includes a plunger actuator 131, a fluid reservoir 132 (containing the therapeutic fluid), and a flexible tube 134 that extends distally toward a Luer connector at a proximal end of the delivery tool 110. Thus, as depicted in FIGS. 2A-2B, the clinician 1 can adjust the plunger actuator 131 to urge the therapeutic formulation along a fluid path extending between the fluid reservoir 132 and the distal port 115 at a distalmost end of the second shaft 116 of delivery tool 110. Optionally, the fluid path is fully primed prior to advancement of the delivery tool 110 into the ear such that therapeutic fluid is already located in the second shaft 116 of the delivery tool 110 and ready for dispensation upon further actuation of the plunger actuator 131.

In some embodiments, the plunger actuator 131 is configured to advance distally along a longitudinal axis of treatment actuator device 130. As the plunger actuator 131 advances distally, a volume capacity of fluid reservoir 132 decreases. By decreasing the volume capacity of fluid reservoir 132, plunger actuator 131 forces the formulation along the fluid path extending between the fluid reservoir 132 and the distal port 115. As described above, the fluid path can be fully primed prior to advancement of the delivery tool 110 into the ear. This means that forcing formulation out of the fluid reservoir 132 displaces formulation already downstream in the fluid path to deliver the formulation to the targeted site via the distal port 115.

As depicted in FIGS. 2A-2B, the clinician 1 can monitor the direct visualization (via the tip-mounted camera in connection with the display device 150) to identify when the distal port 115 of the delivery tool 110 is positioned to adjacent to or otherwise above (gravitationally) the targeted site of patient 10, and then the clinician 1 can actuate the plunger actuator 131 of treatment actuator device 130 to urge delivery of the therapeutic formation from the distal port 115 for deposition at the targeted site.

In some cases, treatment actuator device 130 is not rigidly attached to the delivery tool 110, thereby permitting the clinician 1 to accurately maintain a stationary position of the delivery tool 110 even when applying a force or other manual manipulation to the treatment actuator device 130. For example, delivery tool 110 and treatment actuator device 130 are attached to either end of flexible tube 134. Delivery tool 110 and treatment actuator device 130 can be positioned so that there is slack in flexible tube 134. When there is slack in flexible tube 134, treatment actuator device 130 can move without displacing delivery tool 110 from a stationary position. This improves an ability of clinician 1 to operate delivery tool 110 using one hand and treatment actuator device 130 using another as compared with medical device systems that include a treatment actuator device rigidly attached to a delivery tool.

As previously described, in this embodiment, the flexible tube 134 of the treatment actuator device 130 includes a Luer lock for removably mating with a Luer connector mounted to the proximal end of delivery tool 110. For example, the distal end of the flexible tube 134 can include a first (female) fitting with internal threads, and the Luer connector at the proximal end of the delivery tool 110 can include a second (male) fitting with external threads to match the internal threads of the first fitting. The first fitting receives the second fitting such that the external threads engage with the internal threads to form a sealed connection. This tight seal prevents leakage of fluid from the Luer lock connection. The connection between flexible tube 134 is not limited to examples where flexible tube 134 includes a male and delivery tool 110 includes a female fitting. In some embodiments, flexible tube 134 includes a female fitting and delivery tool 110 includes a male fitting.

It should be understood from the description herein that, in other embodiments, the delivery tool 110 and the flexible tube 134 are not limited to a Luer lock connection. For example, the delivery tool 110 and the flexible tube 134 can be connected to one another using other threaded connections, snap-fit connections, barbed connections, compression fittings, adhesive bonding, welding or fusion bonding, and bayonet connections. In any case, delivery tool 110 and flexible tube 134 are connected so that a lumen of flexible tube 134 and a lumen of delivery tool 110 form a single fluid path for delivering a formulation to a targeted site in the ear of patient 10.

Referring now to FIG. 3, the delivery tool 110 can be equipped with a tip-mounted camera 112 configured to provide real-time imaging of a second shaft 116 and surrounding anatomy within the ear. Distal port 115 located at distalmost end of second shaft 116 may, in some examples, deliver a formulation 160 to the targeted site of patient 10. This means that tip-mounted camera 112 can provide direct visualization by capturing the location of the distalmost end of second shaft 116 relative to one or more anatomical regions of the ear of patient 10. This allows clinician 1 to control the treatment actuator device 130 to deliver the formulation 160 at a select time when the distal port 115 of delivery tool 110 is accurately positioned proximate the targeted site within the ear of patient 10. As described in more detail below, the tip-mounted camera 112 can include an image capture device such as a CMOS image sensor that provides a camera-on-a-chip construction having a width of less than 1.5 mm, and preferably 1 mm or less) mounted at a distal end of second shaft 116 of the delivery tool 110.

Such a CMOS camera mounted at the tip of the delivery tool 110 can advantageously reduce the overall combined size of the shafts 114, 116 that pass through the tympanic membrane 30 as compared with tools that use an endoscope to provide direct visualization (FIG. 3). This is because an endoscope lens mounted at the end of an endoscope cannula can have a diameter that is greater than a width of the image sensor of the CMOS camera mounted on the distal tip of the first shaft 114. This means that including a CMOS camera at the distal tip of the first shaft 114 instead of an endoscope lens can result in first shaft 114 having a diameter that is smaller than a width of a comparable endoscope cannula. Tip-mounted camera 112 is not limited to including a CMOS camera. In some embodiments, tip-mounted camera 112 can include an image capture device other than a CMOS camera. For example, in some alternative options, tip-mounted camera 112 can include an optical coherence tomography (OCT) image capture device.

Optionally, the delivery tool 110 also includes a light-emitting diode (LED) mounted on a distal tip of first shaft 114 adjacent to the CMOS camera to provide illumination within the middle ear toward the distal port of the delivery tool 110. In such embodiments, the CMOS camera may include an image sensor comprising an array of light-sensitive pixels arranged on a semiconductor chip. When light reaches the image sensor, each pixel converts the light into an electrical signal proportional to an intensity of the light at the pixel. The sensor captures an image indicating the intensity at each pixel. Optionally, tip-mounted camera 112 includes a lens to focus light onto the image sensor of the CMOS camera.

Tip-mounted camera 112 can include circuitry for generating image data based on optical signals received by the image sensor. The circuitry configured to generate the image data may, in some cases, be part of the image sensor of the CMOS camera mounted at the distal tip of the delivery tool 110. In other cases, the circuitry configured to generate the image data is separate from the image sensor. In some examples, to generate the image data, the circuitry generates, for each image frame of a sequence of image frames, an intensity value for each pixel of the array of light-sensitive pixels.

Tip-mounted camera 112 can, in some implementations, output image data to display controller 140 via image data cable 142. Display controller 140 can be configured to connect with the image data cable 142 and convert the image data to another output, such as a USB, HDMI or display port connection that is then output the display device 150. In some examples, display controller 140 causes display device 150 to display the image data in real time so that clinician 1 has real time visualization of the location of delivery tool 110 relative to anatomical landmarks within the ear of patient 10. This allows clinician 1 to determine whether delivery tool 110 is properly positioned prior to dispensing the therapeutic formulation 160 to the targeted site of patient 10. In some examples, display controller 140 can include multiple output ports for connection to a variety of different types of display devices 150, such as connections to television, a computer monitor, a smart phone, a laptop, a or a tablet computer. In some examples, display controller 140 includes an input port that can connect to and disconnect from image data cable 142. Display controller 140 can connect to and disconnect from more than one delivery tool 110.

Still referring to FIG. 3, distal portion 111 of delivery tool 110 can be inserted through tympanic membrane 30 into middle ear 40. Distal portion 111 includes a portion of first shaft 114 that includes a tip-mounted camera 112 and a portion second shaft 116 that includes distal port 115 configured to deliver the formulation 160 to the targeted site. This means that distal port 115 can be positioned to deliver the formulation 160 to a targeted site of cochlea 50 as tip-mounted camera 112 provides direct visualization. Tip-mounted camera 112 can output image data indicating the location of the delivery tool 110 relative to anatomical features of the ear of patient 10 such as the round window membrane 52. Based on this relative location of the distal portion of delivery tool 110, clinician 1 can operate plunger actuator 131 of treatment actuator device 130 to deliver the formulation 160.

The therapeutic formulation 160 that is deposited onto the round window membrane 52 of the cochlea 50 can include at least one active agent configured to transfer passively by diffusion across the round window membrane 52, according to a concentration gradient, and into the perilymph within the cochlea 50. Therapeutic formulation 160 can be a self-gelling material. As such, the formulation 160 that is delivered adjacent to the round window membrane can thereafter reside adjacent to or within the round window membrane 52 as a semi-solid gel substance. As a gel substance, the delivery of the formulation 160 will remain in the targeted site at the cochlea 50 so that the formulation 160 can gradually release its active ingredient for an extended period of time such as days, weeks, or even months. Formulation 160 may ensure stability, bioavailability, and compatibility with the delicate structures of the inner ear.

After the delivery of the therapeutic formulation 160, the delivery tool 110 can be removed from the patient 10. The therapeutic formulation 160 (e.g., in gel form) will remain at the targeted site in the cochlea 50 to provide extended therapeutic effects by a controlled, sustained release of the active ingredient into the body of the patient 10. Sustained release can encompass the release of effective amounts of an active ingredient of the formulation 160 for an extended period of time. The sustained release may encompass first order release of the active ingredient, zero order release of the active ingredient, or other kinetics of release such as intermediate to zero order and first order, or combinations thereof. The sustained release may also encompass controlled release of the active ingredient of the formulation via passive molecular diffusion driven by a concentration gradient across a membrane or porous structure.

When delivery tool 110 delivers formulation 160, formulation 160 can be absorbed through the round window membrane and distributed within cochlea 50, where the formulation exerts therapeutic effects. The formulation may target specific structures within the cochlea, such as hair cells or sensory neurons, depending on the nature of the treatment. Once inside the cochlea 50, formulation 160 can treat a range of conditions or symptoms, including sensorineural hearing loss, tinnitus, or inner ear disorders. By delivering formulation 160 directly to the round window membrane, delivery tool 110 can provide trans-tympanic membrane therapy that achieves higher local concentrations and enhances therapeutic outcomes as compared with systems that do not deliver therapy directly to the round window membrane.

The procedure for delivering the formulation into the cochlea 50 of the patient 10 can be repeated periodically as needed for a particular patient's treatment. For example, in some cases deliveries of the formulation can be administered about every three to 24 months, each time using new delivery tools as described herein. In particular cases, an assessment of the patient 10 can be performed to determine whether or when to administer more formulation. In some cases, a procedure such as magnetic resonance imaging (MRI) (or other type of procedure) can be performed to help make such an assessment.

Figures 4, 5, 6:
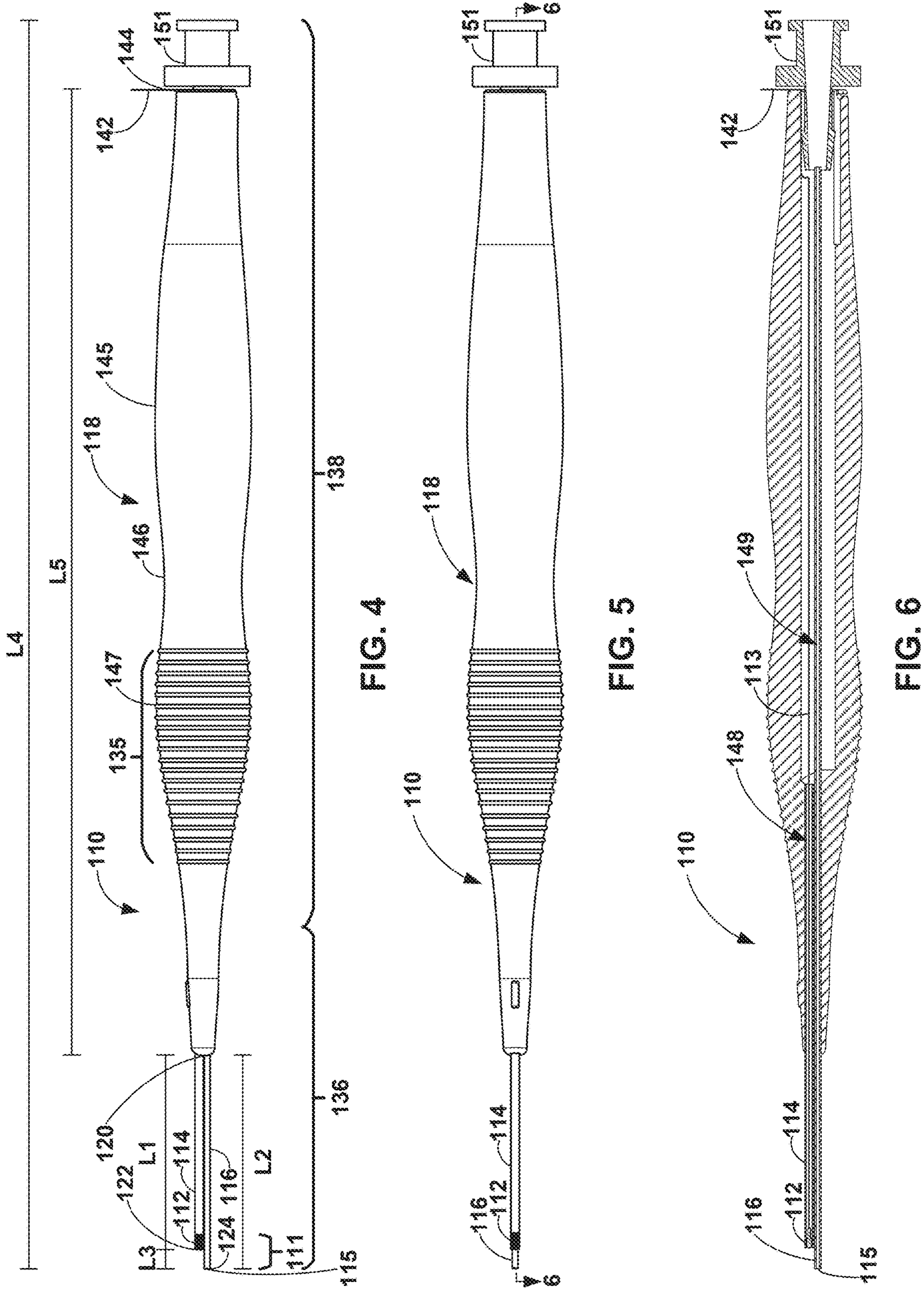
FIG. 4 shows a first side view of the delivery tool of the ear treatment system of FIG. 1.
FIG. 5 shows a top side view of the delivery tool of FIG. 4.
FIG. 6 shows a cross-sectional view of the delivery tool of FIG. 4.

Referring now to FIG. 4-6, an example delivery tool 110 can be used to perform the procedure to treat hearing loss and other ear disorders as described herein. As illustrated in FIG. 4-6, delivery tool 110 includes tip-mounted camera 112, first shaft 114, second shaft 116, and handle 118. Handle 118 receives first shaft 114 and second shaft 116 through a distal opening 120 of handle 118.

As described above, delivery tool 110 is configured to deliver a formulation to a targeted site in an ear of patient 10. A portion of delivery tool 110 is inserted into the ear of patient 10 to deliver the formulation. Since the human ear forms several small caverns, passageways, and openings, delivery tool 110 can be sized to access these areas and successfully deliver the formulation. Delivery tool 110 is also sized to be gripped and maneuvered by clinician 1 during a procedure to deliver the formulation. Physical dimensions and aspects of delivery tool 110 allow delivery tool 110 to advance into the ear of patient 10 to deliver the formulation to the targeted site through a minimally invasive approach. For instance, the physical dimensions of delivery tool 110 allow delivery tool 110 to advance to the targeted site using at least two different approaches. These approaches include a "transmastoid" approach where delivery tool 110 extends to the targeted site through one or more surgical openings (e.g., hole 62) in the patient's mastoid bone 60 and a "transcanal" approach where delivery tool 110 extends through the patient's ear canal 38 and across the tympanic membrane 30 to reach the targeted site. Because delivery tool 110 is sized to use both of these approaches to reach the targeted site, clinician 1 can use whichever approach is most beneficial under given circumstances.

In some embodiments, delivery tool 110 can provide transmastoid access to middle ear 40 when a pathway to middle ear 40 exists through the mastoid bone 60 of the patient 10. For example, delivery tool 110 can deliver a therapeutic formulation to a cochlear implant lead insertion site on cochlea 50 during a procedure to deliver a cochlear implant lead 104 to the cochlea 50 of patient 10. In some examples, the cochlear implant lead insertion site can include a round window membrane 52 or another opening (e.g., a cochleostomy) in cochlea 50. Cochlear implant lead 104 can be sized to extend into the cochlea 50 through round window membrane 52. During a procedure to deliver cochlear implant lead 104, the patient 10 can be under general anesthesia. Clinician 1 can make an incision behind the patient's ear and pull back the skin to expose the mastoid bone 60. The clinician 1 can drill into the mastoid bone to create one or more holes (including hole 62) that expose the middle ear 40. The clinician 1 can advance the cochlear implant lead 104 into the cochlea 50 through the one or more holes in the mastoid bone 60.

When the cochlear implant lead 104 is inserted within the cochlea 50 through round window membrane 52 and before the holes (e.g., hole 62) in the mastoid bone 60 are closed, delivery tool 110 can access the middle ear 40 through the one or more holes in the mastoid bone 60. For example, when delivery tool 110 accesses middle ear 40 through a hole 62 in the mastoid bone 60, a body of delivery tool 110 is sized to pass through hole 62 without the clinician 1 enlarging the hole 62 by cutting the mastoid bone 60. This means that delivery tool 110 can use existing surgical openings to access the middle ear 40 without clinician 1 needing to create any additional surgical openings or otherwise perform additional surgical cuts. In some cases, delivery tool 110 can deliver a therapeutic formulation to the targeted site, such as the location where cochlear implant lead 104 enters cochlea 50. The therapeutic formulation can seal the location where cochlear implant lead 104 enters cochlea 50 as part of the procedure to deliver cochlear implant lead 104.

In some examples where delivery tool 110 accesses the middle ear 40 through the mastoid bone 60, the delivery tool 110 bypasses tympanic membrane 30 to reach the round window membrane 52. That is, delivery tool 110 does not need to cross an incision in tympanic membrane 30 as delivery tool 110 does when accessing the middle ear 40 through ear canal 38 (e.g., transcanal access). In some cases, a diameter of the hole 62 in the mastoid bone 60 is larger than a diameter of the incision in tympanic membrane 30 that delivery tool 110 uses during transcanal access. This means that delivery tool 110 can fit through the hole 62 in the mastoid bone 60 more easily than the delivery tool 110 can fit through the incision in the tympanic membrane 30.

In some embodiments, delivery tool 110 can provide trans-tympanic membrane access to middle ear 40 and round window membrane 52. This trans-tympanic membrane access can also be referred to as "transcanal" access because delivery tool 110 can extend through ear canal 38 and across the tympanic membrane 30 to access the middle ear 40. Trans-tympanic membrane therapy delivery to middle ear 40, specifically targeting the round window membrane, can involve administering medication or therapeutic agents directly into middle ear 40 through round window membrane 52 of cochlea 50. Delivery tool 110 can access middle ear 40 via a small puncture in tympanic membrane 30 while patient 10 is under local anesthesia. In some implementations, a size of this small puncture is more similar to a size of a needle puncture than to a size of a surgical incision made with a scalpel. This means that when delivery tool 110 accesses middle ear 40 through the small puncture in tympanic membrane 30, delivery tool 110 is sized to cross the tympanic membrane 30 through the small puncture without significantly increasing the size of the small puncture and without further damaging tympanic membrane 30.

For example, distal portion 111 of delivery tool 110 can extend through the small puncture in tympanic membrane 30 and into the middle ear 40. In some embodiments, a greatest width of distal portion 111 that extends into the middle ear 40 is less than 3 mm, preferably less than 2 mm, and within a range from 1.0 mm to 1.8 mm. This means that distal portion 111 of delivery tool 110 can enter the small puncture in tympanic membrane 30 without significantly increasing a size of the small puncture, ensuring that the procedure is minimally invasive. In some embodiments, the greatest width of distal portion 111 is smaller than a greatest width of a puncture tool that creates the small puncture in tympanic membrane 30. In some embodiments, the greatest width of distal portion 111 is less than 150% of a greatest width of a puncture tool that creates the small puncture in tympanic membrane 30. As described above, the distal portion 111 of delivery tool 110 also can enter a hole 62 in the mastoid bone 60 to reach to middle ear 40. This is because a diameter of hole 62 can be greater than a width of the small puncture in tympanic membrane 30, meaning that the diameter of distal portion 111 can pass through hole 62 just as distal portion 111 passes across tympanic membrane 30.

Optionally, the distal portion 111 of the delivery tool 110 can be used as the puncture tool to achieve the trans-tympanic access (e.g., without the need for a separate puncture tool). In some embodiments, delivery tool 110 can create the small puncture in tympanic membrane 30 itself by using blunt dissection to pierce tympanic membrane 30. For example, the user can readily grasp the handle 118 (e.g., using a pencil grip or other grip that enhances control and accuracy) and advance the side-by-side shafts 114 and 116 into the outer ear toward the tympanic membrane 30. Because the distal end of the second shaft 116 extends distally of the first shaft 114 and has a small diameter (for example, less than 1.5 mm and preferably about 1.3 mm in this embodiment), the distal end of the second shaft 116 can engage the tympanic membrane to create a small pilot opening through the tympanic membrane 30. The tip-mounted camera 112 on the first shaft 114 can provide direct visualization of the distal end of the second shaft 116 during formation of the pilot opening through the tympanic membrane 30. As the handle 118 is manipulated to further advance both shafts 114 and 116, the first shaft 114 then reaches the tympanic membrane 30 and passes through the pilot opening in the tympanic membrane previously formed by the second shaft 116 (which can cause the pilot opening to dilate slightly). As such, the distal portion 11 of the delivery tool 110 can be used to safely and rapidly achieve a micro-puncture in the tympanic membrane 30 that is capable of self-healing, with the overall size of the opening in the tympanic membrane 30 being substantially the same size as the combined lateral width of the side-by-side shafts. In such examples, the opening formed in the tympanic membrane can be no greater than 2 mm, and preferably about 1 mm to about 1.8 mm.

In some embodiments, delivery tool 110 can provide access to middle ear 40 through ear canal 38 and across tympanic membrane 30 to deliver a therapeutic formulation in cases where an opening through the mastoid bone 60 is not already exposed for delivery tool 110 to enter. As described above, clinician 1 can make an incision in the patient's skin and drill hole 62 in mastoid bone 60 as part of a surgical procedure to deliver a cochlear implant lead 104. When this hole 62 is already exposed so that delivery tool 110 can access the middle ear 40, it can be advantageous for delivery tool 110 access the middle ear 40 through hole 62 because it is not necessary for delivery tool 110 to cross tympanic membrane 30 when using transmastoid access to reach the middle ear 40. On the other hand, when an opening through the mastoid bone 60 is not exposed, delivery tool 110 can use transcanal access through ear canal 38 and tympanic membrane 30 to reach middle ear 40. This approach is minimally invasive and does not require the significant cuts to tissue and bone that are part of transmastoid access.

Because delivery tool 110 is capable of both transmastoid access and transcanal access, a clinician 1 can select an approach for accessing the middle ear 40 that is least invasive in a given scenario. For example, in cases where a surgical opening through mastoid bone 60 is already open for another reason (e.g., to deliver cochlear implant lead 104), clinician 1 can select the transmastoid approach to seal the cochlear implant lead insertion site at round window membrane 52 because crossing the tympanic membrane 30 is not necessary in the transmastoid approach. In cases where a surgical opening through mastoid bone 60 is not already open for another reason (e.g., before and after the delivery of cochlear implant lead 104), the clinician 1 can select the transcanal approach because this approach does not require major surgical cuts and patient 10 does not need to be under general anesthesia.

Tip-mounted camera 112 provides direct visualization of a location of the distal end of the delivery tool 110 relative anatomical features of the ear of patient 10 during a procedure to treat hearing loss and other ear disorders as described herein. To provide direct visualization, an image sensor of tip-mounted camera 112 is located on the distal portion 111 of delivery tool 110 that extends through the small puncture in tympanic membrane 30 and into middle ear 40. This direct visualization provided by tip-mounted camera 112 allows clinician 1 to determine whether delivery tool 110 is properly positioned to deliver a formulation to the targeted site. Tip-mounted camera 112 provides direct visualization both in cases where delivery tool 110 uses the transcanal approach to access the targeted site and in cases where delivery tool 110 uses the transmastoid approach to access the targeted site.

First shaft 114 comprises an elongated member that extends from a proximal end within handle 118 to a distal end 122. Preferably, first shaft 114 is cylindrical and has a circular cross section along an entire length of first shaft 114, but this is not required. Optionally, first shaft 114 can form a shape other than a cylinder having a circular cross section. In some embodiments, an image sensor of tip-mounted camera 112 can be mounted on the distal end 122 of first shaft 114. In some embodiments, a light source of tip-mounted camera 112 such as an LED is mounted on the distal end 122 of first shaft 114.

Second shaft 116 comprises an elongated member that extends from a proximal end within handle 118 to a distal end 124. Preferably, second shaft 116 is cylindrical and has a circular cross section along an entire length of second shaft 116, but this is not required. Second shaft 116 can form a shape other than a cylinder. In some embodiments, second shaft 116 forms a lumen that extends an entire length of second shaft 116 from a proximal end of second shaft 116 to distal end 124 of second shaft 116. Second shaft 116 defines a distal port 115 for delivering the formulation to the targeted site via the lumen of second shaft 116.

Shafts 114, 116 are sized and positioned so that delivery tool 110 can effectively deliver the formulation to the targeted site as tip-mounted camera 112 provides direct visualization. For example, first shaft 114 and second shaft 116 can be fixedly attached to each other so that first shaft 114 and second shaft 116 cannot move relative to each other. Tip-mounted camera 112 can be fixedly attached to a distal portion of first shaft 114. Since first shaft 114 and second shaft 116 can be fixedly attached, this means that the image sensor of tip-mounted camera 112 does not move relative to the location of first shaft 114 and the location of tip-mounted camera 112 does not move relative to second shaft 116 in some embodiments.

Fixedly attaching first shaft 114 and second shaft 116 provides several advantages over tools that include separate delivery and imaging shafts that move relative to each other. One advantage is that a clinician can move first shaft 114 and second shaft 116 simultaneously without controlling the position of second shaft 116 relative to the position of first shaft 114. Another advantage is that because the location of tip-mounted camera 112 is fixed relative to second shaft 116, tip-mounted camera 112 can provide direct visualization of the location of second shaft 116 relative to anatomy of the ear. When first shaft 114 and second shaft 116 are fixed, direct visualization is not interrupted by tip-mounted camera 112 moving distally away from the distal end of second shaft 116 so that the distal end of second shaft 116 is not in focus or moving proximally past the end of second shaft 116 so that the distal end of second shaft 116 is behind the tip-mounted camera 112.

In some embodiments, first shaft 114 and second shaft 116 are rigid and not bendable. A passageway through external ear canal 38 and across tympanic membrane 30 is generally straight in many patients so that delivery tool 110 can advance to the targeted site without bending. This means that first shaft 114 and second shaft 116 can be generally straight members that extend along a longitudinal axis without bending relative to the longitudinal axis of delivery tool 110 during use. It can be beneficial for first shaft 114 and second shaft 116 to be rigid so that clinician 1 can operate delivery tool 110 without independently controlling first shaft 114 and second shaft 116 to bend.

Distal end 124 of second shaft 116 extends distally beyond distal end 122 of first shaft 114. This configuration helps delivery tool 110 to provide direct visualization of the location of second shaft 116 relative to anatomy of the ear. For example, tip-mounted camera 112 is placed on the distal end 122 of first shaft 114. This means that tip-mounted camera 112 can capture a portion of second shaft 116 that extends distally beyond distal end 122 of shaft 114. Delivery tool 110 can deliver a formulation to a targeted site via distal port 115 at the distal end 124 of second shaft 116. The portion of second shaft 116 that extends distally beyond distal end 122 of shaft 114 is within a field of view of tip-mounted camera 112. When distal port 115 is positioned adjacent to the targeted site, delivery tool 110 delivers the formulation to the targeted site via distal port 115.

First shaft 114 extends from distal opening 120 of handle 118 for a distance equal to length L1. Second shaft 116 extends from distal opening 120 of handle 118 for a distance equal to length L2. As shown in FIG. 4, length L2 is greater than length L1, meaning that the distal end 124 of second shaft 116 extends distally beyond distal end 122 of first shaft 114. The distance between the distal end 124 of second shaft 116 and the distal end 122 of first shaft 114 is equal to length L3.

Delivery tool 110 can be sized so that lengths L1, L2, and L3 help delivery tool 110 to perform a procedure to deliver the formulation to a targeted site within the middle ear 40 of patient 10. For example, the tympanic membrane 30 is located at an end of external ear canal 38. This means that delivery tool 110 can be sized to navigate through ear canal 38 to reach middle ear 40, located across tympanic membrane 30 at the end of external ear canal 38. Additionally, middle ear 40 is located beyond the mastoid bone 60 of the patient 10. This means that delivery tool 110 can be sized to navigate through an opening in the mastoid bone 60 to reach the middle ear 40. In some embodiments, delivery tool 110 can be sized so that tip-mounted camera 112 and distal port 115 both reach middle ear 40 when first shaft 114 and second shaft 116 simultaneously advance through tympanic membrane 30 via a needle puncture. In some embodiments, delivery tool 110 can be sized so that tip-mounted camera 112 and distal port 115 both reach middle ear 40 when first shaft 114 and second shaft 116 simultaneously advance through a hole 62 in mastoid bone 60.

A length of the external ear canal for many adult patients is within a range from 20 mm to 30 mm. In some embodiments, delivery tool 110 can be sized so that exposed portions of shafts 114, 116 extend through most of the external ear canal of many patients. This is because the external ear canal is a narrow passageway. As shown in FIG. 4-6, a combined width of shafts 114, 116 is significantly narrower than a width of handle 118. This means that delivery tool 110 is sized so that the exposed portions of shafts 114, 116 extend through most of the external ear canal. This can ensure that delivery tool 110 is able to navigate through the external ear canal to the targeted site without wider portions of delivery tool 110 being physically obstructed by walls of the external ear canal or other anatomy of the ear.

Furthermore, a distance between the mastoid bone 60 and the middle ear 40 is not more than 35 mm in many patients. This means that exposed portions of shafts 114, 116 can extend through the mastoid bone 60 to reach the middle ear 40 even when the hole 62 in the mastoid bone 60 is narrow and/or a passageway to the middle ear 40 underneath the mastoid bone 60 is narrow. Consequently, just as delivery tool 110 can reach the middle ear 40 through the narrow ear canal 38, the delivery tool 110 can also reach the middle ear 40 through the hole 62 in the mastoid bone 60. Dimensions of delivery tool 110 accommodate both of these approaches to reach the middle ear 40.

In some embodiments, the length L1 of the portion of first shaft 114 extending distally from distal opening 120 of handle 118 is within a range from 20 mm to 30 mm. Preferably, length L1 is equal to approximately 25 mm. The length L2 of the portion of second shaft 116 extending distally from distal opening 120 of handle 118 may be within a range from 22.5 mm to 33.5 mm. Preferably, length L2 is equal to approximately 27.5 mm. Length L2 is preferably greater than length L1. This means that delivery tool 110 can be sized so that the portions of shafts 114, 116 that extend from distal opening 120 of handle 118 are similar to a length of the external ear canal of many patients. Furthermore, this means that delivery tool 110 can be sized so that the portions of shafts 114, 116 that extend from distal opening 120 of handle 118 are similar to a distance between the mastoid bone 60 and the cochlea 50.

Length L3 represents a distance between distal end 122 of first shaft 114 and distal end 124 of second shaft 116. As described above, tip-mounted camera 112 can be located on the distal end 122 of first shaft 114 so that tip-mounted camera 112 captures a portion of second shaft 116 that extends distally beyond the distal end 122 of first shaft 114. In some embodiments, delivery tool 110 is sized to perform one or more tasks within middle ear 40. For example, length L3 can be sized so that tip-mounted camera 112 and distal port 115 both fit within middle ear 40 at the same time. This allows tip-mounted camera 112 to capture the location of second shaft 116 relative to a targeted site such as round window membrane 52. The length L3 can also be sized so a distalmost portion of second shaft 116 is within a field of view of tip-mounted camera 112.

In some embodiments, length L3 is within a range from 1 mm to 4 mm and preferably about 2.5 mm. When length L3 is about 2.5 mm, for example, first shaft 114 and second shaft 116 can advance simultaneously across tympanic membrane 30 so that tip-mounted camera 112 and distal port 115 are both within middle ear 40 at the same time. Since tip-mounted camera 112 is located on a distal end 122 of first shaft 114, tip-mounted camera 112 is configured to capture the distalmost portion of second shaft 116 to provide direct visualization of second shaft 116 relative to the targeted site beyond tympanic membrane 30. When the targeted site is the round window membrane, for example, delivery tool 110 having a length L3 between distal end 122 of first shaft 114 and distal end 124 of second shaft 116 allows shafts 114, 116 to move simultaneously so that distal port 115 is located adjacent the round window membrane while tip-mounted camera 112 is located within middle ear 40 to capture both second shaft 116 and the round window membrane.

Delivery tool 110 can be sized so that length L3 is compatible with a size of the middle ear 40 for many patients. For example, delivery tool 110 can be sized so that length L3 is less than a distance between the tympanic membrane 30 and round window membrane 52. When length L3 is less than a distance between the tympanic membrane 30 and round window membrane 52, this allows delivery tool 110 to advance so that tip-mounted camera 112 advances beyond tympanic membrane 30 and so that distal port 115 advances to a location adjacent round window membrane 52. In some examples, length L3 also accommodates direct visualization when delivery tool 110 accesses the middle ear 40 through a hole 62 in the mastoid bone 60.

Delivery tool 110 having shafts 114, 116 that are sized to length L1 and the length L2 allows delivery tool 110 to navigate through external ear canal 38 and traverse tympanic membrane 30 without wider portions of delivery tool 110 being obstructed by walls of the external ear canal 38 or other anatomy of the ear. For example, when the portion of first shaft 114 extending distally from distal opening 120 of handle 118 has length L1 and when the portion of second shaft 116 extending distally from distal opening 120 of handle 118 has length L2, delivery tool 110 can advance to the targeted site in the ear of patient 10 such that first shaft 114, second shaft 116, and a distal section 136 of handle 118 are within the ear of patient 10. That is, when length L1 is within a range from 20 mm to 30 mm and length L2 is within a range from 22.5 mm to 33.5 mm, the distal section 136 of delivery tool 110 can be inserted into the ear and the proximal section 138 of delivery tool 110 can remain outside of the ear. These dimensions also accommodate transmastoid access to the middle ear 40. For example, the distal section 136 of delivery tool 110 can be inserted into the hole 62 in the mastoid bone 60 so that a distal port 115 reaches round window membrane 52 while the proximal section 138 of delivery tool 110 remains outside of the ear.

First shaft 114 and second shaft 116 are positioned to allow delivery tool 110 easy access to and maneuverability within small locations of the ear of patient 10 such as external ear canal 38 and middle ear 40. In some embodiments, first shaft 114 and second shaft 116 are in contact along an entire length of first shaft 114 extending distally from handle 118. This means that along an entire length of first shaft 114 that extends distally from handle 118, a width of delivery tool 110 is equal to a sum of a width of first shaft 114 and a width of second shaft 116. In other words, there is no point along first shaft 114 extending distally from handle 118 where first shaft 114 and second shaft 116 are separated by a gap.

When there is no gap between first shaft 114 and a width of second shaft 116, this minimizes cross-sectional footprint of first shaft 114 and a width of second shaft 116 and makes first shaft 114 and second shaft 116 suited for a minimally invasive procedure to deliver a formulation. This is because first shaft 114 and second shaft 116 can simultaneously advance through a small needle puncture in tympanic membrane 30 or a small hole 62 in mastoid bone 60 when first shaft 114 and second shaft 116 are grouped closely together so that there is no space between first shaft 114 and second shaft 116. Any space between first shaft 114 and second shaft 116 could make it harder for first shaft 114 and second shaft 116 to simultaneously advance through the same needle puncture or hole in the mastoid bone.

Optionally, first shaft 114 and second shaft 116 can be separated by a small gap along an entire length of first shaft 114 extending distally from handle 118. In some examples, a width of this gap may be within a range from 0.1% to 2% of an outer diameter of first shaft 114. When a gap between first shaft 114 and second shaft 116 is small relative to a diameter of first shaft 114, this gap does not significantly add to a total cross-sectional footprint of first shaft 114 and second shaft 116. This means that first shaft 114 and second shaft 116 can advance through a needle puncture in tympanic membrane 30 or hole 62 in mastoid bone 60 in some implementations where there is a gap between first shaft 114 and second shaft 116.

As shown in FIG. 4-6, first shaft 114 and second shaft 116 are parallel along an entire length of first shaft 114 and second shaft 116 extending distally from handle 118. Since first shaft 114 and second shaft 116 are parallel, a total distance across first shaft 114 and second shaft 116 does not change along the length of first shaft 114 extending distally from handle 118. This means that delivery tool 110 can advance through the external ear canal 38 and middle ear 40 ear of patient 10 without being obstructed by the walls of external ear canal 38 or other ear anatomy. The delivery tool 110 can alternatively advance through a hole 62 in mastoid bone 60 to reach the middle ear 40 of patient 10 without being obstructed by anatomy of the patient 10. A tool having non-parallel shafts includes at least some portions where there is a gap between the non-parallel shafts. These gaps increase the total width of the tool, making it more difficult to navigate the tool in small spaces.

Because first shaft 114 and second shaft 116 are parallel, this may allow delivery tool 110 to fit within the ear more easily as compared with tools that use two shafts that are not parallel. When two shafts are not parallel, these shafts may intersect at an intersection point and grow farther apart from each other along an axis. When shafts are farther apart, this may increase a diameter of a passageway needed to accommodate the shafts. But when the shafts are parallel, this may improve an ability of the shafts to within a narrow passageway such as external ear canal 38 or the hole 62 in mastoid bone 60.

In some embodiments, first shaft 114 and second shaft 116 are not exactly parallel, and there is a small angle between a first shaft 114 and second shaft 116. In some embodiments, this angle is less than 1 degree. When the angle between first shaft 114 and second shaft 116 is small and first shaft 114 and second shaft 116 are close together, a maximum width of a gap between first shaft 114 and second shaft 116 does not significantly add to a total width of the first shaft 114 and second shaft 116 extending distally from handle 118. This allows delivery tool 110 to navigate to the targeted site.

In some embodiments, one or both of first shaft 114 and second shaft 116 comprise a polyimide material. Polyimide is a versatile polymer that exhibits high temperature resistance, mechanical strength, electrical insulation, and biocompatibility. This makes polyimide suitable for medical applications where flexibility, durability, and compatibility with the human body are beneficial. Polyimide can withstand high temperatures without significant degradation. Polyimide also exhibits mechanical properties such as high tensile strength, stiffness, and dimensional stability. Since polyimide provides electrical insulation properties, it may be beneficial for first shaft 114 to include polyimide for insulating an electrical conductor connected to tip-mounted camera 112. Because polyimide has a low coefficient of thermal expansion, it may be beneficial to use polyimide for first shaft 114 and second shaft 116 so that body heat does not change a shape and size of first shaft 114 and second shaft 116. Furthermore, many formulations of polyimide are biocompatible, meaning that polyimide is safe for use within the human body, such as within the ear of patient 10. This property makes polyimide suitable to use as part of first shaft 114 and second shaft 116, since first shaft 114 and second shaft 116 are inserted into the ear of patient 10.

In some embodiments, one or both of first shaft 114 and second shaft 116 include a stainless steel material such as stainless steel hypodermic tubing. Stainless steel hypodermic tubing is a kind of hollow tube made from stainless steel. In some cases, hypodermic tubing can be manufactured to precise dimensions (e.g., inner diameter, outer diameter, length) to ensure consistency in diameter, wall thickness, and surface finish. This precision is crucial for applications such as medical devices and instruments. Stainless steel is resists corrosion, making this material useful in environments such as the human ear where moisture, chemicals, and bodily fluids are located. Stainless steel can be strong and durable, which allows stainless steel hypodermic tubing to withstand high pressures and mechanical stresses. Stainless steel can also be biocompatible, meaning that stainless steel is well-tolerated by the human body without causing adverse reactions.

First shaft 114 and second shaft 116 are not limited to including polyimide and/or stainless steel. In some embodiments, one or both of first shaft 114 and second shaft 116 include materials such as titanium, platinum, Nitinol, Cobalt-Chromium alloys, polyethylene, polyethylene terephthalate (PET), polyetheretherketone (PEEK), ceramics, fluoropolymers, silicone, or any combination thereof. In any case, first shaft 114 and second shaft 116 may comprise materials that are biocompatible with the human ear and possess mechanical and thermal properties suitable for delivering the formulation to the targeted site within the ear of patient 10.

In some embodiments, first shaft 114 has an outer diameter (refer to D1 in FIG. 10 below) within a range from 0.5 mm to 1.5 mm, and preferably from 1.0 mm to 1.4 mm. In one embodiment, first shaft 114 has an outer diameter of 1.3 mm. It may be beneficial for first shaft 114 to have a small outer diameter that accommodates tip-mounted camera 112 so that the profile of first shaft 114 through tympanic membrane 30 is limited. For example, when tip-mounted camera 112 includes a CMOS camera and an LED, this may allow first shaft 114 to have a small outer diameter within the range from 0.5 mm to 1.5 mm. When tip-mounted camera 112 includes a light source removed from the tip of first shaft 114 and an optical waveguide to bring light from the light source to the tip of first shaft 114, this may decrease a diameter of first shaft 114 as compared with embodiments where a light source (e.g., an LED) is located at the tip of first shaft 114. In any case, an outer diameter of first shaft 114 may allow first shaft 114 to traverse tympanic membrane 30 in a minimally invasive procedure to deliver a formulation to a targeted site in an ear of patient 10 and/or traverse a hole 62 in mastoid bone 60 to reach the middle ear 40.

Second shaft 116, in some embodiments, has an outer diameter (refer to D2 in FIG. 10 below) within a range from 0.20 mm to 0.50 mm. Preferably, the outer diameter of second shaft 116 is 0.41 mm. When the outer diameter of second shaft 116 is within a range from 0.20 mm to 0.50 mm, this may limit a profile of second shaft 116 through tympanic membrane 30 so that delivering the formulation to the targeted site in the ear of patient 10 is minimally invasive. That is, when the outer diameter of second shaft 116 is within a range from 0.20 mm to 0.50 mm, the profile of second shaft 116 is more like a needle than a catheter, thus limiting traumatic impact to the tympanic membrane 30. In an embodiment where an outer diameter of first shaft 114 is 1.3 mm and an outer diameter of second shaft 116 is 0.41 mm, a total distance across first shaft 114 and second shaft 116 is 1.66 mm. This width allows first shaft 114 and second shaft 116 to simultaneously advance through a needle puncture in tympanic membrane 30 while minimizing trauma to the tympanic membrane 30. These dimensions also accommodate transmastoid access to the middle ear 40 via a hole 62 in the mastoid bone 60. This is because a total width of first shaft 114 and second shaft 116 is small enough to fit through the hole 62 and a passageway from the hole 62 to the cochlea 50.

In some embodiments, one or both of a tip region of first shaft 114 and a tip region of second shaft 116 comprises a silicone material. Silicone is generally less rigid than polyimide. Polyimide is a high-performance polymer known for its excellent mechanical strength, dimensional stability, and high temperature resistance and is often used in applications where rigidity and stability are critical. Silicone is a flexible and elastomeric material. While silicone can vary in hardness depending on formulation and processing, silicone is typically softer and more flexible compared to polyimide. This means that it may be beneficial to use silicone at one or both of a tip region of first shaft 114 and a tip region of second shaft 116, because the tip regions of first shaft 114 and second shaft 116 cross the tympanic membrane 30 of patient 10. In other words, first shaft 114 and second shaft 116 can be less traumatic to the ear of patient 10 when first shaft 114 and second shaft 116 comprise silicone tips as compared with examples where shafts do not include silicone tips.

Delivery tool 110 includes handle 118 configured to receive a proximal portion of first shaft 114 and a proximal portion of second shaft 116. In some examples, handle 118 receives the first shaft 114 and the second shaft 116 through distal opening 120 of handle 118. Handle 118 can be sized so that a clinician is able to firmly grasp handle 118 with one hand while simultaneously advancing first shaft 114 and second shaft 116 of delivery tool 110 toward a targeted site. First shaft 114 and second shaft 116 can be fixedly attached to handle 118 so that first shaft 114 does not move relative to handle 118 and second shaft 116 does not move relative to handle 118. First shaft 114 and second shaft 116 can extend distally from handle 118 via distal opening 120.

In some embodiments, a distal section 136 of delivery tool 110 can be inserted into the ear of patient 10 and a proximal section 138 of delivery tool 110 can remain outside of the ear of patient 10 during a procedure to deliver a formulation. In other words, the clinician can insert delivery tool 110 up to a point on handle 118 that is midway between distal opening 120 of handle 118 and grip edges 135 of handle 118. Distal section 136 of delivery tool 110 is generally narrower than proximal section 138 of delivery tool 110. Distal section 136 can be sized to fit within the ear of patient 10 so that delivery tool 110 can advance to the targeted site within the ear of patient 10. Proximal section 138 can be sized for gripping by a user such as clinician 1. This means that a width of proximal section 138 can be sized to rest firmly and comfortably within features and contours of the human hand.

As shown in FIG. 4-6, a surface of handle 118 is curvilinear in shape. For example, the surface of handle 118 is curved such that some portions of handle 118 have a diameter that is greater than other portions of handle 118. In some embodiments, these curves can improve an ability of a clinician to grip handle 118 as compared with tools that do not have curvilinear surfaces in a grip area. This is because peaks and valleys can be easier to hold than flat surfaces. The peaks and valleys of handle 118 can engage with features of the clinician's hand, thus preventing handle 118 from slipping.

In some embodiments, handle 118 includes grip edges 135 on a surface of handle 118. Grip edges 135 can improve an ability of clinician 1 to grip handle 118 as compared with an ability of clinician 1 to grip a handle that does not include grip edges. This is because grip edges 135 can increase a coefficient of friction between fingers of clinician 1 and the surface of handle 118 as compared with a coefficient of friction between fingers and a smooth surface. The increased coefficient of friction leads to a decreased likelihood that handle 118 will slip from the grip of clinician 1. As shown in the illustrated embodiment, grip edges 135 are located on a part of handle 118 that is between a midpoint of handle 118 and a distal end of handle 118.

As shown in FIG. 4-6, the surface of handle 118 forms an undulating pattern. This undulating pattern gradually increases from a proximal end 144 of handle 118 to a first peak 145 of the surface of handle 118. The undulating pattern gradually decreases from a first peak 145 to a valley 146. The undulating pattern gradually increases again from a valley 146 to a second peak 147. From the second peak 147 to the distal opening 120 of handle 118, the undulating pattern of the surface gradually decreases.

In some examples, a cross-section of handle 118 at each point along a length of handle 118 is round (e.g., a circle, an oval). This means that a diameter of a cross-section of handle 118 at first peak 145 can be greater than a diameter of the cross-section of handle 118 at valley 146 and a diameter of a cross-section of handle 118 at second peak 147 is greater than a diameter of the cross-section of handle 118 at valley 146. A clinician can grip delivery tool 110 using a pencil grip. When delivery tool 110 is gripped using a pencil grip, a portion of handle 118 at valley 146 can rest in a space between the thumb and the index finger while the thumb, the index finger, and the middle finger engage hold grip edges 135.

Delivery tool 110 includes a connector piece 151 attached to a proximal end 144 of handle 118. As described above, connector piece 151 may represent a Luer connector for mating with a Luer lock of flexible tube 134 of FIG. 1-2. This means that delivery tool 110 is configured to receive the formulation through connector piece 151 located at the proximal end 144 of handle 118.

FIG. 4 illustrates a first view of delivery tool 110 from a first perspective looking at a side of delivery tool 110, where first shaft 114 is arranged above second shaft 116 in the example of FIG. 5. FIG. 5 illustrates a second view of delivery tool 110 from a second perspective looking at a side of delivery tool 110, where first shaft 114 and second shaft 116 are aligned in the same plane extending into the page. This means that the delivery tool 110 in the second view of FIG. 5 is rotated 90 degrees relative to the delivery tool 110 in the first view of FIG. 4. FIG. 6 illustrates a cutaway view of delivery tool 110 from the first perspective looking at the side of delivery tool 110.

Referring now to FIG. 6, tip-mounted camera 112 can, in some embodiments, be connected to an electrical conductor 113. As shown in FIG. 6, electrical conductor 113 can extend through a lumen 148 formed by first shaft 114. In some embodiments, electrical conductor 113 may extend from tip-mounted camera 112 out of delivery tool 110 through a gap between a proximal end of handle 118 and connector piece 151. Electrical conductor 113 may, in some examples, connect to display controller 140 of FIG. 1. For example, electrical conductor 113 can be disposed within image data cable 142 in some embodiments. Delivery tool 110 is not limited to the embodiment illustrated in FIG. 6. In some examples, electrical conductor 113 may exit delivery tool 110 at another location such as the proximal end of connector piece 151, a location between a proximal end of handle 118 and a distal end of handle 118, or another location.

Electrical conductor 113 can provide power to one or more components of tip-mounted camera 112 and/or facilitate communication with one or more components of tip-mounted camera 112 and other devices. For example, electrical conductor 113 may provide power to a camera sensor and/or a light source of tip-mounted camera 112. Additionally, or alternatively, a camera source of tip-mounted camera 112 can transmit image data via electrical conductor 113. Electrical conductor 113 is not limited to including a single conductor. In some embodiments, electrical conductor 113 includes more than one conductor, such as one conductor connected to an LED and another conductor connected to a camera sensor.

Delivery tool 110 is configured to deliver the formulation via the lumen 149 formed by second shaft 116 so that the formulation exits the distal opening at distal end 124 of second shaft 116. As shown in FIG. 6, distal port 115 is located at a distal end of lumen 149 that is defined by second shaft 116. This means that delivery tool 110 is configured to deliver the formulation via distal port 115. In some embodiments, a flexible tube (e.g., flexible tube 134 of FIG. 1-2) is configured to connect to connector piece 151 so that there is a single fluid path between fluid reservoir 132 of treatment actuator device 130 and distal port 115. This fluid path can extend from fluid reservoir 132, through a lumen defined by flexible tube 134, and through lumen 149 to distal port 115.

Because delivery tool 110 is configured to deliver the formulation via the distal opening of the lumen 149 formed by second shaft 116 at distal end 124 and because tip-mounted camera 112 is located at distal end 122 of first shaft 114, both first shaft 114 and second shaft 116 can simultaneously cross tympanic membrane 30 during a trans-tympanic membrane delivery procedure. This is because when delivery tool 110 delivers a formulation to a targeted site beyond tympanic membrane 30, a distal portion of first shaft 114 including tip-mounted camera 112 is configured to cross tympanic membrane 30 to provide direct visualization of the targeted site and a distal portion of second shaft 116 is configured to cross tympanic membrane 30 to reach the targeted site. Furthermore, the distal portion of first shaft 114 including tip-mounted camera 112 is configured to pass through a hole 62 in the mastoid bone 60 to provide direct visualization of the targeted site and a distal portion of second shaft 116 is configured to reach the targeted site in examples where delivery tool 110 uses transmastoid access.

A total length of the delivery tool 110 from a proximal end of the delivery tool 110 to a distal end of delivery tool 110 is equal to length L4. In some embodiments, length L4 may be within a range from 120 mm to 200 mm. In Preferably, length L4 is equal to approximately 161 mm. When length L4 is equal to 161 mm or another similar length, this means that delivery tool 110 is sized for clinician to navigate delivery tool 110 to a targeted site within the ear of patient 10 while gripping delivery tool 110 outside of the ear of patient 10. Handle 118 can have length L5. In some embodiments, length L5 is within a range from 100 mm to 150 mm. Length L5 of handle 118 can be significantly longer than a length L1 of first shaft 114 extending distally from distal opening 120 and a length L2 of a second shaft 116 extending distally from distal opening 120. In some cases, handle 118 is relatively longer than the exposed portions of first shaft 114 and second shaft 116 because the exposed portions of first shaft 114 and second shaft 116 are sized to fit within the ear of the patient a majority of handle 118 is sized to remain outside of the ear.

Figure 7:
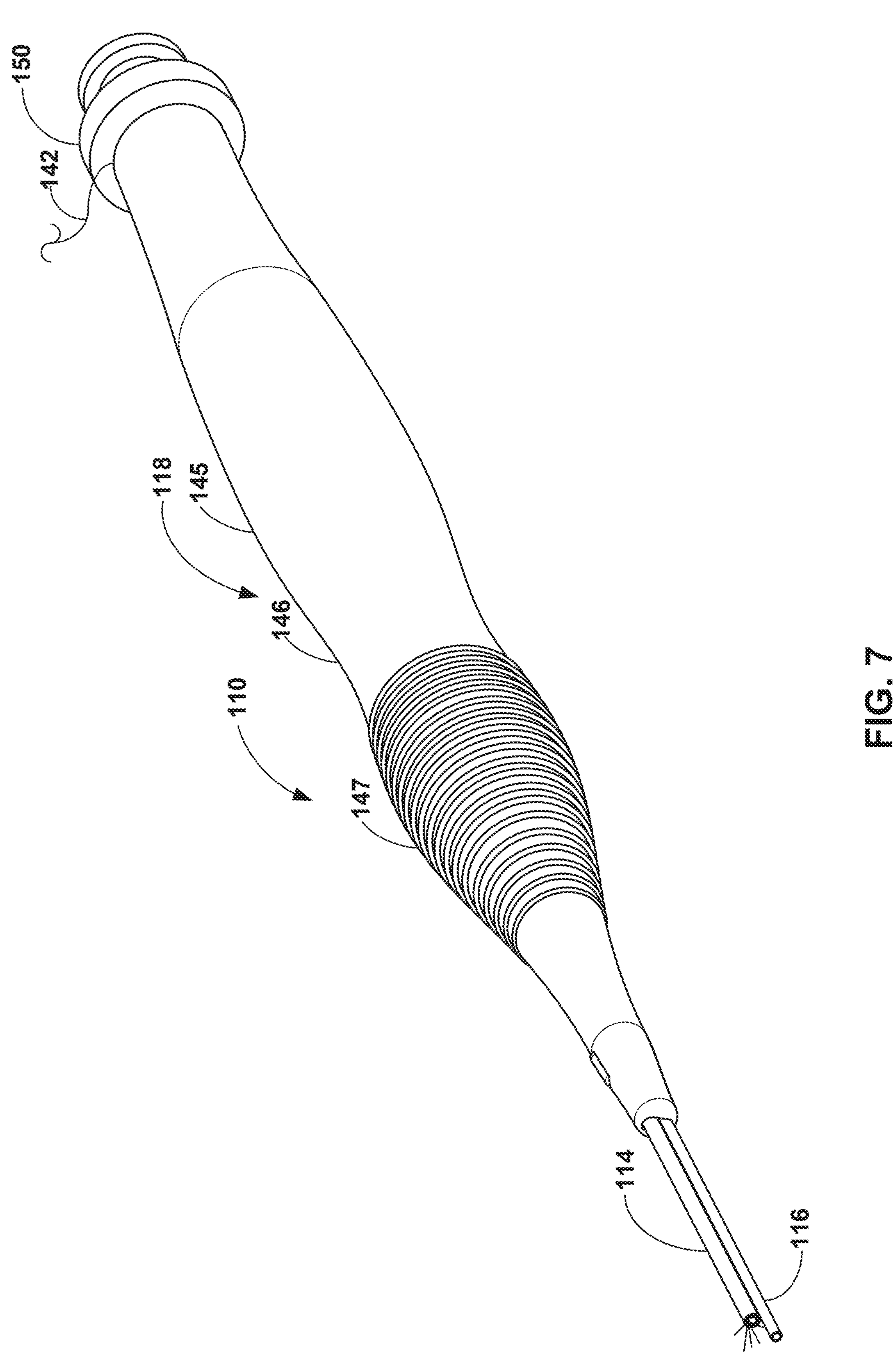
FIG. 7 shows a perspective view of the delivery tool of FIG. 4.
Figure 8:
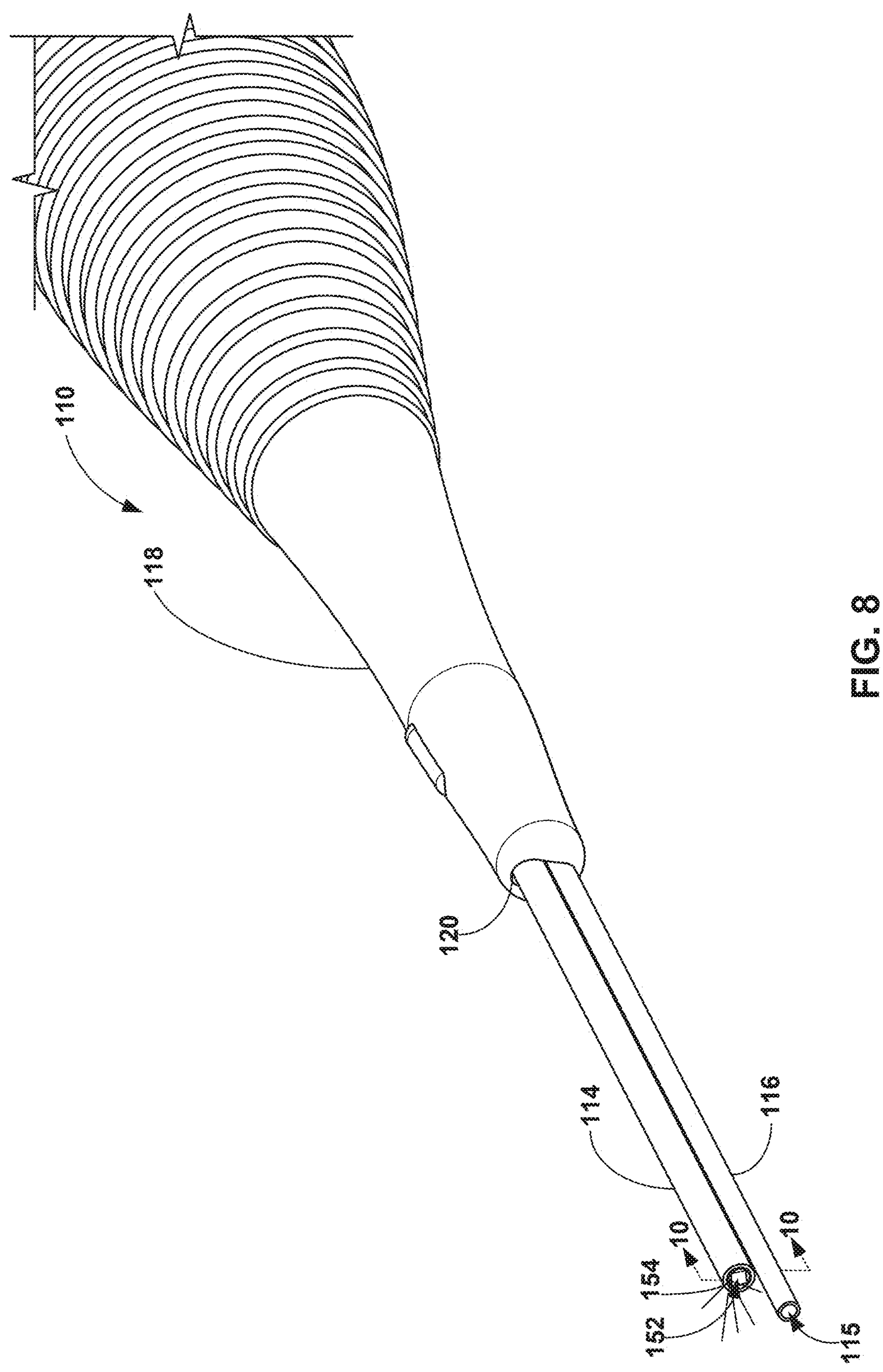
FIG. 8 shows a perspective view of a portion of the delivery tool of FIG. 7.
Figure 9:
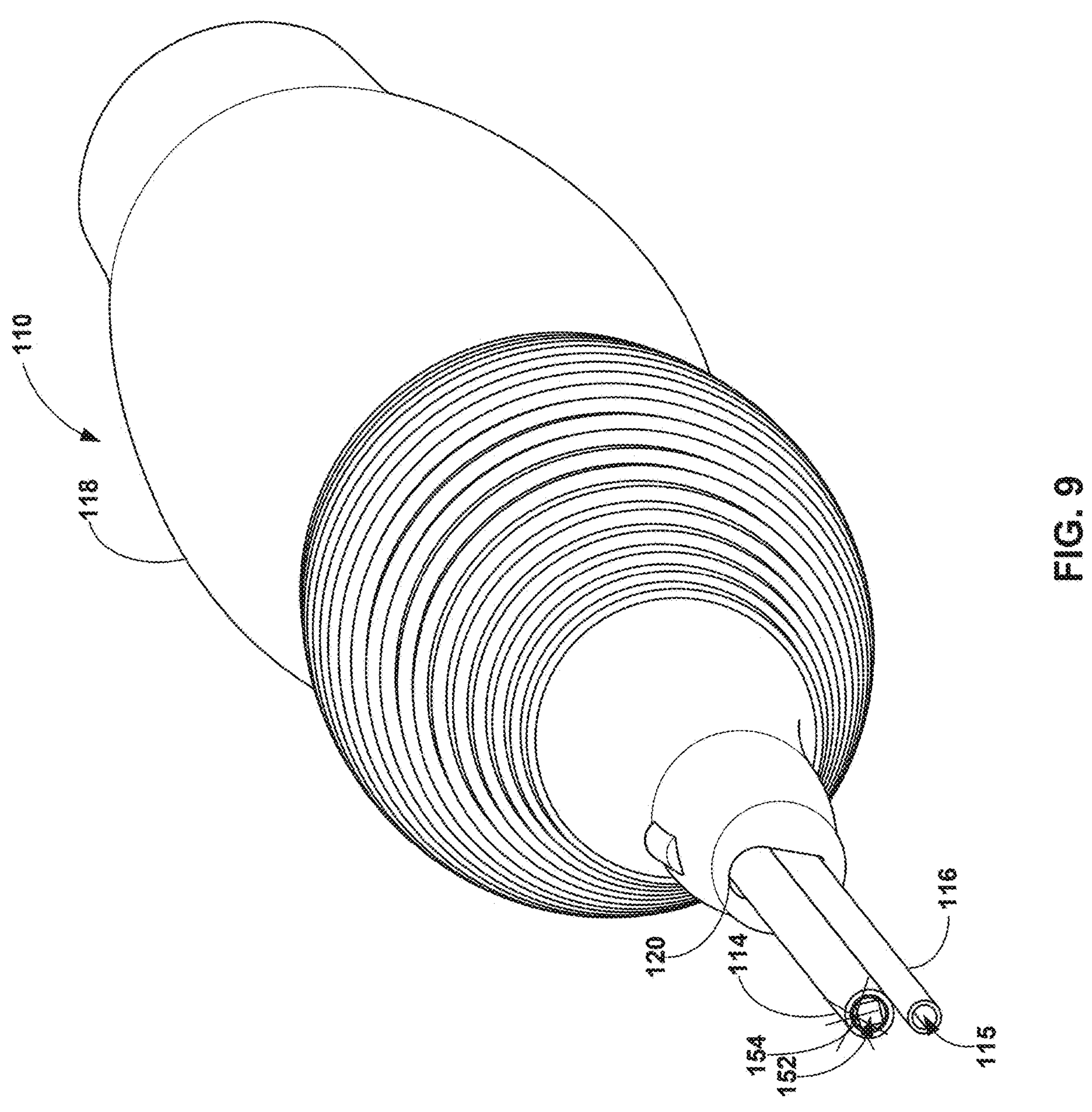
FIG. 9 shows another perspective view of the delivery tool of FIG. 7.

Referring now to FIG. 7-9, first shaft 114 and second shaft 116 extend distally from distal opening 120 of delivery tool 110. Delivery tool 110 generally forms a round shape, where a diameter of delivery tool 110 varies along a length of delivery tool 110. As shown in FIG. 7, for example, a diameter of handle 118 increases from a proximal end of delivery tool 110 to a first peak 145, decreases to a valley 146 of delivery tool 110, increases to a second peak 147, and decreases to a distal end of handle 118.

The shape of handle 118 is generally round and extends along a longitudinal axis. In some embodiments, the generally round shape of handle 118 assists clinician 1 in gripping handle 118. For example, round handles do not include sharp edges that are uncomfortable to grip tightly. Since handle 118 is round, clinician 1 is able to easily rotate a grip so that the distal end of first shaft 114 and the distal end of second shaft 116 are oriented properly within the ear to reach the targeted site.

In the example of FIG. 7-9, the shape of handle 118 is generally symmetric about a longitudinal axis of delivery tool 110. This means that handle 118 does not favor being gripped by a left hand or a right hand. Handle 118 can be gripped equally effectively by a right hand or a left hand. Handle 118 is shaped for a comfortable grip.

For example, the smooth and shallow region proximate to valley 146 can rest comfortably between the thumb and the index finger of clinician 1.

As shown in FIG. 7-9, first shaft 114 and second shaft 116 are both cylindrical. In some embodiments, a diameter of first shaft 114 is greater than a diameter of second shaft 116. This is because a distal tip of first shaft 114 can accommodate an image sensor 152 and a light source 154, the image sensor 152 being wider than the distal port 115 at the distal tip of second shaft 116. Since the image sensor 152 is placed on a distal end of first shaft 114, the diameter of first shaft 114 is great enough so that the entire surface area of image sensor 152 fits on the distal end of first shaft 114. Light source 154 is also located on the distal end of first shaft 114 in the example of FIG. 7-9.

In some embodiments, image sensor 152 comprises a camera sensor. Preferably, image sensor 152 comprises a CMOS camera sensor. Image sensor 152 can, in some cases, be rectangular in shape. An array of light-sensitive pixels can be located on a surface of the image sensor 152. Each of these light-sensitive pixels can record an intensity of light arriving at the pixel. Image data generated by circuitry of the image sensor 152 can include a sequence of image frames, each image frame indicating an intensity value corresponding to each of the pixels. This image data can be displayed on the screen of display device 150 in real time.

Light source 154 preferably comprises an LED. Optionally, light source 154 includes a waveguide configured to emit light or another kind of light source. The targeted site in the ear of patient 10 for delivering the formulation using delivery tool 110 can be in a dark location that receives little or no natural light and is not visible to the naked eye of an observer. In some embodiments, light source 154 is configured to emit light into the area where the targeted site is located so that image sensor 152 can capture anatomical features within the area. Image sensor 152 and light source 154 may be part of tip-mounted camera 112. As shown in FIG. 7-9, light source 154 is configured to emit light rays from the distal end of first shaft 114 extending distally beyond the distal end of second shaft 116. Some of these light rays reflect off objects in and image sensor 152 senses the reflected rays.

At least part of a portion of second shaft 116 that extends distally beyond a distal end of first shaft 114 is within a field of view of image sensor 152. This means that image sensor 152 is configured to capture a distal portion of second shaft 116. When the distal end of first shaft 114 and the distal end of second shaft 116 are both located beyond tympanic membrane 30 (or within middle ear 40 when delivery tool 110 uses transmastoid access), image sensor 152 is therefore configured to capture the location of the distal portion of second shaft 116 relative to a location of one or more anatomical features of the middle ear 40 of patient 10. This means that the image data captured by image sensor 152 can indicate whether the distal portion of second shaft 116 is positioned to deliver a formulation to a targeted site in the ear of patient 10.

Second shaft 116 defines a distal port 115 at a distal end of second shaft 116. Delivery tool 110 is configured to deliver a formulation to the targeted site through distal port 115 at the distal end of second shaft 116. The lumen defined by second shaft 116 may extend through an entire length of second shaft 116. Connector piece 151 may connect a flexible tube to the lumen defined by the second shaft 116. An insertion device may connect to the flexible tube.

Figure 10:
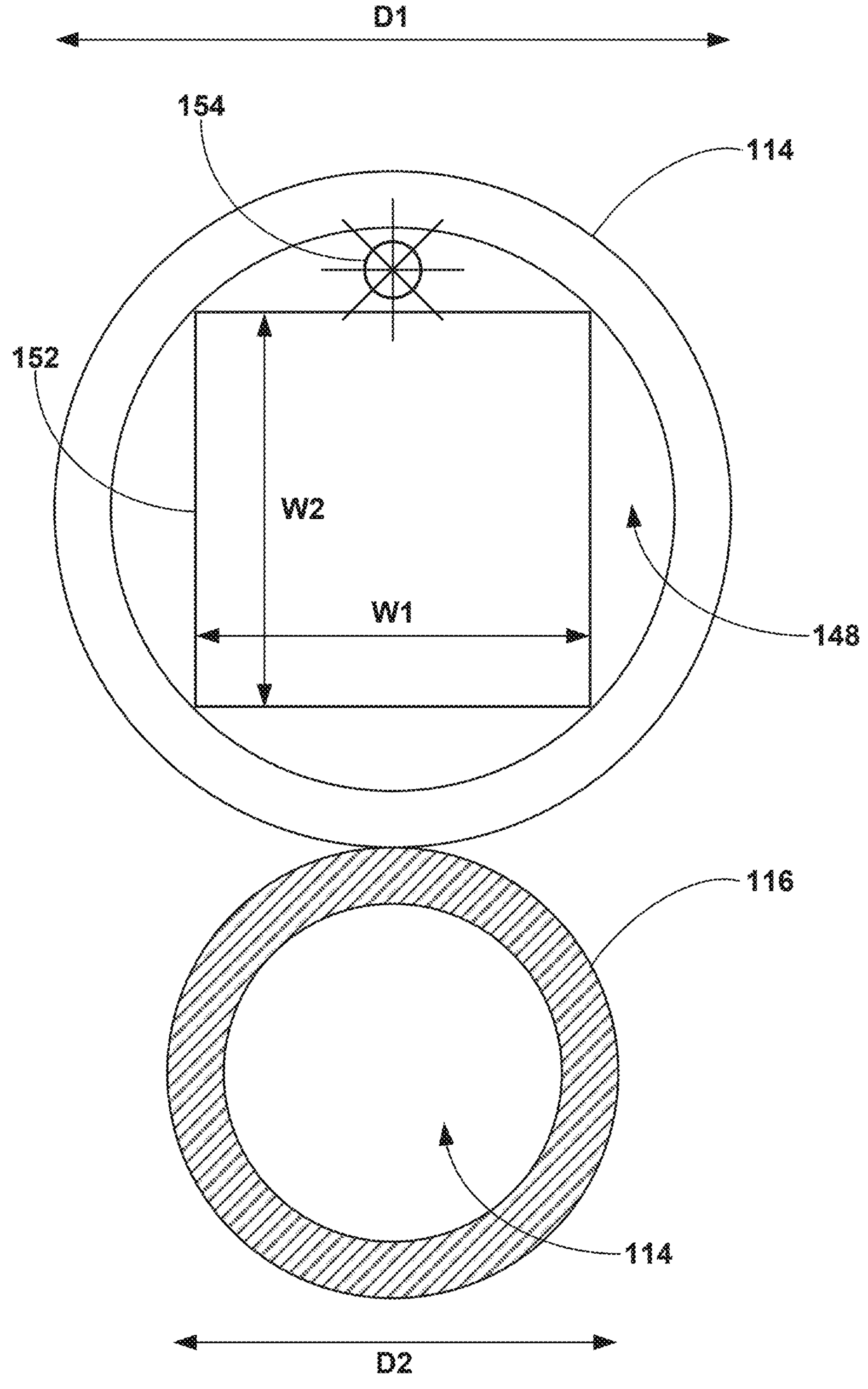
FIG. 10 shows an example cross-section of the delivery tool of FIG. 7 including the first shaft and the second shaft.

Referring now to FIG. 10, an example cross-sectional view of first shaft 114 and second shaft 116 shows image sensor 152 and light source 154 located on a tip of first shaft 114 and a cutaway view of second shaft 116. The view of FIG. 10 is a cutaway view of delivery tool 110 at the distal end of first shaft 114. This means that the distal end of second shaft 116 including distal port 115 is out of the page relative to the view of FIG. 10. Image sensor 152 and light source 154 are in the plane of the view of FIG. 10.

As shown in FIG. 10, a surface of first shaft 114 is in contact with a surface of second shaft 116. A diameter D1 of first shaft 114 is greater than a diameter D2 of second shaft 116 in some embodiments. For example, the diameter D1 of first shaft 114 is 0.5 mm to 1.5 mm, preferably 1.0 mm to 1.4 mm, and 1.3 mm in the depicted embodiment. And in such examples, the diameter D2 of second shaft 116 is about 0.20 mm to about 0.50 mm, and preferably about 0.41 mm in the depicted embodiment. Also, the diameter D1 of the first shaft 114 is greater than a maximum lateral width of the image sensor 152 so that the distal-facing end of the first shaft 114 can accommodate the entire surface of image sensor 152. Image sensor has a first width W1 and a second width W2. In some examples, both of W1 and W2 are less than 1.5 mm, and preferably 1 mm or less. In one embodiment, W1 is equal to 0.575 mm and W2 is equal to 0.575 mm. Further still, the diameter D1 of the first shaft 114 is greater than the widths W1 and W2 of the image sensor 152 by an amount sufficient to accommodates light source 154, which is configured to emit light extending distally from a distal end of first shaft 114. In some examples, first shaft 114 defines a lumen 148 that is sealed at the distal end by a fixed wall (which may comprise an electronics circuit) within the shaft 114 to which image sensor 152 and light source 154 are mounted in an outwardly distal-facing orientation. One or more conductive cables connected to image sensor 152 and light source 154 may extend through lumen 148.

Image sensor 152 may be located in a center region of a distal end of first shaft 114 in some embodiments. As shown in FIG. 10, image sensor 152 is disposed in a center region of the cross-section of first shaft 114. In some examples, a center point of image sensor 152 is located on a center axis of first shaft 114. Light source 154, in some examples, is located in an edge region of a distal end of first shaft 114. As shown in FIG. 10, light source 154 is located in an edge region of first shaft 114 above image sensor 152 which is located in a center region of first shaft 114. An "edge region" of a surface may refer to a region that is displaced from a center of the surface. A "center region" of a surface may refer to a region that includes the center of the surface.

Figure 11A:
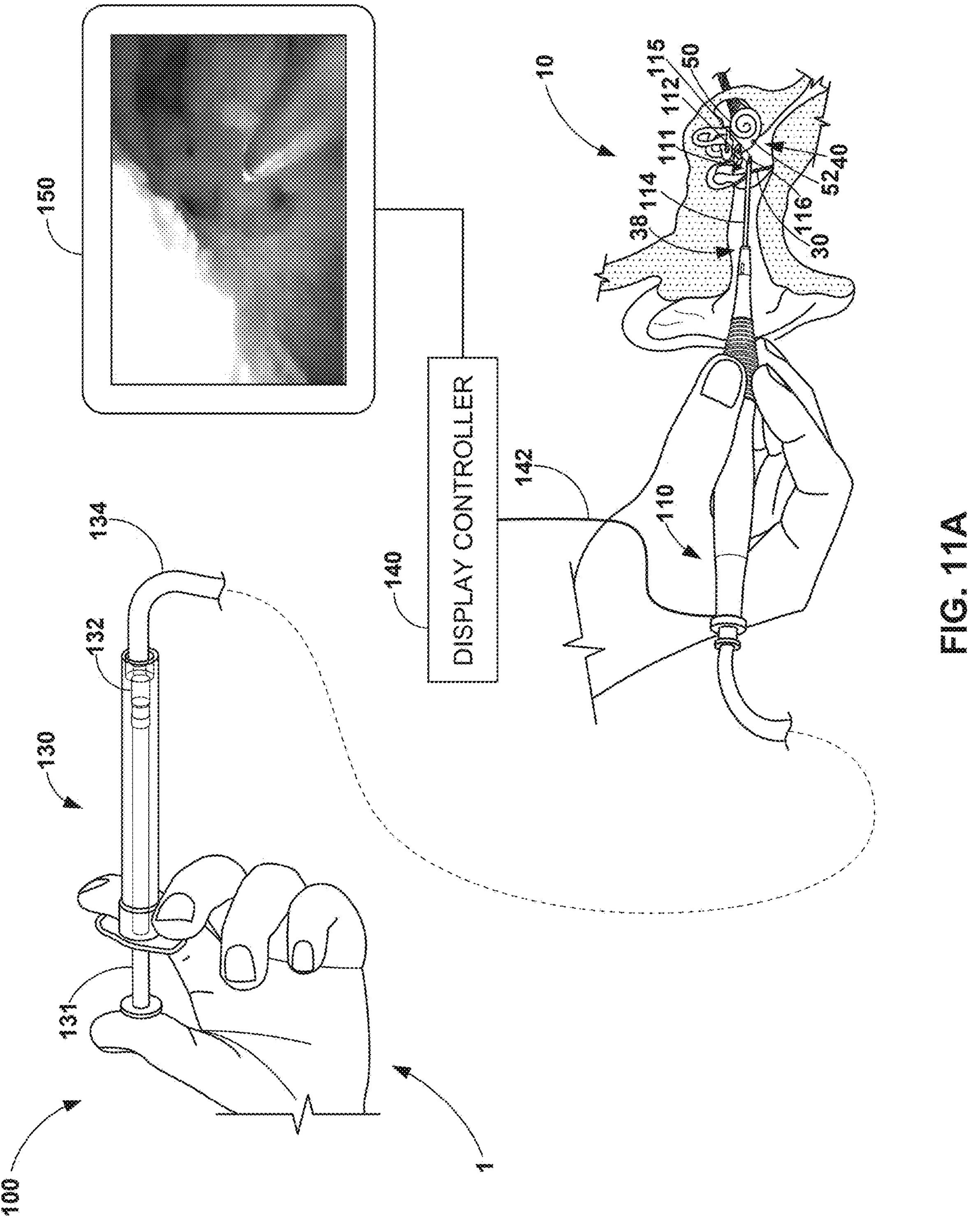
FIG. 11A is a perspective view of an ear treatment system configured to use transcanal access to deliver a formulation to a targeted site within an ear, in accordance with some embodiments.

Referring now to FIG. 11A, some embodiments of an ear treatment system 100 can be used to access an ear of a patient 10 through a small opening in the tympanic membrane. Ear treatment system 100 can include a delivery tool 110, a treatment actuator device 130 (e.g., a fluid delivery syringe in the depicted embodiment), and a display device 150 for providing onscreen visualization of the delivery tool 110. A distal portion 111 of the delivery tool 110 can extend through the small opening in the tympanic membrane. As described in detail below, the delivery tool 110 can be implemented as a handheld otologic instrument having a handle configured to be retained by a user 1 (external to the ear) and one or more shafts that extend distally from the handle for insertion in a trans-tympanic path (e.g., through an opening formed in the tympanic membrane) to deliver a therapeutic formulation to a targeted site of the patient 10.

As described herein, in some cases the therapeutic formulation is a liquid or gel, and the targeted site is a round window membrane 52 of a cochlea 50. For example, a procedure to implement an auditory medical device (e.g., cochlear implant device 102) can involve delivering the therapeutic formulation to the round window membrane 52 prior to inserting a cochlear implant lead 104 of the device 102 into the patient's cochlea 50. This is because the cochlear implant lead 104 can be inserted into the cochlea 50 through the round window membrane 52 and it is beneficial to prepare the round window membrane 52 for the insertion of the cochlear implant lead 104 by delivering the therapeutic formulation to the round window membrane 52. In some cases, delivery tool 110 can deliver the therapeutic formulation to the round window membrane 52 days, weeks, or months (e.g., up to two months) before the procedure to deliver the cochlear implant lead 104 to the cochlea.

The targeted site is not limited to being the round window membrane 52. It should be understood from the description here that, in some embodiments, the targeted site can be another location in the middle ear or within the inner ear. For example, cochlear implant lead 104 is not limited to entering the cochlea 50 through the round window membrane 52. Cochlear implant lead 104 can enter the cochlea 50 through a cochleostomy that is separate from the round window membrane 52. In these examples, the delivery tool 110 can deliver the therapeutic formulation to an approximate location where clinician 1 will eventually make the cochleostomy for inserting the cochlear implant lead 104 into the cochlea 50. This can prepare the location for a subsequent procedure during which clinician 1 performs one or more cuts to make the cochleostomy and inserts the cochlear implant lead 104 into the cochlea 50 during the cochleostomy.

In some examples, delivery tool 110 can include a fluid delivery shaft that is sized to penetrate the round window membrane and deliver a therapeutic formulation directly into the cochlea, such as into the perilymph of the inner ear. Also as described in more detail below, the delivery tool 110 can be equipped with tip-mounted camera 112 fixed to a distal end of a first shaft 114, which can advantageously provide direct visualization of the delivery of the therapeutic formulation to the targeted site via a distal port 115 located at a distal end of a second shaft 116. This tip-mounted camera 112 can provide direct visualization of the anatomy of the patient's ear relative to a location of distal port 115.

For example, in use during some implementations, the clinician can readily grasp a handle of the delivery tool 110 (e.g., using a pencil grip or other grip that enhances control and accuracy) to simultaneously insert side-by-side shafts of the delivery tool 110 through a small opening formed in the tympanic membrane 30, such a surgical opening that is no greater than 2 millimeters (mm) and preferably about 1 mm to about 2 mm. Under direct visualization provided by the tip-mounted camera 112 of the delivery tool that is in communication with the display device 150 (via image data cable 142 and display controller 140 in the depicted embodiment), the clinician 1 can grasp the handle of the delivery tool 110 to accurately advance a distal port of the second (longer) shaft 116 toward the round window membrane of the cochlea while the tip-mounted camera 112 at a distal end of first (shorter) shaft 114 provides direct visualization of the second shaft 116. From there, while the clinician 1 uses a first hand to retain the delivery tool 110 in its operative position (with the distal port 115 of the second shaft 116 proximate to the round window membrane and under direct visualization), the clinician 1 can engage the treatment actuator device 130 using a second hand to achieve controlled delivery of the therapeutic formulation from the distal port.

In cases where delivery tool 110 is delivering therapeutic formulation to a targeted site (e.g., round window membrane 52 or a cochleostomy) where cochlear implant lead 104 will eventually be implanted within cochlea 50, delivery tool 110 can use transcanal access to reach the targeted site within the middle ear 40. For example, as depicted in FIG. 11A, the clinician 1 can simultaneously advance the shafts 114, 116 of the delivery tool 110 through ear canal 38 of patient 10 across the tympanic membrane 30 so that a distal portion of first shaft 114 and a distal portion of second shaft 116 are both within the middle ear 40. Clinician 1 can advance the delivery tool 110 so that the distal port 115 at the distal end of the second shaft 116 is adjacent the targeted site (e.g., round window membrane 52 or a cochleostomy).

Because tip-mounted camera 112 provides direct visualization of the distal portion of second shaft 116 relative to anatomy of the middle ear 40, the clinician 1 can determine whether the distal port 115 is sufficiently placed near the targeted site by looking at display device 150. When the distal port 115 is at the targeted site, the clinician 1 can control the treatment actuator device 130 to deliver the therapeutic formulation to the targeted site. For example, the clinician 1 can push the plunger actuator 131 inwards relative to a body of treatment actuator device 130, which causes the therapeutic formulation to move through a fluid passageway. This fluid passageway extends from fluid reservoir 132, through flexible tube 134, and into the lumen of second shaft 116. The therapeutic formulation exits the distal port 115 at the targeted site.

In some cases, it is beneficial for delivery tool 110 to access the middle ear 40 using transcanal access (as opposed to transmastoid access) to deliver the therapeutic formulation in advance of the procedure for delivering the cochlear implant lead 104 to cochlea 50. The procedure to deliver cochlear implant lead 104 is an invasive procedure during which patient 10 is under general anesthesia. Before such a procedure commences, there is not a surgical pathway to the middle ear 40 through the mastoid bone 60. That is, before clinician 1 opens a pathway to deliver cochlear implant lead 104 through the mastoid bone 60, transmastoid access is not available. Delivery tool 110 is advantageously sized to access the middle ear 40 through the ear canal 38 and across the tympanic membrane 30 in a minimally invasive procedure that does not involve patient 10 being placed under general anesthesia. This provides the clinician 1 with a minimally invasive way to access the targeted site in the middle ear 40 prior to the procedure to deliver cochlear implant lead 104.

Still referring to FIG. 11A, the ear treatment system 100 described herein can be in particular methods to treat and/or prevent a variety of ear conditions, including but not limited to hearing loss (such as hidden hearing loss, noise-induced hearing loss, age-related hearing loss, drug-induced hearing loss (e.g., chemotherapy-induced hearing loss or aminoglycoside-induced hearing loss), sudden sensorineural hearing loss (SNHL), autoimmune inner ear disease, and the like) or particular disorders of the middle ear and/or inner ear (such as tinnitus, balance disorders including vertigo and Meniere's Disease, vestibular neuronitis, vestibular schwannoma, labyrinthitis, otosclerosis, ossicular chain dislocation, cholesteatoma, and middle ear infections). Additionally, as described below, the ear treatment system 100 can be used in such a manner to treat a variety of ear conditions while also providing enhanced comfort to the clinician 1 and real-time direct visualization during delivery of the treatment in the middle or inner ear.

Figure 11B:
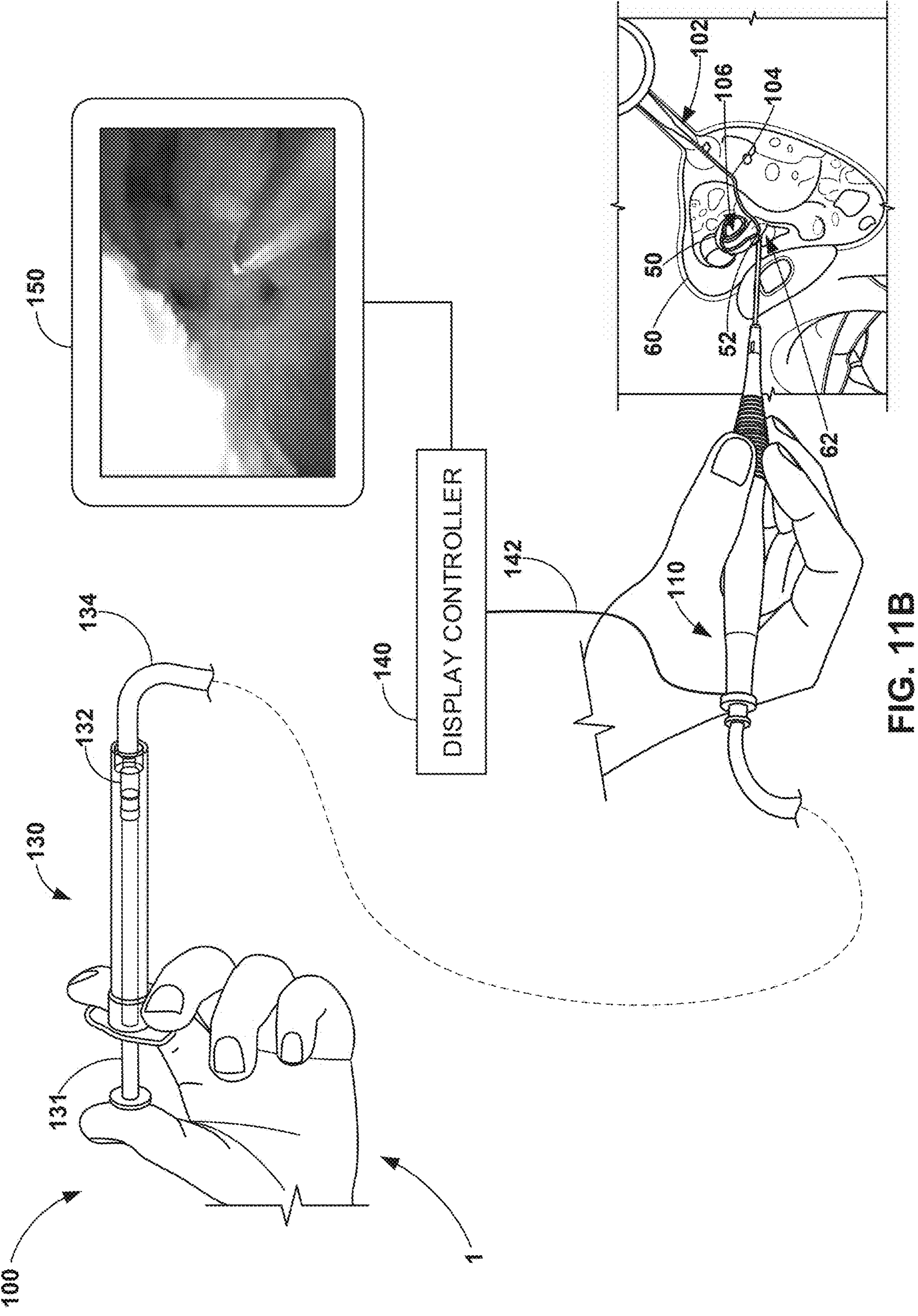
FIG. 11B is a perspective view of an ear treatment system configured to use transmastoid access to deliver a formulation to a cochlear implant lead insertion site within an ear, in accordance with some embodiments.

Referring now to FIG. 11B, some embodiments of an ear treatment system 100 can be used to access an ear of a patient 10 through a hole 62 in the mastoid bone 60. As described above, ear treatment system 100 can include a delivery tool 110, a treatment actuator device 130 (e.g., a fluid delivery syringe in the depicted embodiment), and a display device 150 for providing onscreen visualization of the delivery tool 110. A distal portion 111 of the delivery tool 110 can extend through the hole 62 in the mastoid bone 60. As described in detail below, the delivery tool 110 can be implemented as a handheld otologic instrument having a handle configured to be retained by a user 1 (external to the ear) and one or more shafts that extend distally from the handle for insertion in a transmastoid path (e.g., through the hole 62 in the mastoid bone 60) to deliver a therapeutic formulation to a targeted site of the patient 10.

In some examples, a transmastoid path to the patient's middle ear 40 can be created as part of an invasive surgical procedure such as a procedure to deliver a cochlear implant lead 104 of a cochlear implant device 102. Cochlear implant devices are medical devices that treat severe hearing loss disorders such as SNHL. For example, cochlear implant lead 104 can include one or more electrodes 106 that stimulate the cochlear nerve so that the patient 10 can regain some hearing that is lost as a result of severe hearing loss disorders. As depicted in FIG. 1B, cochlear implant lead 104 can extend into cochlea 50 through round window membrane 52 such that cochlear implant lead 104 follows the spiral interior pathway of cochlea 50. The electrodes 106 of cochlear implant lead 104 are spaced throughout this pathway on the inside of cochlea 50. Cochlear implant device 102 also includes one or more external components on the outside of the patient's skin that are connected to the cochlear implant lead 104, which extends into the cochlea of patient 10.

To deliver the cochlear implant lead 104, patient 10 can be placed under general anesthesia. Clinician 1 can make an incision in the patient's skin (e.g., a post-auricular incision behind the patient's ear). The clinician 1 can pull back the skin at the incision to expose the patient's mastoid bone 60. Subsequently, the clinician 1 can perform a mastoidectomy which involves drilling one or more holes (e.g., including hole 62) in the mastoid bone 60. These one or more holes can expose a pathway to the patient's middle ear 40 that exist behind the mastoid bone 60. In some examples, the cochlea 50 is visible through the holes in the mastoid bone 60, but this is not always the case. In some examples, clinician 1 creates the pathway to the middle ear 40 by performing one or more additional cuts.

Clinician 1 can, in some embodiments, insert the cochlear implant lead 104 into the cochlea 50 through the round window membrane 52. For example, the cochlear implant lead 104 can extend through one or more holes in the mastoid bone 60 so that the distal end of the cochlear implant lead 104 is within the cochlea 50. When the transmastoid pathway is closed following the procedure to deliver the cochlear implant lead 104, a proximal end of the cochlear implant lead 104 can be connected to external components of the cochlear implant device 102. This means that the electrodes 106 within the cochlea 50 can be electrically connected to the external components of the cochlear implant device 102 so that the external components can deliver electrical signals via the electrodes 106.

When a transmastoid pathway is already open as part of a procedure to deliver cochlear implant lead 104, delivery tool 110 can advantageously use this existing pathway to deliver a therapeutic formulation to a targeted site. In some examples, the targeted site is a cochlear implant lead insertion site where the cochlear implant lead 104 enters the cochlea 50. This cochlear implant lead insertion site can be the round window membrane 52 or another opening (e.g., a cochleostomy) into the cochlea 50 separate from the round window membrane 52. It can be beneficial to deliver the therapeutic formulation to the cochlear implant lead insertion site to seal the cochlear implant lead insertion site. Sealing the cochlear implant lead insertion site with the therapeutic formulation can be advantageous so that unwanted substances do not enter the cochlea 50 in a way that interferes with an operation of cochlear implant lead 104. Additionally, or alternatively, sealing the cochlear implant lead insertion site with the therapeutic formulation can prevent infection. Sealing the cochlear implant lead insertion site can also secure the cochlear implant lead 104 in place to prevent a migration of the lead after implant. Sealing the cochlear implant lead insertion site can also prevent fluid from leaking out of the cochlea 50 through the cochlear implant lead insertion site.

Clinician 1 can simultaneously advance the shafts 114, 116 into a hole 62 in the mastoid bone 60 so that a distal port 115 on the second shaft 116 reaches the cochlear implant lead insertion site (e.g., round window membrane 52). Since a transmastoid pathway through the hole 62 to the cochlear implant lead insertion site already exists for delivering the cochlear implant lead 104, delivery tool 110 can use this existing pathway to reach the cochlear implant lead insertion site. As described above, delivery tool 110 (including shafts 114, 116) can be sized so that the distal port 115 can reach the cochlear implant lead insertion site without clinician 1 performing any additional surgical cuts. This means that the surgical pathway that already exists for implanting the cochlear implant lead 104 is also suitable for delivery tool 110 to deliver the therapeutic formulation for sealing the cochlear implant lead insertion site.

In use during some implementations, the clinician 1 can readily grasp a handle of the delivery tool 110 (e.g., using a pencil grip or other grip that enhances control and accuracy) to simultaneously insert side-by-side shafts 114, 116 of the delivery tool 110 through the hole 62 in the mastoid bone 60. Under direct visualization provided by the tip-mounted camera 112 of the delivery tool that is in communication with the display device 150 (via image data cable 142 and display controller 140 in the depicted embodiment), the clinician 1 can grasp the handle of the delivery tool 110 to accurately advance a distal port of the second (longer) shaft 116 toward the round window membrane 52 of the cochlea 50 while the tip-mounted camera 112 at a distal end of first (shorter) shaft 114 provides direct visualization of the second shaft 116. From there, while the clinician 1 uses a first hand to retain the delivery tool 110 in its operative position (with the distal port 115 of the second shaft 116 proximate to the round window membrane 52 and under direct visualization), the clinician 1 can engage the treatment actuator device 130 using a second hand to achieve controlled delivery of the therapeutic formulation from the distal port 115.

In cases where delivery tool 110 is delivering therapeutic formulation to a targeted site (e.g., round window membrane 52 or a cochleostomy) where clinician 1 has just inserted cochlear implant lead 104 within cochlea 50, delivery tool 110 can use transmastoid access to reach the targeted site within the middle ear 40. For example, as depicted in FIG. 11B, the clinician 1 can simultaneously advance the shafts 114, 116 of the delivery tool 110 through ear the hole 62 in the mastoid bone 60 so that a distal portion of first shaft 114 and a distal portion of second shaft 116 are both within the middle ear 40. Clinician 1 can advance the delivery tool 110 so that the distal port 115 at the distal end of the second shaft 116 is adjacent the targeted site (e.g., round window membrane 52 or a cochleostomy).

Because tip-mounted camera 112 provides direct visualization of the distal portion of second shaft 116 relative to anatomy of the middle ear 40, the clinician 1 can determine whether the distal port 115 is sufficiently placed near the targeted site by looking at display device 150. When the distal port 115 is at the targeted site, the clinician 1 can control the treatment actuator device 130 to deliver the therapeutic formulation to the targeted site. For example, the clinician 1 can push the plunger actuator 131 inwards relative to a body of treatment actuator device 130, which causes the therapeutic formulation to move through a fluid passageway. This fluid passageway extends from fluid reservoir 132, through flexible tube 134, and into the lumen of second shaft 116. The therapeutic formulation exits the distal port 115 at the targeted site. In this way, the tip-mounted camera 112 can provide benefits that are similar to the benefits tip-mounted camera 112 provides in the transcanal approach. For example, in both the transmastoid approach and the transcranial approach, the tip-mounted camera 112 provides the direct visualization that enables the clinician 1 to determine whether the distal port 115 is positioned for delivering the therapeutic formulation.

In the example depicted in FIG. 11B, it can be advantageous for the delivery tool 110 to use a transmastoid pathway to reach the cochlear implant lead insertion site (as opposed to using the transcanal approach depicted in FIGS. 11A and 11C) because the transmastoid pathway already exists for another reason (e.g., to deliver cochlear implant lead 104) and using this pathway does not require the delivery tool 110 to cross the tympanic membrane 30. Although delivery tool 110 is sized to pass through a very small incision in the tympanic membrane 30, this small incision is not required for delivery tool 110 to reach the cochlea 50 using a transmastoid approach. Even though the transmastoid approach involves significant cuts to bone and tissue and involves patient 10 being under general anesthesia, the delivery tool 110 can use this approach when it is available in a way that avoids crossing the tympanic membrane 30.

The delivery tool 110 is not limited to using the transmastoid approach as a way to deliver the therapeutic formulation to seal the cochlear implant lead insertion site. In some examples, delivery tool 110 can use the transcanal approach depicted in FIGS. 11A and 11C to deliver the therapeutic formulation to seal the cochlear implant lead insertion site. For example, if a transmastoid pathway across the mastoid bone 60 and into the middle ear 40 is not sufficient for the delivery tool 110 to reach the cochlear implant lead insertion site, delivery tool 110 can access the cochlear implant lead through ear canal 38 and across tympanic membrane 30. This provides clinician 1 with the option to select the most appropriate way to reach the cochlear implant lead insertion site at the time of the procedure. The clinician 1 can select the access pathway that will present the fewest number of complications under the circumstances at that given time. For example, if transmastoid access would require the clinician 1 to make additional cuts or enlarge the opening in the mastoid bone 60, the clinician 1 might elect to use the transcanal approach. On the other hand, if transmastoid access would not require the clinician 1 to make additional cuts or enlarge the opening in the mastoid bone 60, the clinician 1 might elect to use transmastoid access. In any case, delivery tool 110 is advantageous in that the delivery tool 110 is sized to access the middle ear 40 using one or both of the transcanal approach and the transmastoid approach.

Figure 11C:
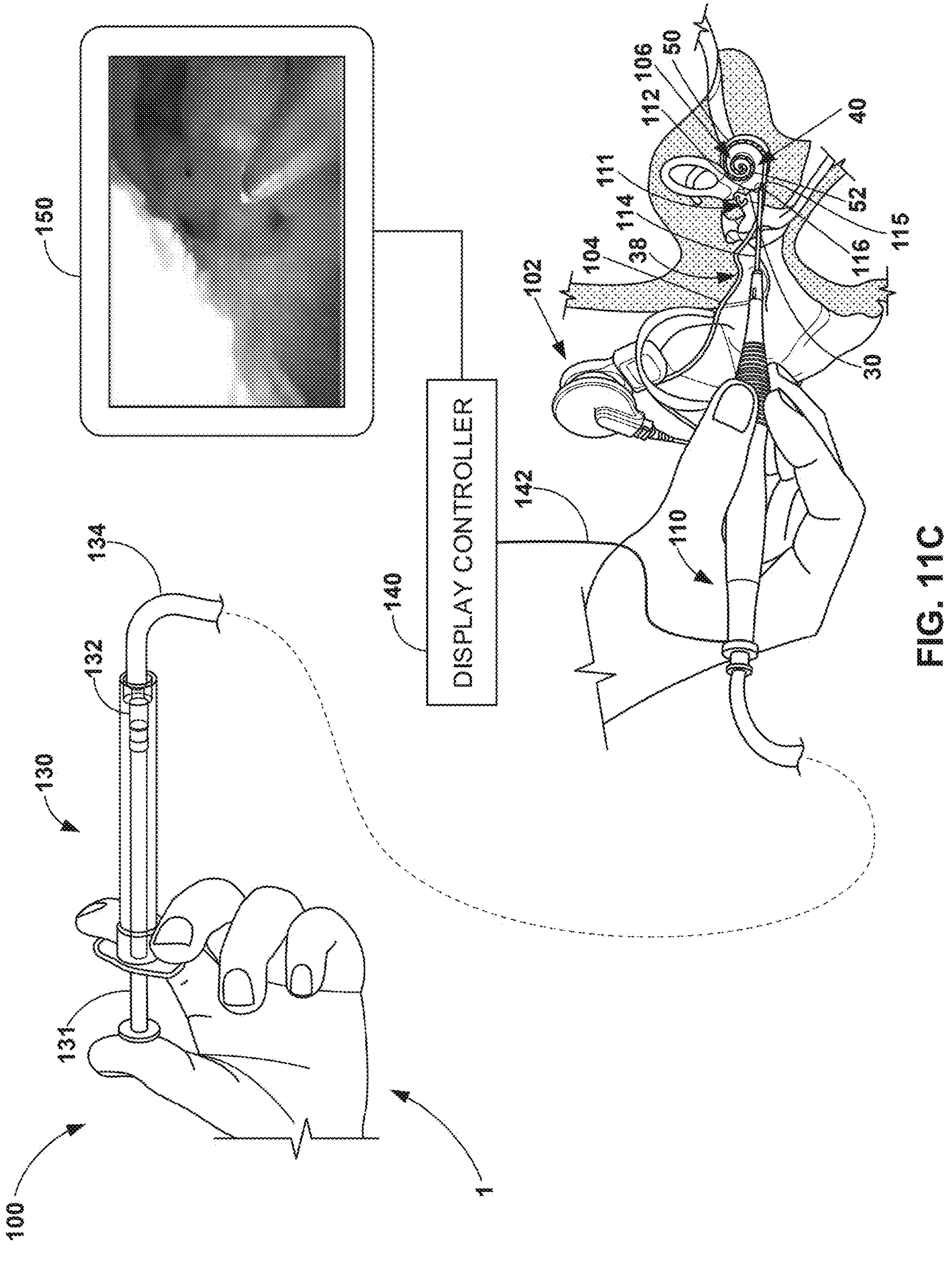
FIG. 11C is a perspective view of an ear treatment system configured to use transcanal access to deliver a formulation to a cochlear implant lead insertion site within an ear, in accordance with some embodiments.

Referring now to FIG. 11C, some embodiments of an ear treatment system 100 can be used to provide transcanal access an ear of a patient 10 through ear canal 38 and through a small opening in the tympanic membrane 30. The ear treatment system 100 depicted in FIG. 11C, in some examples, is the same as ear treatment system 100 depicted in FIGS. 11A and 11B. However, in FIG. 11C, cochlear implant device 102 is fully installed so that cochlear implant lead 104 is implanted within the patient's cochlea 50 and cochlear implant lead 104 is connected to one or more external components. For example, cochlear implant device 102 includes an external microphone transmitter that send electrical signals to cause the electrodes 106 to stimulate the patient's cochlear nerve.

In some examples, it can be advantageous for delivery tool 110 to deliver a therapeutic formulation to round window membrane 52 when cochlear implant device 102 has been fully implanted. For example, delivering the therapeutic formulation can provide one or more post-implant benefits including maintaining a seal of the cochlear implant lead insertion site, maintaining a position of the cochlear implant lead 104 within the cochlea 50, delivering therapy to the cochlea 50 via the round window membrane 52, or any combination thereof. When cochlear implant device 102 has been fully implanted so that cochlear implant lead 104 is within the cochlea 50 and transmastoid surgical openings used for implanting the cochlear implant lead 104 are closed, delivery tool 110 can deliver the therapeutic formulation to the cochlear implant lead insertion site using the transcanal approach as illustrated in FIG. 11C.

For example, as depicted in FIG. 11C, clinician 1 can use the same pathway to guide delivery tool 110 to the cochlear implant lead insertion site at round window membrane 52 that is depicted in FIG. 1A. For example, as depicted in FIG. 11C, the clinician 1 can simultaneously advance the shafts 114, 116 of the delivery tool 110 through ear canal 38 of patient 10 across the tympanic membrane 30 so that a distal portion of first shaft 114 and a distal portion of second shaft 116 are both within the middle ear 40. Clinician 1 can advance the delivery tool 110 so that the distal port 115 at the distal end of the second shaft 116 is adjacent the targeted site (e.g., round window membrane 52 or a cochleostomy) where the cochlear implant lead 104 enters the cochlea 50.

As described above, because tip-mounted camera 112 provides direct visualization of the distal portion of second shaft 116 relative to anatomy of the middle ear 40, the clinician 1 can determine whether the distal port 115 is sufficiently placed near the targeted site by looking at display device 150. When the distal port 115 is at the targeted site, the clinician 1 can control the treatment actuator device 130 to deliver the therapeutic formulation to the targeted site. For example, the clinician 1 can push the plunger actuator 131 inwards relative to a body of treatment actuator device 130, which causes the therapeutic formulation to move through a fluid passageway. This fluid passageway extends from fluid reservoir 132, through flexible tube 134, and into the lumen of second shaft 116. The therapeutic formulation exits the distal port 115 at the targeted site.

In some examples, it is advantageous for delivery tool 110 to use the transcanal approach to reach the round window membrane 52 for delivering a therapeutic formulation in embodiment where the cochlear implant lead 104 is fully implanted and there is not an open transmastoid passageway to the middle ear 40. As described above, a transmastoid passageway is opened through an invasive surgical procedure that involves significant bone and tissue cutting. It can be beneficial to avoid making these invasive cuts solely to provide access for delivery tool 110, because delivery tool 110 is sized for minimally invasive transcanal access as illustrated in FIG. 11C. Consequently, delivery tool 110 can use the transcanal approach to deliver a therapeutic formulation to round window membrane 52 in examples where cochlear implant lead 104 is fully implanted and no transmastoid pathway to the middle ear 40 is open.

Referring now to FIGS. 11A-11C, delivery tool 110 is sized to access the middle ear 40 to deliver a therapeutic formulation according to the transcanal approach, the transmastoid approach, or both. This means that delivery tool 110 can (1) use the transcanal approach to deliver the therapeutic formulation to the cochlear implant lead insertion site at round window membrane 52 before the cochlear implant lead 104 is inserted into the round window membrane 52, (2) use the transmastoid approach to deliver the therapeutic formulation to seal round window membrane 52 immediately after the cochlear implant lead 104 is implanted, and (3) use the transcanal approach to deliver the therapeutic formulation to the round window membrane 52 after the cochlear implant lead 104 is fully implanted. In some cases, delivery tool 110 is a single-use tool that is disposed after one use. In these examples, three different identically sized delivery tools can be used to deliver the therapeutic formulation before, during, and after cochlear implant lead 104 is implanted.

Figure 12:
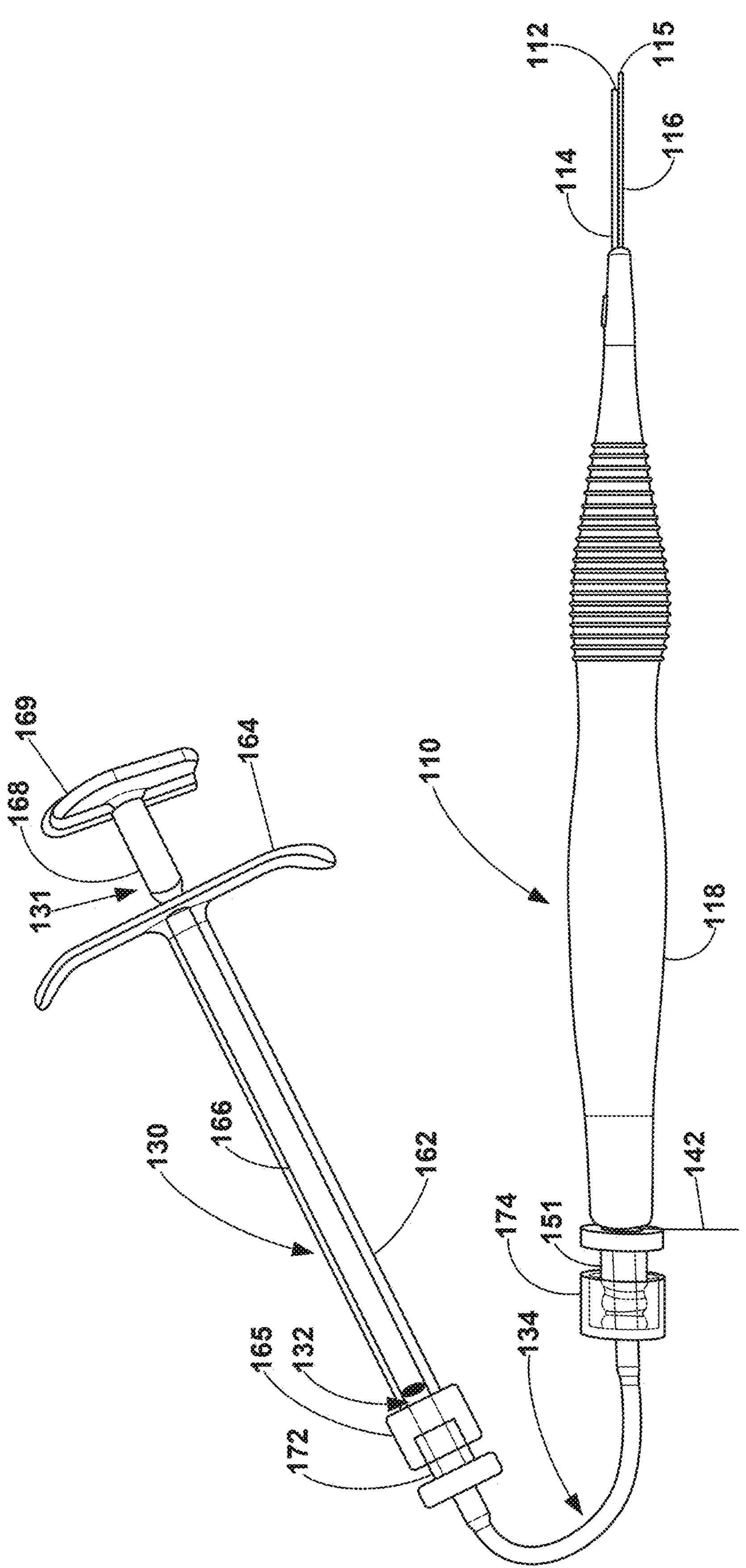
FIG. 12 shows the delivery tool, the treatment actuator device, and the flexible tube of the ear treatment system.

Referring now to FIG. 12, a delivery tool 110 can be connected to a treatment actuator device 130 using a flexible tube 134. As seen in FIG. 1, delivery tool 110 can include a first shaft 114, a second shaft 116, and a handle 118. The first shaft 114 and the second shaft 116 can extend from the handle 118. In some examples, first shaft 114 and second shaft 116 can be side-by-side and parallel, with second shaft 116 extending distally beyond a distal end of first shaft 114. In some examples, a tip-mounted camera 112 can be located at the distal end of first shaft 114 and a distal port 115 can be located at the distal end of second shaft 116. In some examples, the tip-mounted camera 112 can provide direct visualization of a distal portion of second shaft 116.

The treatment actuator device 130 includes a plunger actuator 131 and an actuator body 162. In some examples, the plunger actuator 131 includes an internal plunger portion 166, an external plunger portion 168, and a thumb portion 169. The actuator body 162 defines a fluid reservoir 132 and includes finger grips 164. In some examples, the internal plunger portion 166 can be slidably received within the fluid reservoir 132. As the internal plunger portion 166 advances distally to the end of the fluid reservoir 132, fluid is pushed out of the fluid reservoir 132, through the flexible tube 134, and into a fluid delivery lumen of the second shaft 116. In some examples, a user (e.g., a clinician) can place fingers on finger grips 164 and a thumb on thumb portion 169. By pressing the thumb, the user can depress the plunger actuator 131 into the fluid reservoir 132 to discharge fluid from the distal port 115 of second shaft 116. This is because fluid reservoir 132 is in fluid communication with the fluid delivery lumen of second shaft 116. In the example depicted in FIG. 12, plunger actuator 131 is fully extended into fluid reservoir 132 such that fluid reservoir 132 is almost completely occupied by the internal plunger portion 166. In this position, almost all of the liquid originally within fluid reservoir 132 is downstream of fluid reservoir 132, such as within the flexible tube 134, the fluid delivery lumen of second shaft 116, or discharged from the distal port 115 at a targeted site within the patient's ear.

The delivery tool 110 can be connected to the treatment actuator device 130 via a flexible tube 134. For example, treatment actuator device 130 can include a connector piece 165 on a distal end of treatment actuator device 130 and flexible tube 134 can include a connector piece 172 on a proximal end of flexible tube 134. The connector piece 165 and the connector piece 172 can connect to each other to secure treatment actuator device 130 to flexible tube 134. In some examples, connector piece 165 and connector piece 172 represent a Luer lock. Flexible tube 134 can include a connector piece 174 on a distal end of flexible tube 134 and delivery tool 110 can include a connector piece 151 on a proximal end of delivery tool 110. In some examples, connector piece 174 and connector piece 151 can connect to each other to secure flexible tube 134 to delivery tool 110. In some examples, connector piece 174 and connector piece 151 represent a Luer lock.

Figure 13:
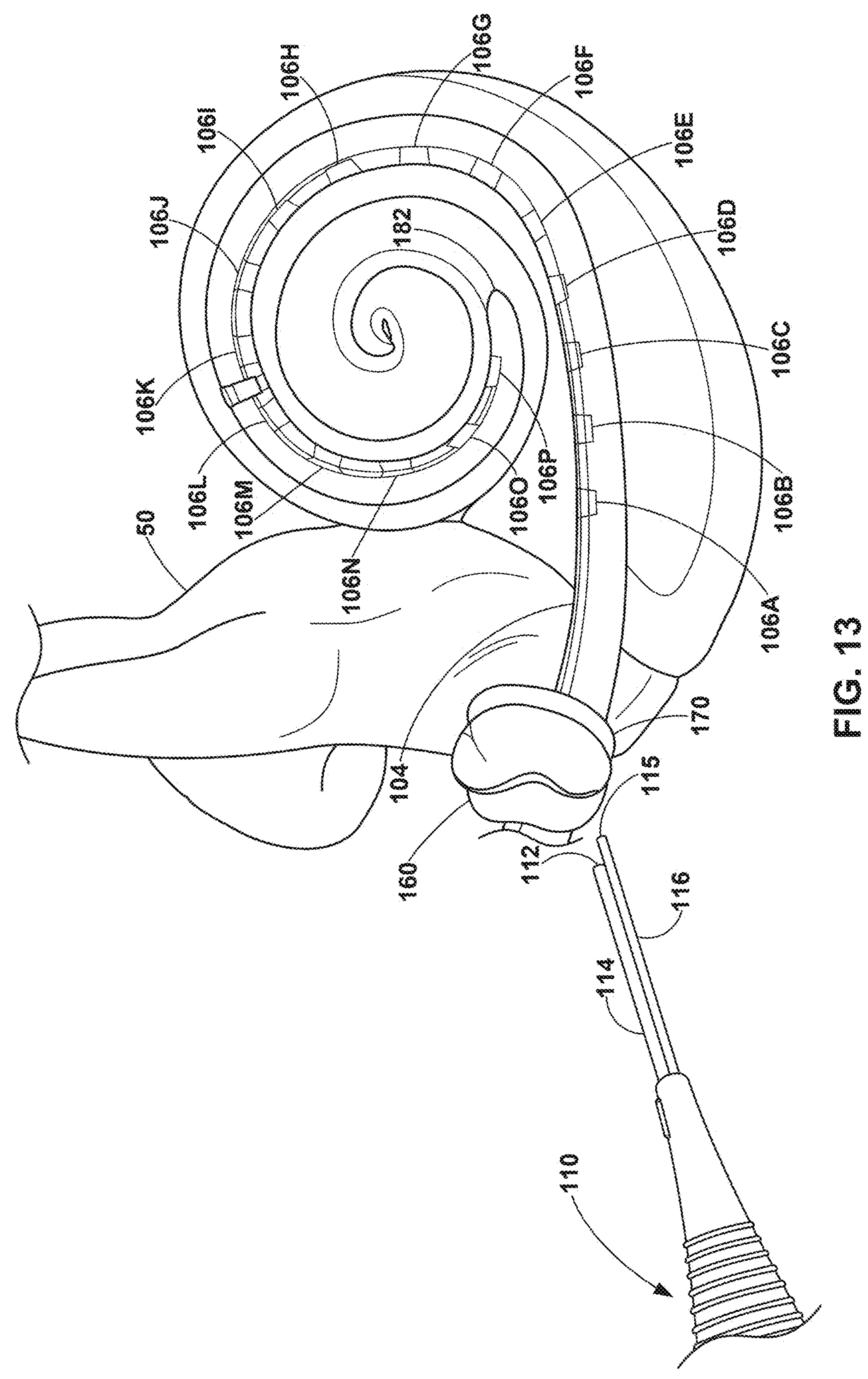
FIG. 13 shows the delivery tool and a cochlear implant lead extending through a patient's cochlea.

Referring now to FIG. 13, delivery tool 110 can deliver a therapeutic formulation 160 to a cochlear implant lead insertion site 170. This cochlear implant lead insertion site 170 can be, in some examples, the round window membrane of the cochlea or a cochleostomy that is separate from the round window membrane. In any case, the cochlear implant lead insertion site 170 can be an opening where a cochlear implant lead 104 enters the cochlea 50. As seen in FIG. 13, the cochlear implant lead 104 can extend along an interior of the cochlea 50 from the cochlear implant lead insertion site 170, with the cochlear implant lead 104 following a spiral pathway of the cochlea 50. In the example depicted in FIG. 13, the cochlear implant lead 104 can extend around an outer layer of the cochlear spiral. The cochlear implant lead 104 can terminate at distal tip 182 without extending to one or more inner layers of the cochlear spiral.

The cochlear implant lead can include a set of electrodes 106A-106P (collectively, "electrodes 106"). These electrodes 106 can be located along a distal portion of the cochlear implant lead 104 that is inserted within the cochlea 50, as depicted in FIG. 13. In some embodiments, electrodes 106 are connected to a common conductor that extends along the cochlear implant lead 104, but this is not required. Cochlear implant lead 104 can include more than one conductor in some embodiments, with each conductor connected to one or more of the electrodes 106. In some examples, electrodes 106 can deliver electrical stimulation to the cochlea 50 of the patient. For example, electrodes 106 can stimulate a cochlear nerve of the patient. This can cause the cochlear nerve to deliver signals to the patient's brain, causing the patient to experience hearing sensations. Cochlear implant lead 104 can therefore treat one or more patient conditions such as SNHL where the cochlear nerve is not adequately stimulated.

In some examples, a clinician can deliver the cochlear implant lead 104 through a surgical pathway across the mastoid bone of the patient. This surgical pathway allows the clinician to advance the cochlear implant lead 104 into the cochlea 50 through the cochlear implant lead insertion site 170. The clinician can place a distal tip 182 of the cochlear implant lead 104 into the cochlear implant lead insertion site 170 and subsequently guide the cochlear implant lead 104 into the cochlea 50 by advancing the cochlear implant lead 104 into an interior passageway of the cochlea 50. The clinician can advance the cochlear implant lead 104 until it reaches a position depicted in FIG. 13.

When the cochlear implant lead 104 is fully inserted into the cochlea 50, the clinician can advance delivery tool 110 to the cochlear implant lead insertion site 170 to deliver the therapeutic formulation 160. In cases where the clinician has already opened a transmastoid pathway to the cochlea 50 for the purpose of delivering the cochlear implant lead 104, delivery tool 110 can use this transmastoid pathway to reach the cochlear implant lead insertion site 170. Delivery tool 110 is not limited to using the transmastoid pathway to reach cochlear implant lead insertion site 170 and can, in some embodiments, use a transcanal pathway to reach the cochlear implant lead insertion site 170 (e.g., through the patient's ear canal and across the patient's tympanic membrane).

As depicted in FIG. 13, the delivery tool 110 includes a first shaft 114 that includes a tip-mounted camera 112 on a distal end and a second shaft 116 that defines a distal port 115 at a distal end. The clinician can simultaneously advance the first shaft 114 and the second shaft 116 of the delivery tool 110 to the cochlear implant lead insertion site 170 so that the distal port 115 is proximate the cochlear implant lead insertion site 170 and tip-mounted camera 112 provides direct visualization of a distal portion of second shaft 116 relative to the cochlear implant lead insertion site 170. When the distal port 115 is located placed near the cochlear implant lead insertion site 170, the clinician can cause the delivery tool 110 to deliver the therapeutic formulation 160 to the cochlear implant lead insertion site 170. This therapeutic formulation 160 can, in some examples, seal the cochlear implant lead insertion site 170 as part of the procedure to deliver the cochlear implant lead 104.

Delivery tool 110 is not limited to delivering the therapeutic formulation 160 to seal the cochlear implant lead insertion site 170 as part of the procedure to deliver the cochlear implant lead 104. In some examples, delivery tool 110 can deliver therapeutic formulation to the cochlear implant lead insertion site 170 before the procedure to deliver the cochlear implant lead 104 begins or after the procedure to deliver the cochlear implant lead 104 has ended. For example, delivery tool 110 can deliver therapeutic formulation to the cochlear implant lead insertion site 170 using transcanal access before the procedure to deliver the cochlear implant lead 104 has begun when no transcanal pathway is open to the cochlea 50. This can help to prepare the cochlear implant lead insertion site 170 to eventually receive the cochlear implant lead 104. Delivery tool 110 can also deliver therapeutic formulation to the cochlear implant lead insertion site 170 using transcanal access after the procedure to deliver the cochlear implant lead 104 has ended. This can help the cochlear implant lead 104 to function after it has been delivered to the cochlea 50.

The formulation delivered by the devices, systems, and methods as described herein can be a gel, a spray, a mist, a liquid, a paste, a solution, a suspension, an emulsification, and so on, without limitation. In some embodiments, the formulation can contain permeation enhancers or magnetic microparticles to improve the rate of diffusion of the therapeutic agent(s) into the inner ear. In certain embodiments, the formulation can contain lipid encapsulated agents, microparticles, supraparticles or viral vectors, to improve the efficiency and/or extend the duration of the delivery of the therapeutic agent(s) into the inner ear. In particular embodiments, the formulation can contain contrast agents, dyes or stains for diagnostic imaging of the middle and inner ear. In some embodiments, the formulation can comprise or consist of a gel or another material that seals perilymph leakage on the oval window or the round window to treat or prevent a perilymph fistula.

In some embodiments, the formulation or otic composition (e.g., an extended-release otic composition) can be delivered to a subject from or with the help of the treatment devices described herein. Such a formulation may be delivered using an implantable formulation carrier such as an implant device, or by directly injecting or otherwise delivering the formulation.

In some embodiments, an extended-release formulation can include a polymer composition that can form a gel. For example, a polymer composition can include a functional polymer, wherein the functional polymer includes a first functional group, and a crosslinker, wherein the crosslinker includes a second functional group, and water, wherein a crosslinking reaction can occur between the first functional group and the second functional group to form a gel. In some embodiments, the functional polymer can be present in an amount of about 5% to about 15% by weight of the polymer composition. In some embodiments, the crosslinker can be present in an amount of about 0.2% to about 0.6% by weight of the polymer composition.

It will be appreciated that a first functional group (e.g., on a functional polymer) and a second functional group (e.g., on a crosslinker) should be such that a crosslinking reaction can occur. Therefore, the choice of functional polymer can be based on the choice of crosslinker, or vice versa. In some embodiments, a first functional group can be an N-hydroxysuccinimide (NHS) group and a second functional group can be an amine (e.g., a primary amine), or vice versa. In some cases, the functional polymer contains only electrophilic or nucleophilic functional groups, and the crosslinker contains only nucleophilic or electrophilic functional groups, respectively.

In some embodiments, the functional polymer is a multi-arm (e.g., 3-arm, 4-arm, 6-arm, or 8-arm) polyethylene glycol (PEG) including two more succinimidyl ester (e.g., a succinimidyl succinate or a succinimidyl glutarate) or sulfo-succinimidyl ester functional groups and the crosslinker contains a plurality of amine (e.g., primary amine) functional groups. In some embodiments, the multi-arm PEG can have two or more arms terminate in a succinimidyl ester functional group. In some embodiments, one or monomers of the multi-arm PEG can include a succinimidyl ester functional group. In some embodiments, the crosslinker can be a polylysine (e.g., an epsilon-polylysine) (e.g., trilysine, tetralysine, or pentalysine). For example, in some embodiments, the functional polymer can be pentaerythritol poly (ethylene glycol) ether tetrasuccinimidyl glutarate, and the crosslinker can be trilysine.

In some embodiments, the functional polymer is a multi-arm (e.g., 3-arm 4-arm, 6-arm, or 8-arm) polyethylene glycol including two or more amine (e.g., primary amine) functional groups and the crosslinker includes a plurality of succinimidyl ester (e.g., a succinimidyl succinate or succinimidyl glutarate) or sulfo-succinimidyl ester functional groups. In some embodiments, the multi-arm PEG can have two or more arms terminate in an amine (e.g., primary amine) functional group. In some embodiments, one or more monomers of the multi-arm PEG can include an amine (e.g., primary amine) functional group. In some embodiments, the crosslinker can be disuccinimidyl glutarate, disuccinimidyl suberate, bis(sulfosuccinimidyl)suberate, or disuccinimidyl succinate.

In some embodiments, an extended-release otic composition can include an active agent (e.g., a therapeutic agent, a prophylactic agent, a diagnostic or visualization agent, or a combination thereof). An active agent can include, for example, a protein (e.g., an enzyme, a growth factor, an antibody or an antigen-binding fragment thereof), a carbohydrate (e.g., a glycosaminoglycan), a nucleic acid (e.g., an antisense oligonucleotide, an aptamer, a micro RNA, a short interfering RNA, or a ribozyme), small molecules, or combinations thereof. In some embodiments, a small molecule can include an antibiotic, an antineoplastic agent (e.g., doxorubicin), a local anesthetic, a steroid (e.g., dexamethasone), a hormone, an apoptotic inhibitor, an angiogenic agent, an anti-angiogenic agent (e.g., a VEGF inhibitor), a neurotransmitter, a neuroprotectant (e.g., a Rho Kinase inhibitor), a neurotrophin (e.g., BDNF, NGF or NT3), a psychoactive drug, an anti-inflammatory, and combinations thereof.

In some embodiments, an active agent of the formulation can include an anti-angiogenic agent. In some embodiments, an anti-angiogenic agent can be a VEGF inhibitor. In some cases, a VEGF inhibitor can be an antibody or an antigen-binding fragment thereof, a decoy receptor, a VEGFR kinase inhibitor, an allosteric modulator of a VEGFR, or a combination thereof. In some cases, a VEGF inhibitor can be an antibody or an antigen-binding fragment thereof. For example, in some embodiments, a VEGF inhibitor can be alacizumab, bevacizumab (AVASTIN®), icrucumab (IMC-18F1), ramucirumab (LY3009806, IMC-1121B, CYRAMZA®), or ranibizumab (LUCENTIS®). In some embodiments, a VEGF inhibitor can be a decoy receptor (e.g., aflibercept). In some embodiments, a VEGF inhibitor can be a VEGFR kinase inhibitor, such as agerafenib, altiratinib, apatinib, axitinib, cabozantinib, cediranib, lapatinib, lenvatinib, motesanib, nintedanib, pazopanib, pegaptanib, rebastinib, regorafenib, semaxanib, sorafenib, sunitinib, toceranib, tivozanib, or vandetanib. Other examples of VEGF inhibitors may be known in the art. In some embodiments, a VEGFR inhibitor can be an allosteric modulator of a VEGFR (e.g, cyclotraxin B).

An extended release formulation or otic composition can, in some cases, be useful to treat an otic disease or disorder, such as Ménière's Disease (MD), Autoimmune Inner Ear Disease (AIED), sudden sensorineural hearing loss (SSNHL), noise-induced hearing loss (NIHL), age-related hearing loss, sensorineural hearing loss associated with diabetes, tinnitus, damaged cilia from an autoimmune disorder, damaged cilia from an infection, damaged cilia from excess fluid or pressure, hearing loss due to chemotherapy, or a combination thereof.

Formulations that can be delivered from or with the help of the treatment devices described herein can also include but are not limited to antioxidants, anti-inflammatories, steroids, antimicrobials, NMDA receptor antagonists, nootropics, anti-apoptotic agents, neurotrophins, neuroprotective agents, neural protective proteins such as CNTF, BDNF, PEDF, NGF, NT-3, and the like, cannabinoids, monoclonal antibodies, other proteins, gene therapy, iRNA, tyrosine kinase inhibitors (TKIs), dual leucine zipper kinase (DLK) inhibitors, Wnt inhibitors, Wnt activators, Rho Kinase Inhibitors and protein therapies like anti-VEGF or neurotrophins.

As an example, the therapeutic agent of the formulation can include, but is not limited to antimicrobials such as antibiotics such as tetracycline, chlortetracycline, bacitracin, neomycin, polymyxin, gramicidin, cephalexin, oxytetracycline, chloramphenicol kanamycin, rifampicin, ciprofloxacin, tobramycin, gentamycin, erythromycin and penicillin; antifungals such as amphotericin B, clotrimazole, ketoconazole and miconazole; anti-bacterials such as sulfonamides, sulfadiazine, sulfacetamide, sulfamethizole and sulfisoxazole, nitrofurazone and sodium propionate; antivirals such as idoxuridine, trifluorotymidine, acyclovir, ganciclovir and interferon; antiallergenics such as sodium cromoglycate, antazoline, methapyriline, chlorpheniramine, pyrilamine, cetirizine and prophenpyridamine; anti-inflammatories such as hydrocortisone, hydrocortisone acetate, dexamethasone, dexamethasone 21-phosphate, fluocinolone, medrysone, prednisolone, prednisolone 21-phosphate, prednisolone acetate, fluoromethalone, betamethasone, and triamcinolone; non-steroidal anti-inflammatories such as salicylate, indomethacin, ibuprofen, diclofenac, flurbiprofen and piroxicam; decongestants such as phenylephrine, naphazoline and tetrahydrozoline; miotics and anticholinesterases such as pilocarpine, salicylate, acetylcholine chloride, physostigmine, eserine, carbachol, diisopropyl fluorophosphate, phospholine iodide and demecarium bromide; mydriatics such as atropine sulfate, cyclopentolate, homatropine, scopolamine, tropicamide, eucatropine and hydroxyamphetamine; sypathomimetics such as epinephrine; antineoplastics such as carmustine, cisplatin and fluorouracil; immunological drugs such as vaccines and immune stimulants; hormonal agents such as estrogens, estradiol, progestational, progesterone, insulin, calcitonin, parathyroid hormone and peptide and vasopressin hypothalamus releasing factor; beta adrenergic blockers such as timolol maleate, levobunolol HCl and betaxolol HCl; growth factors such as epidermal growth factor, fibroblast growth factor, platelet derived growth factor, transforming growth factor beta, somatotropin and fibronectin; carbonic anhydrase inhibitors such as dichlorophenamide, acetazolamide and methazolamide and other drugs such as prostaglandins, antiprostaglandins and prostaglandin precursors; keratolytic agents such as selenium sulfide, imiquimod, salicylic acid, and retinoids; antioxidants, NMDA receptor antagonists, nootropics, anti-apoptotic agents, neurotrophins, neuroprotective agents, tyrosine kinase inhibitors (TKIs), dual leucine zipper kinase (DLK) inhibitors, Rho-kinase (ROCK) inhibitors, cannabinoids, monoclonal antibodies, antibody fragments, other proteins, and gene therapy. Other therapeutic agents known to those skilled in the art which are capable of controlled, sustained release into the ear in the manner described herein are also suitable for use in accordance with embodiments of the devices described herein.

The therapeutic agent of the formulation can include, but is not limited to sodium thiosulfate to protect against cisplatin-induced hearing loss; thiouracil to protect against cisplatin-induced hearing loss; NMDA receptor antagonists for the treatment of tinnitus (AM-101; Auris Medical); AM-111 containing the synthetic peptide D-JNKI-1 (D-stereoisomer of c-Jun N-terminal Kinase Inhibitor 1; Auris Medical) for otoprotection in acute inner ear hearing loss; dexamethasone and other corticosteroids for the treatment of Meniere's Disease and forms of vestibular disorders and/or hearing loss associated with inflammation; D-methionine (Southern Illinois University) to protect against Noise-induced hearing loss; PIPE-505, LY411575, and LY3056480 (selective gamma secretase inhibitors that block Notch activation); Verosudil (AR-12286) and Netarsudil to treat synaptopathy; BDNF to treat synaptopathy; NGF; and NT-3 neurotrophic factor.

The therapeutic agent of the formulation can include but is not limited to local anesthetics for delivery into the ear canal including benzocaine, antipyrine, butamben, dibucaine, lidocaine, prilocaine, oxybuprocaine, pramoxine, proparacaine, proxymetacaine, and tetracaine.

Various pharmaceutically acceptable carriers for the therapeutic agents described herein can include such as, for example, solids such as starch, gelatin, sugars, natural gums such as acacia, sodium alginate and carboxymethyl cellulose; polymers such as silicone rubber; liquids such as sterile water, saline, dextrose, dextrose in water or saline; condensation products of castor oil and ethylene oxide, liquid glyceryl triester of a lower molecular weight fatty acid; lower alkanols; oils such as corn oil, peanut oil, sesame oil, castor oil, and the like, with emulsifiers such as mono- or di-glyceride of a fatty acid, or a phosphatide such as lecithin, polysorbate 80, and the like; glycols and polyalkylene glycols including P407 and other combinations of polyethylene glycol and polypropylene glycol; aqueous media in the presence of a suspending agent, for example, sodium carboxymethylcellulose, hyaluronic acid, sodium hyaluronate, sodium alginate, poly(vinyl pyrrolidone) and similar compounds, either alone, or with suitable dispensing agents such as lecithin, cyclodextrins, polyoxyethylene stearate and the like. The carrier may also contain adjuvants such as preserving, stabilizing, wetting, emulsifying agents or other related materials.

A therapeutic agent referred to with a trade name encompasses one or more of the formulation of the therapeutic agent commercially available under the tradename, the active ingredient of the commercially available formulation, the generic name of the active ingredient, or the molecule comprising the active ingredient. As used herein, a therapeutic or therapeutic agents are agents that ameliorate the symptoms of a disease or disorder or ameliorate the disease or disorder. Therapeutic agent, therapeutic compound, therapeutic regimen, or chemotherapeutic include conventional drugs and drug therapies, including vaccines, which are known to those skilled in the art and described elsewhere herein. Therapeutic agents include, but are not limited to, moieties that are capable of controlled, sustained release into the body.

While the devices, systems, materials, compounds, compositions, articles, and methods described herein described in the context of treating hearing loss, it should be understood that the devices, systems, materials, compounds, compositions, articles, and methods may be used to treat any disorder of the middle ear and/or inner ear including, but not limited to, tinnitus, balance disorders including vertigo, Meniere's Disease, vestibular neuronitis, vestibular schwannoma, labyrinthitis, otosclerosis, ossicular chain dislocation, cholesteatoma, otitis media, middle ear infections, and tympanic membrane perforations, to provide a few examples.

Although the round window membrane is one targeted site for therapeutic agent delivery or access, the systems and methods described herein can also be used for precise delivery of therapeutic agents to other targeted sites, such as the oval window or other parts of the middle ear cavity, and for providing access to other features or regions of the middle ear. For example, the systems and methods described herein can be used for minimally invasive surgical reconstruction of the ossicular chain, for removal of cholesteatoma, for diagnostic assessment, and other procedures. Any and all such techniques for using the systems and methods described herein are included within the scope of this disclosure.

The devices, systems, materials, compounds, compositions, articles, and methods described herein may be understood by reference to the above detailed description of specific aspects of the disclosed subject matter. It is to be understood, however, that the aspects described above are not limited to specific devices, systems, methods, or specific agents, as such may vary. It is also to be understood that the terminology used herein is for the purpose of describing particular aspects only and is not intended to be limiting.

A number of embodiments have been described. Nevertheless, it will be understood that various modifications may be made without departing from the claim scope here. Accordingly, other embodiments are within the scope of the following claims.

What is claimed is:

1. A method of delivering a self-gelling therapeutic composition at a cochlear implant lead insertion site of a cochlea, the method comprising:

inserting a therapeutic gel delivery shaft through a transmastoid pathway toward a cochlear implant lead;

while the therapeutic gel delivery shaft is positioned through the transmastoid pathway such that a distal port of the therapeutic gel delivery shaft is proximate to the cochlear implant lead, depositing a liquid dosage of the self-gelling therapeutic composition out of the distal port of the therapeutic gel delivery shaft onto an exterior of the cochlear implant lead at the cochlear implant lead insertion site of a round window niche of the cochlea, said self-gelling therapeutic composition comprising: an anti-inflammatory therapeutic agent and a polymer gel composition including water, a functional polymer of about 5% to about 15% by weight of the polymer gel composition, and a crosslinker of about 0.2% to about 0.6% by weight of the polymer gel composition, wherein the distal port of the therapeutic gel delivery shaft is sized to deposit the liquid dosage of the self-gelling therapeutic composition to output a sustained release of the anti-inflammatory therapeutic agent into the cochlea; and after said depositing the liquid dosage of the self-gelling therapeutic composition out of the distal port of the therapeutic gel delivery shaft, using direct visualization of the cochlear implant lead insertion site to verify that the self-gelling therapeutic composition is retained as a gel substance along the exterior of the cochlear implant lead at the round window niche of the cochlea.

2. The method of claim 1, wherein the self-gelling therapeutic composition is retained as the gel substance to seal the cochlear implant lead insertion site at the round window niche of the cochlea.

3. The method of claim 1, further comprising withdrawing the therapeutic gel delivery shaft from the transmastoid pathway while the self-gelling therapeutic composition is retained as the gel substance along the cochlear implant lead at the round window niche of the cochlea such that the gel substance both outputs the sustained release of the anti-inflammatory therapeutic agent into the cochlea and seals the cochlear implant lead insertion site.

4. The method of claim 3, wherein the sustained release of the anti-inflammatory therapeutic agent occurs over a period of weeks after said depositing the liquid dosage of the self-gelling therapeutic composition.

5. The method of claim 4, wherein the sustained release of the anti-inflammatory therapeutic agent encompasses any one or a combination of a first order release, a zero order release, and an intermediate release to the zero order release and the first order release.

6. The method of claim 4, wherein the sustained release of the anti-inflammatory therapeutic agent comprises a controlled release of the anti-inflammatory therapeutic agent via passive molecular diffusion driven by a concentration gradient across a membrane.

7. The method of claim 1, further comprising urging the self-gelling therapeutic composition to flow from a reservoir containing the self-gelling therapeutic composition toward the distal port of the therapeutic gel delivery shaft in response to movement of an actuator of the reservoir.

8. The method of claim 7, wherein the actuator of the reservoir is a syringe plunger of a treatment actuator device.

9. The method of claim 8, wherein the treatment actuator device comprises the reservoir, the syringe plunger, and a flexible tube extending distally from the reservoir and in fluid communication with the therapeutic gel delivery shaft.

10. The method of claim 9, wherein the flexible tube of the treatment actuator device is releasably mated to a Luer lock connector coupled to the therapeutic gel delivery shaft.

11. The method of claim 1, wherein said using direct visualization of the cochlear implant lead insertion site comprises capturing image data of the distal port of the therapeutic gel delivery shaft using a camera device.

12. The method of claim 11, wherein said using direct visualization of the cochlear implant lead insertion site comprises simultaneously capturing image data of both the distal port of the therapeutic gel delivery shaft and the self-gelling therapeutic composition deposited at the cochlear implant lead insertion site of the cochlea.

13. The method of claim 11, wherein said using direct visualization of the cochlear implant lead insertion site comprises the capturing image data of the distal port of the therapeutic gel delivery shaft using the camera device including a tip-mounted camera fixedly mounted at a distal end of a visualization shaft and oriented toward the distal port of the therapeutic gel delivery shaft.

14. The method of claim 13, wherein the image data captured by the tip-mounted camera is communicated via an image data cable to a user interface display to present a real-time location of the deposited self-gelling therapeutic composition relative to the cochlear implant lead insertion site and relative to the distal port.

15. The method of claim 13, wherein the therapeutic gel delivery shaft and the visualization shaft are side-by-side shafts being fixedly mounted to a handle in a stationary position relative to one another and extending distally from the handle such that the distal port of the therapeutic gel delivery shaft is positioned distally of the visualization shaft, the tip-mounted camera capturing the distal port of the therapeutic gel delivery shaft from a position that is fixed relative to the therapeutic gel delivery shaft.

16. The method of claim 15, wherein the visualization shaft and the therapeutic gel delivery shaft are sized so that the distal port of the therapeutic gel delivery shaft and the tip-mounted camera both fit within a middle ear while the tip-mounted camera provides the direct visualization of the therapeutic gel delivery shaft during said depositing the liquid dosage of the self-gelling therapeutic composition from the distal port of the therapeutic gel delivery shaft at the cochlear implant lead insertion site.

17. The method of claim 15, wherein the distal port of the therapeutic gel delivery shaft extends distally beyond the tip-mounted camera by a distal extension distance within a range from 1 mm to 5 mm.

18. The method of claim 15, wherein the visualization shaft has an exterior diameter that is larger than an outer diameter of the therapeutic gel delivery shaft, and a combined maximum width of the visualization shaft and the therapeutic gel delivery shaft is less than 2 mm so that the side-by-side shafts are sized to fit within the transmastoid pathway during said depositing the liquid dosage of the self-gelling therapeutic composition.

19. The method of claim 18, wherein at least a portion of the side-by-side shafts are located within the transmastoid pathway and the handle is located fully outside of the transmastoid pathway during said depositing the liquid dosage of the self-gelling therapeutic composition from the distal port of the therapeutic gel delivery shaft at the cochlear implant lead insertion site.

20. The method of claim 18, wherein a maximum width of the handle is greater than the combined maximum width of the visualization shaft and the therapeutic gel delivery shaft.

21. The method of claim 13, wherein the visualization shaft includes both the tip-mounted camera mounted at a first location on the distal end of the visualization shaft and an illumination source mounted at a second location on the distal end of the visualization shaft so as to emit light distally toward the distal port of the therapeutic gel delivery shaft.

22. A method of delivering a self-gelling therapeutic formulation at a cochlear implant lead insertion site of a cochlea, the method comprising:

inserting a therapeutic gel delivery shaft through a transmastoid pathway toward a cochlear implant lead;

while the therapeutic gel delivery shaft is positioned through the transmastoid pathway such that a distal port of the therapeutic gel delivery shaft is proximate to the cochlear implant lead, depositing the self-gelling therapeutic formulation out of the distal port of the therapeutic gel delivery shaft onto the cochlear implant lead insertion site at a round window niche of the cochlea, said self-gelling therapeutic formulation comprising: an anti-inflammatory therapeutic agent and a polymer gel composition including water, a functional polymer of about 5% to about 15% by weight of the polymer gel composition, and a crosslinker of about 0.2% to about 0.6% by weight of the polymer gel composition, wherein the distal port of the therapeutic gel delivery shaft is sized to deposit a dosage of the self-gelling therapeutic formulation to output a sustained release of the anti-inflammatory therapeutic agent into the cochlea;

after said depositing the self-gelling therapeutic formulation out of the distal port of the therapeutic gel delivery shaft, using direct visualization of the cochlear implant lead insertion site to verify that the self-gelling therapeutic formulation is retained as a gel substance along the cochlear implant lead at the round window niche of the cochlea, wherein said depositing the self-gelling therapeutic formulation causes the self-gelling therapeutic formulation to seal the cochlear implant lead insertion site at the round window niche of the cochlea; and inserting the cochlear implant lead into the cochlea prior to said depositing the self-gelling therapeutic formulation out of the distal port of the therapeutic gel delivery shaft onto the cochlear implant lead insertion site at the round window niche of the cochlea.

23. The method of claim 22, further comprising, prior to said inserting the cochlear implant lead into the cochlea, depositing an initial dose of the self-gelling therapeutic formulation at the round window niche of the cochlea.

* * * * *